United States Patent
Bannister et al.

(10) Patent No.: US 10,947,308 B2
(45) Date of Patent: Mar. 16, 2021

(54) COMPOSITION FOR TREATMENT OF DISORDERS

(71) Applicant: CRESCENDO BIOLOGICS LIMITED, Cambridge (GB)

(72) Inventors: Karen Bannister, Cambridge (GB); Ulla Lashmar, London (GB); Daniel Pettit, Billingham (GB); Thomas Sandal, Cambridge (GB)

(73) Assignee: Crescendo Biologics Limited, Cambridge (GB)

(*) Notice: Subject to any disclaimer, the term of this patent is extended or adjusted under 35 U.S.C. 154(b) by 83 days.

(21) Appl. No.: 16/316,925

(22) PCT Filed: Jul. 10, 2017

(86) PCT No.: PCT/GB2017/052021
§ 371 (c)(1),
(2) Date: Jan. 10, 2019

(87) PCT Pub. No.: WO2018/011555
PCT Pub. Date: Jan. 18, 2018

(65) Prior Publication Data
US 2019/0300603 A1    Oct. 3, 2019

(30) Foreign Application Priority Data

Jul. 11, 2016  (GB) .................................. 1612043.8

(51) Int. Cl.
| C07K 16/24 | (2006.01) |
| A61K 39/395 | (2006.01) |
| A61K 9/00 | (2006.01) |
| A61K 47/10 | (2017.01) |
| A61K 47/18 | (2017.01) |
| A61K 47/26 | (2006.01) |
| A61K 47/34 | (2017.01) |
| A61K 9/19 | (2006.01) |
| C07K 14/54 | (2006.01) |
| A61K 39/00 | (2006.01) |

(52) U.S. Cl.
CPC .......... *C07K 16/244* (2013.01); *A61K 9/0014* (2013.01); *A61K 9/0019* (2013.01); *A61K 9/19* (2013.01); *A61K 39/3955* (2013.01); *A61K 39/39591* (2013.01); *A61K 47/10* (2013.01); *A61K 47/183* (2013.01); *A61K 47/26* (2013.01); *A61K 47/34* (2013.01); *A61K 2039/505* (2013.01); *C07K 2317/565* (2013.01); *C07K 2317/569* (2013.01)

(58) Field of Classification Search
None
See application file for complete search history.

(56) References Cited

FOREIGN PATENT DOCUMENTS

| WO | 2010/177422 A2 | 7/2010 |
| WO | WO 2012/156219 | 11/2012 |
| WO | 2014/184352 A1 | 11/2014 |
| WO | WO 2016/113557 | 7/2016 |

OTHER PUBLICATIONS

Rouet et al, the Journal of Biological Chemistry; 2015; vol. 290, No. 19, pp. 11905-11917.*
Muyldermans, Annual Review of Biochemistry; 2013; vol. 82, pp. 775-797.*
Brummell et al, Biochemistry; 1993; vol. 32, pp. 1180-1187.*
Kobayashi et al. Protein Engineering; 1999; vol. 12, pp. 879-844.*
Brorson et al. J. Immunol; 1999; vol. 163, pp. 6694-6701.*
Coleman Research in Immunol; 1994; vol. 145; pp. 33-36.*
Jang et al. Molec. Immunol. 35:1207-1217; 1998.*
Burks et al. (PNAS 94:412-417 (1997)).*
Zhu et al, (Clinical Science (2012) 122, 487-511.*
Daugherty, Ann L. et al. "Formulation and Delivery Issues for Monoclonal Antibody Therapeutics". Chapter 8. 2010.
Wang, Wei, et al. "Antibody Structure, Instability, and Formulation". Journal of Pharmaceutical Sciences, vol. 96, No. 1, Jan. 2007.
International Search Report for PCT/GB2017/052021 dated Sep. 26, 2017.
Steven J. Shire, et al., Challenges in the Development of High Protein Concentration Formulations, Journal of Pharmaceutical Sciences (Jun. 2004) vol. 93, No. 6, p. 1390-1402.
Examination Report dated Aug. 3, 2020 in corresponding Application EP17740072.3.

* cited by examiner

*Primary Examiner* — Bridget E Bunner
*Assistant Examiner* — Fozia Hamud

(57) ABSTRACT

The invention relates to stable and non-aggregating compositions comprising an IL-17A binding molecule, in particular a single domain antibody. Such compositions are useful for topical administration in the treatment of disease, for example skin disease or asthma.

Figure 1:
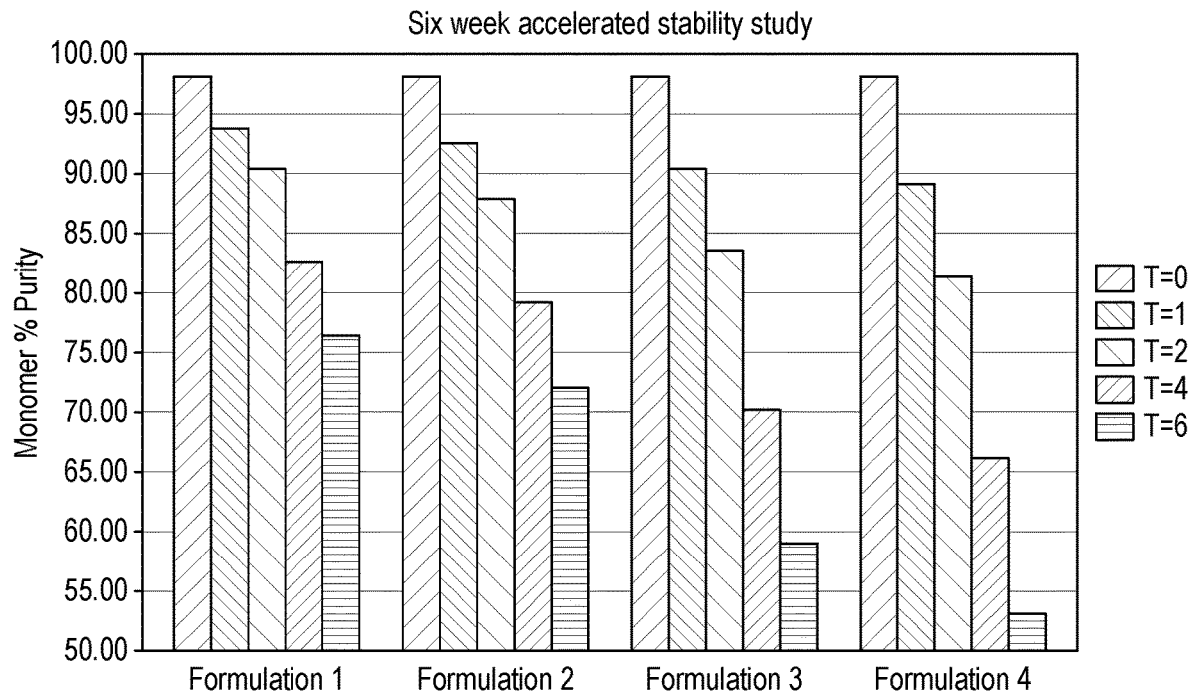

18 Claims, 10 Drawing Sheets
Specification includes a Sequence Listing.

COMPOSITION FOR TREATMENT OF DISORDERS

FIELD OF THE INVENTION

The invention relates to stable and non-aggregating compositions comprising an IL-17A binding molecule in particular for topical administration, and the use of such compositions in the treatment of disease.

INTRODUCTION

Psoriasis is a chronic relapsing and remitting inflammatory skin disease affecting 2-3% of the world's population (~125 m sufferers) that causes significant morbidity and decreased quality of life, largely due to clinical flare-ups and disfiguring lesions in visible areas of the skin, systemic manifestations and drug-related side effects. The common form of the disease, termed 'plaque psoriasis vulgaris', is observed in more than 80% of patients and is characterized by erythematous scaly plaques (typically on elbows, knees, scalp and buttocks) which can vary in size from minimal to the involvement of the entire skin surface.

Depending on the degree of body surface area (BSA) involvement, psoriasis can be categorised into mild (<3% BSA involvement), moderate (3-10% BSA) and severe (>10% BSA) disease. Topical agents such as corticosteroids, vitamin D derivatives, coal tar and topical retinoids are the cornerstone of the initial management of psoriasis and are an important part of the treatment ladder applied to patients across the spectrum of disease severity. Patients diagnosed with mild-to-moderate disease are typically prescribed topical agents as monotherapy. Patients with severe disease are typically prescribed topical agents as an adjunct to phototherapy or systemic (small molecule) therapies such as methotrexate, cyclosporine or oral retinoids. The treatment regime for moderate-to-severe psoriasis also includes antibody-based therapies.

The therapeutic products currently on the market for the treatment of psoriasis offer varying degrees of symptomatic relief and reduced relapse rates but none are currently considered curative and they therefore require chronic administration. While many pre-existing topical agents can be effective for short periods of time, due to treatment-limiting toxicity most are restricted to short term use. This means that patients need routine monitoring for side effects and regular cycling onto new treatment protocols.

Patients with severe disease are typically prescribed topical agents as an adjunct to phototherapy or systemic (small molecule) therapies such as methotrexate, cyclosporine or oral retinoids (Nast et al., Arch Dermatol Res (2007) 299: 111-138). Phototherapy can be effective, but is inconvenient and associated with a significant risk of skin cancer. Small molecule systemic therapies are associated with increased cardiovascular risk; renal dysfunction, leucopenia and thrombocytopenia. For example, methotrexate may cause a neutropenia and liver damage and is contraindicated for males and females of reproductive age without due precaution. Cyclosporine is a potent immunosuppressant, which has potential adverse effects on the kidneys and blood pressure. Acitretin is an oral retinoid that has a range of side effects, and is also contraindicated for females of reproductive age without due precaution (Nast et al., Arch Dermatol Res (2007) 299:111-138).

The treatment regimen for moderate-to-severe psoriasis also includes antibody-based therapies. Approved treatments include adalimumab (Humira®), a humanized monoclonal antibody with activity against TNF-alpha($\alpha$), the TNF-$\alpha$ inhibitor etanercept (Enbrel®), the TNF-$\alpha$ inhibitor infliximab (Remicade®) and most recently ustekinumab (Stelara®), a human mAb that targets the common p40 subunit of IL-12 and IL-23, thereby blocking the signalling of both cytokines.

In recent years the importance of the Th17 pathway has become well validated in psoriasis and several monoclonal antibodies (mAbs) targeting IL-17 have shown the significant importance of modulating these cytokines and influencing psoriasis. IL-17, a T-cell derived cytokine, is a target for topical therapy in skin. While psoriasis may have a systemic component in some patients, the disease is primarily one of the skin. IL-17 secreted by Th17 cells acts on epidermal keratinocytes, via IL-17R complexes present on these cells, to initiate a feedback loop of keratinocyte hyper-proliferation and on-going inflammation, thereby generating the psoriatic plaque. It is believed that the primary element of pathological activity is locally in the skin, and therefore inhibition of the IL-17/IL-17R interaction is the best validated target for topical therapy. This is in contrast to other validated Th17 targets, such as IL-23, where a significant phase of activity is in regional lymph nodes.

Several other monoclonal antibodies agents have been shown to markedly reduce disease severity in patients with moderate-to-severe plaque psoriasis. These agents include ixekizumab (Taltz®) and secukinumab (Costentyx®), both of which target IL-17A, and brodalumab (Siliq®) that binds to and inhibits signalling of IL-17RA and therefore would be expected to block IL1-7 family members that utilize this receptor, including IL-17A, IL-17F, IL-17A/F and possibly IL-17E. The preliminary clinical results for IL-17 inhibitors indicate the importance of IL-17A in psoriasis pathophysiology. In independent clinical trials programmes up to and including substantial confirmatory Phase III trials, all three agents have been reported to reduce disease severity markedly in patients with moderate-to-severe plaque psoriasis. Secukinumab has been shown to down-regulate cytokines, chemokines and proteins associated with inflammatory responses in lesional skin. In summary, inhibition of IL-17A allows selective intervention to address the dysregulated immune system in plaque psoriasis (Girolomoni et al., The British Journal of Dermatology. 2012a; 167(4):717-724, Huebner et al., Gut 2012; 61: 1693-700, Papp et al., New Engl J Med 2012; 366: 1181-9, Mease et al., N Engl J Med. 2014 12; 370(24):2295-306 and Langley et al., New Engl J Med 2014; 371: 326-38).

The therapeutic products currently on the market for the treatment of psoriasis offer varying degrees of symptomatic relief and reduced relapse rates but none are currently considered curative and chronic administration is therefore required. While many pre-existing topical agents can be effective for short periods of time, due to treatment-limiting toxicity most are restricted to short term use. This means that patients need routine monitoring for side effects and regular cycling onto new treatment protocols. Phototherapy can be effective, but is inconvenient and associated with a significant risk of skin cancer and many conventional (small molecule) systemic therapies are associated with increased cardiovascular risk; renal dysfunction, leucopenia and thrombocytopenia. Systemic biologics have transformed treatment of moderate-to-severe psoriasis but, as with any immunosuppressive regime, chronic use can have significant side-effects such as increased risk of infections or malignancies. Therapeutic regimens have to take account of this by adopting strategies to reduce toxicity, including rotational or sequential therapies, drug holidays, and combination therapy. Importantly, for some drugs there is an absolute lifetime limit on the exposure that any one patient can safely receive.

The IL-17 family of cytokines includes six members, IL-17/IL-17A, IL-17B, IL-17C, IL-17D, IL-17E/IL-25, and IL-17F, which are produced by multiple cell types. Members of this family have a highly conserved C-terminus containing a cysteine-knot fold structure. Most IL-17 proteins are secreted as disulfide-linked dimers, with the exception of IL-17B, which is secreted as a non-covalent homodimer.

Signaling by IL-17 family cytokines is mediated by members of the IL-17 receptor family, IL-17 R/IL-17 RA, IL-17 B R/IL-17 RB, IL-17 RC, IL-17 RD, and IL-17 RE. Activation of these receptors triggers intracellular pathways that induce the production of pro-inflammatory cytokines and anti-microbial peptides. IL-17A, IL-17F, and IL-17A/F are produced primarily by activated T cells and signal through an oligomerized receptor complex consisting of IL-17 RA and IL-17 RC. Ligand binding to this complex leads to recruitment of the intracellular adaptor proteins, Act1 and TRAF-6, and downstream activation of the transcription factors, NF kappa B, AP-1, and C/EBP. IL-17E activates similar signaling pathways through a receptor complex formed by IL-17 RA and IL-17 B R/IL-17RB. Signaling by IL-17E induces Th2-type immune responses and may be involved in promoting the pathogenesis of asthma.

Less is known about the signaling pathways activated by other IL-17 family cytokines. Recent studies suggest that IL-17C is produced primarily by epithelial cells and binds to a receptor complex consisting of IL-17 RA and IL-17 RE. Autocrine signaling by IL-17C in epithelial cells stimulates the production of anti-microbial peptides and pro-inflammatory cytokines, but like IL-17A, overexpression of IL-17C may contribute to the development of autoimmune diseases. Similar to IL-17E, IL-17B binds to IL-17 B R/IL-17 RB, but the major target cells and effects of IL-17B signaling have not been reported. In addition, the receptor for IL-17D and the ligand for IL-17 RD are currently unknown.

Single domain antibodies that bind to human IL17A are described in WO2016/113557 hereby incorporated in its entirety.

The IL-17 pathway plays a major role in the development of diseases such as psoriasis and asthma. IL-17 promotes psoriasis by contributing to the inflammatory response that damages and overturns the keratinocyte cells of the epidermal layer. Because of their role in disease, IL-17 inhibitors are being investigated as possible treatment for various diseases. However, development of stable and active protein formulations, in particular for topical delivery, can be a challenge due to issues relating to the physical and chemical stability of the protein, manufacture, storage, and delivery of the protein formulation.

As shown above, there is a need for new effective and safe therapy options of diseases associated with IL-17 signalling, for both topical and systemic use. In particular, there is a need for stable drug formulations in this field, in particular for topical formulations.

SUMMARY OF THE INVENTION

The invention relates to pharmaceutical compositions and formulations comprising isolated binding molecules capable of binding human IL-17A, in particular antibodies or fragments thereof for topical administration. Preferred fragments are single domain antibodies, in particular single variable heavy chain domain antibodies.

In one aspect, the invention relates to a composition comprising
  a) an effective amount of at least one single variable heavy chain domain antibody capable of binding human IL-17A,
  b) 10-150 mM Tris/glycine wherein the pH of said composition is about 5 to about 9.

For example, said single variable heavy chain domain antibody comprises a CDR3 having SEQ ID NO: 4. In another embodiment, said single variable heavy chain domain antibody comprises a CDR1 having SEQ ID NO: 2, a CDR2 having SEQ ID NO: 3 and a CDR3 having SEQ ID NO: 4. In another embodiment, said single variable heavy chain domain antibody comprises SEQ ID NO: 1 or a sequence having at least 75% homology thereto. In another embodiment, said single variable heavy chain domain antibody comprises SEQ ID NO: 74 or a sequence having at least 75% homology thereto.

In one embodiment, said composition further comprises one or more of the following excipients: 0.1-150 mM L-arginine/glutamic acid, 0.1-15% sorbitol and/or 0.1-30% propylene glycol.

In one aspect, the invention provides composition comprising
  a) an effective amount of at least one single domain antibody capable of binding human IL-17A wherein said single domain antibody domain comprises SEQ ID NO: 1 or a sequence having at least 75% homology thereto, b) 10-150 mM Tris/glycine and optionally comprising one or more of the following excipients: 0.1-150 mM L-arginine/glutamic acid, 0.1-15% sorbitol and/or 0.1-30% propylene glycol wherein the pH of said composition is about 5 to about 9.

The composition can be in liquid, spray dried or freeze dried form.

In one aspect, the invention relates to a composition comprising
  a) an effective amount of at least one single domain antibody capable of binding human IL-17A wherein said single domain antibody domain comprises SEQ ID No. 1 or a sequence having at least 75% homology thereto,
  b) 50-150 mM Tris/glycine
  c) 50-150 mM L-arginine/glutamic acid
  d) 5-15% sorbitol and
  e) 4-30% propylene glycol wherein the pH of said composition is about 5 to about 9.

In one embodiment, the invention relates to a composition comprising
  a) an effective amount of a single domain antibody capable of binding human IL-17A wherein said single domain antibody comprises SEQ ID NO: 1 or a sequence having at least 75% homology thereto,
  b) about 100 mM Tris/glycine,
  c) about 125 mM L-arginine/glutamic acid,
  d) about 10% sorbitol and
  e) about 6% propylene glycol wherein the pH of said composition is 7.5 to 8.5, for example about 8.

In one aspect, the invention relates to the use of a composition as above in the treatment of disease.

In one embodiment, the medicament is suitable for topical administration.

In one aspect, the invention relates to a method of treating a disease comprising administering a therapeutically effective amount of a composition as above.

In one aspect, the invention relates to a composition as above for use in the treatment of disease.

In one embodiment, the disease is selected from a skin disorder, for example psoriasis, spondyloarthropathies, uveitis, gingivitis or atopic dermatitis.

In one aspect, the invention relates to a freeze or spray dried composition comprising a) an effective amount of at least one single domain antibody capable of binding human IL-17A, for example a single domain antibody comprising SEQ ID NO: 1 or a sequence having at least 75% homology thereto, b) 10-150 mM Tris/glycine, wherein the pH of said composition is about 5 to about 9.

In one aspect, the invention relates to a reconstituted freeze or spray dried composition comprising a composition as above further comprising a reconstitution agent, such as propylene glycol and/or sorbitol.

In one aspect, the invention relates to a kit comprising a composition as above and optionally instructions for use.

In a further aspect, the invention relates to a container, for example a nebulizer or inhaler, comprising a composition as above.

In another aspect, the invention relates to a method for making a reconstituted formulation for topical administration comprising providing a composition as above and adding a reconstitution agent, such as propylene glycol.

In another aspect, the invention relates to a cream, ointment, lotion, gel, patch, plaster, dressing, vapour or powder or liquid for topical administration comprising a composition as above.

In another aspect, the invention relates to the use of a buffer comprising 10-150 mM Tris/glycine in preparing a formulation comprising an effective amount of a single domain antibody capable of binding human IL-17A for example a single domain antibody comprising SEQ ID NO: 1 or a sequence having at least 75% homology thereto.

In one embodiment, the buffer comprises a) about 100 mM Tris/glycine, b) about 125 mM L-arginine/glutamic acid, c) about 10% sorbitol and d) about 6% propylene glycol wherein the pH of said composition is 7.5 to 8.5, for example about 8.

In one aspect, the invention relates to a method for making a composition as described above comprising combining a drug substance buffer as described above with an IL-17 molecule binding molecule.

In one aspect, the invention relates to a method for preparing a formulation for the treatment of a disorder comprising adding an effective amount of a single domain antibody capable of binding human IL-17A wherein for example a single domain antibody comprising SEQ ID NO: 1 or a sequence having at least 75% homology thereto a buffer comprising 10-150 mM Tris/glycine.

DRAWINGS

The invention is further described in the following non-limiting drawings.

FIG. 1. Six week accelerated stability study on the top four Drug Substance formulations. (T=0 to T=6 shown for each formulation from left to right).

Figure 2:
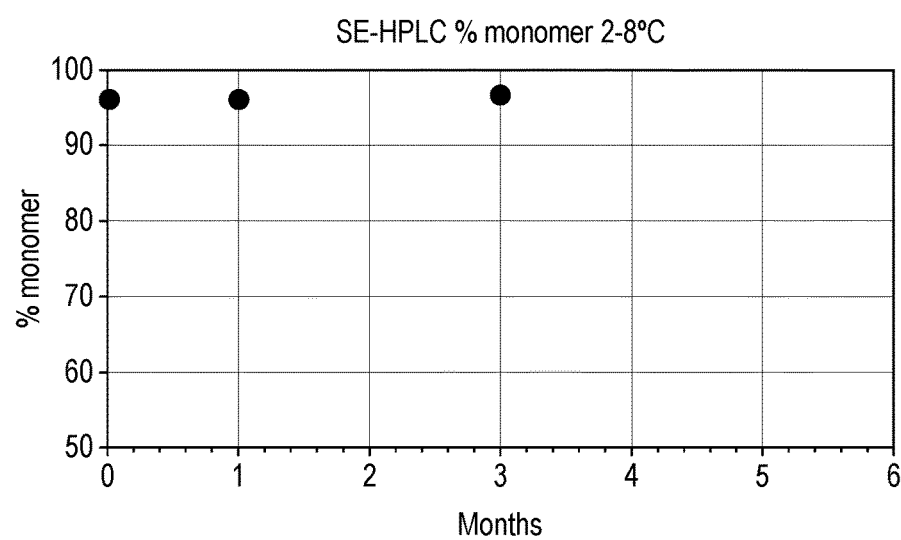

FIG. 2. Stability of anti IL-17A $V_H$1.1 (SEQ ID NO: 74) at 40 mg/mL in drug substance buffer at 2-8° C. storage over 3 months. Measured using SE-HPLC.

Figure 3:
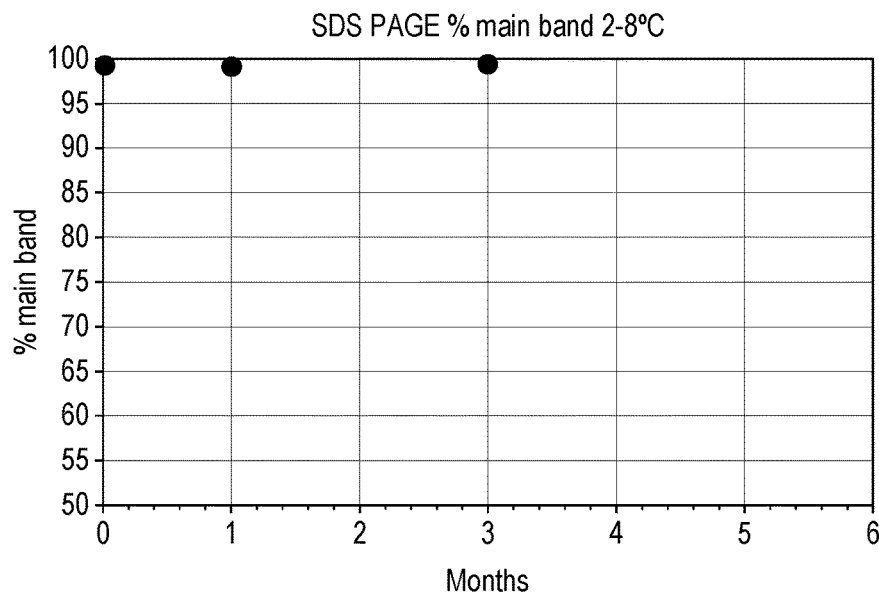

FIG. 3. anti IL-17A $V_H$1.1 (SEQ ID NO: 74) at 40 mg/mL in drug substance buffer at 2-8° C. storage over 3 months. Measured using SDS page.

Figure 4:
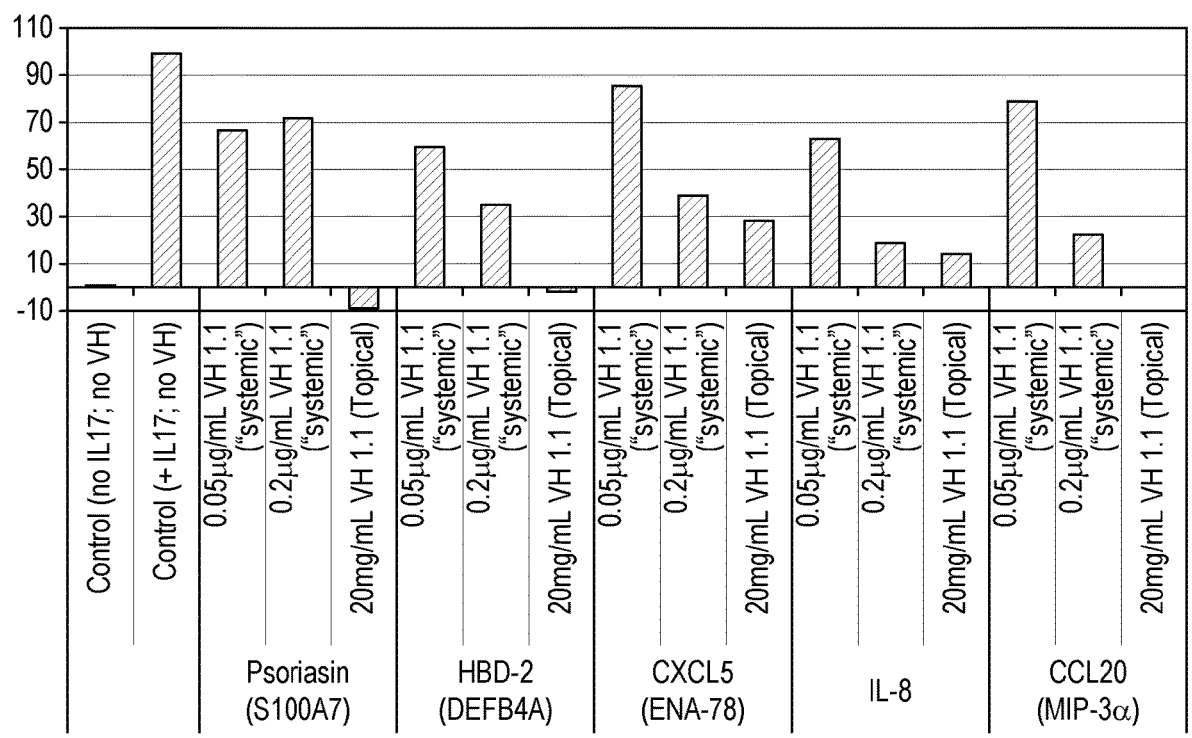

FIG. 4. Gene expression of several biomarkers inhibited by anti IL-17A $V_H$ 1.1 (SEQ ID NO: 74) in formulation in in vitro psoriatic skin model. X axis: tested formulations and biomarkers. Y axis: percentage induction of gene expression FIG. 5. Cytokine/Chemokine inhibition by $V_H$1.1 (SEQ ID NO: 74) in formulation in in vitro psoriatic skin model. X axis: tested formulations and cytokine/chemokine. Y axis: Percent release of cytokine/chemokine.

Figure 6:
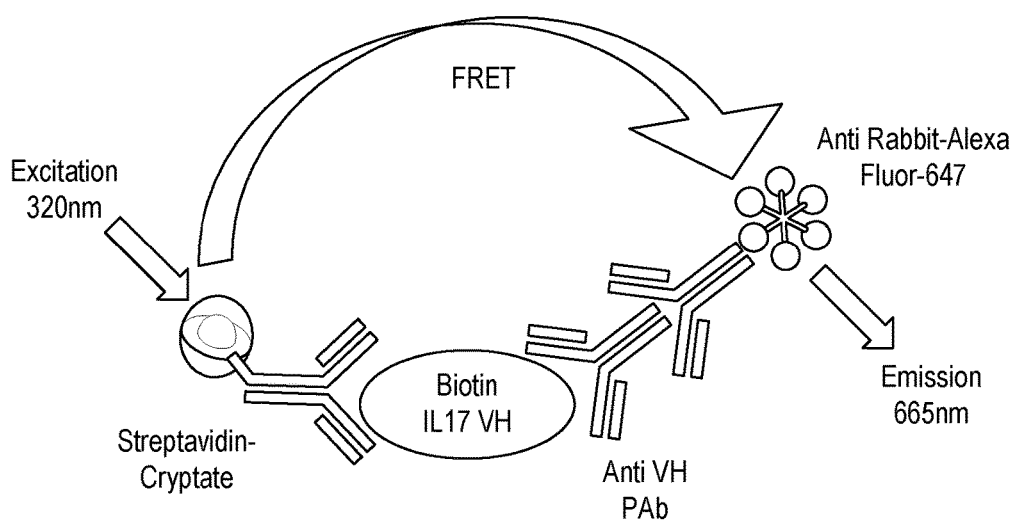

FIG. 6. Illustration of fluorescence Resonance Energy Transfer (FRET) Assay Principle.

Figure 7:
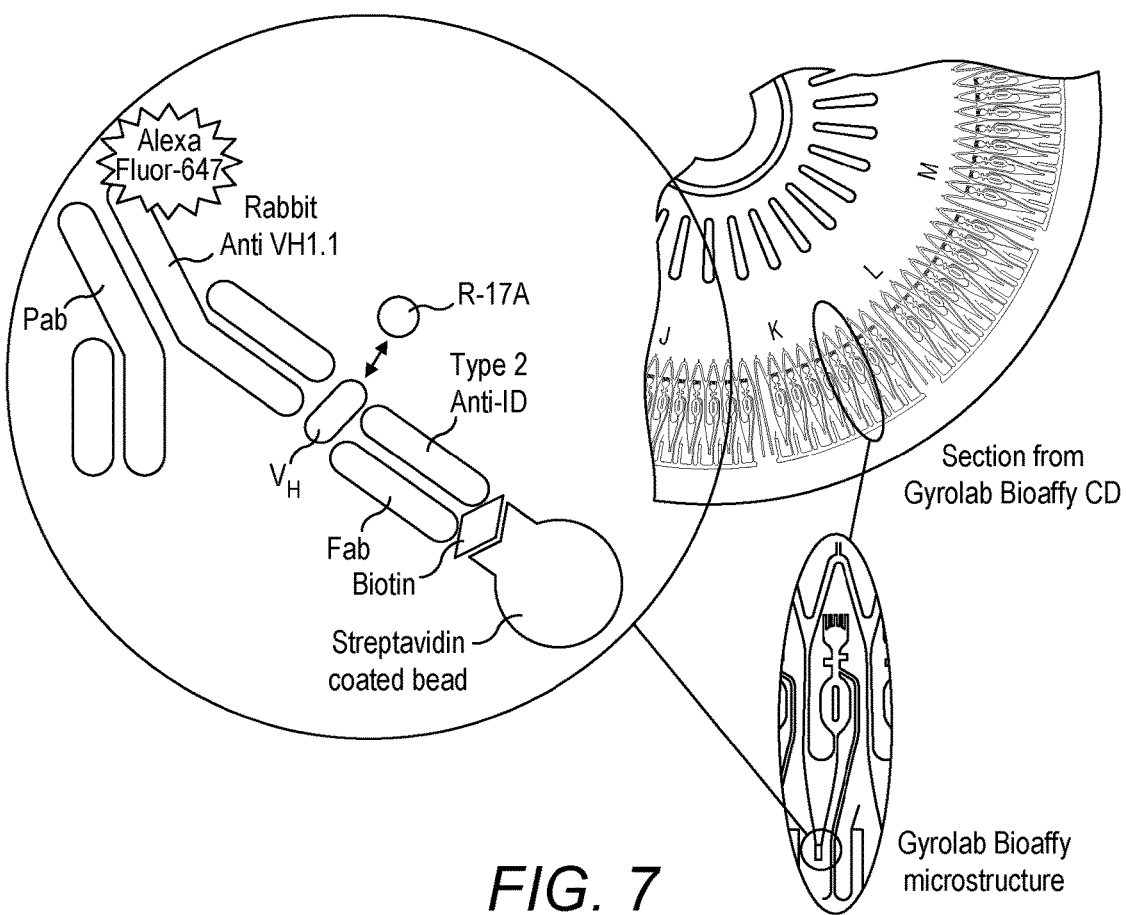

FIG. 7. Illustration of the Gyros $V_H$ 1.1 assay.

Figure 8:
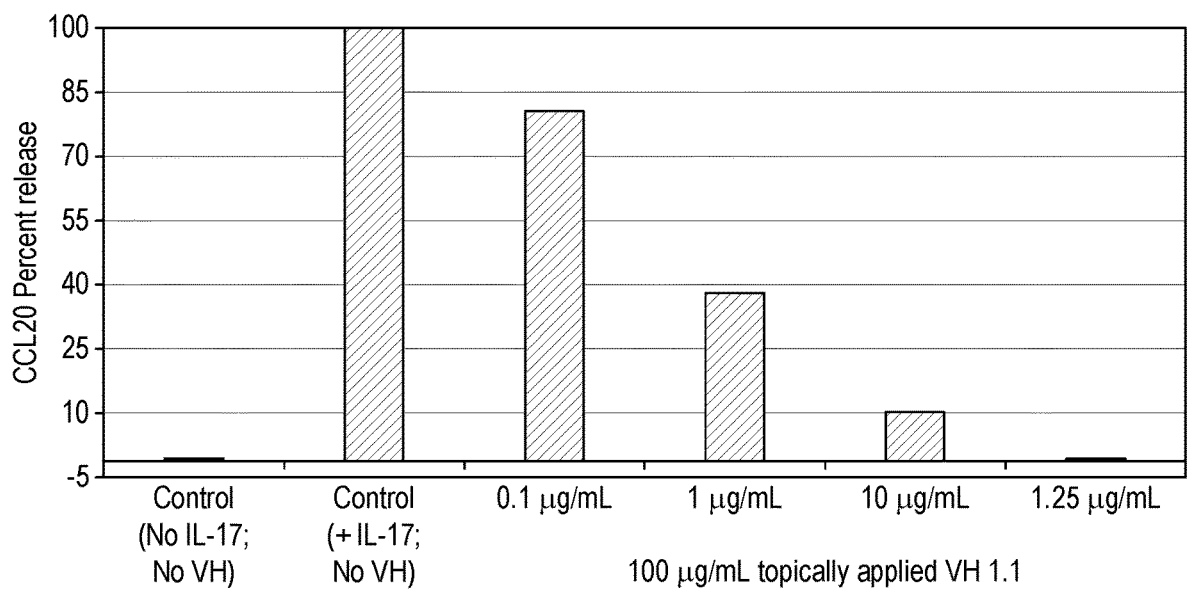

FIG. 8. CCL20 is inhibited by topical anti IL-17A $V_H$1.1 (SEQ ID NO: 74, 100 μl) in formulation (even at low dose) in an in vitro psoriatic model.

Figure 9:
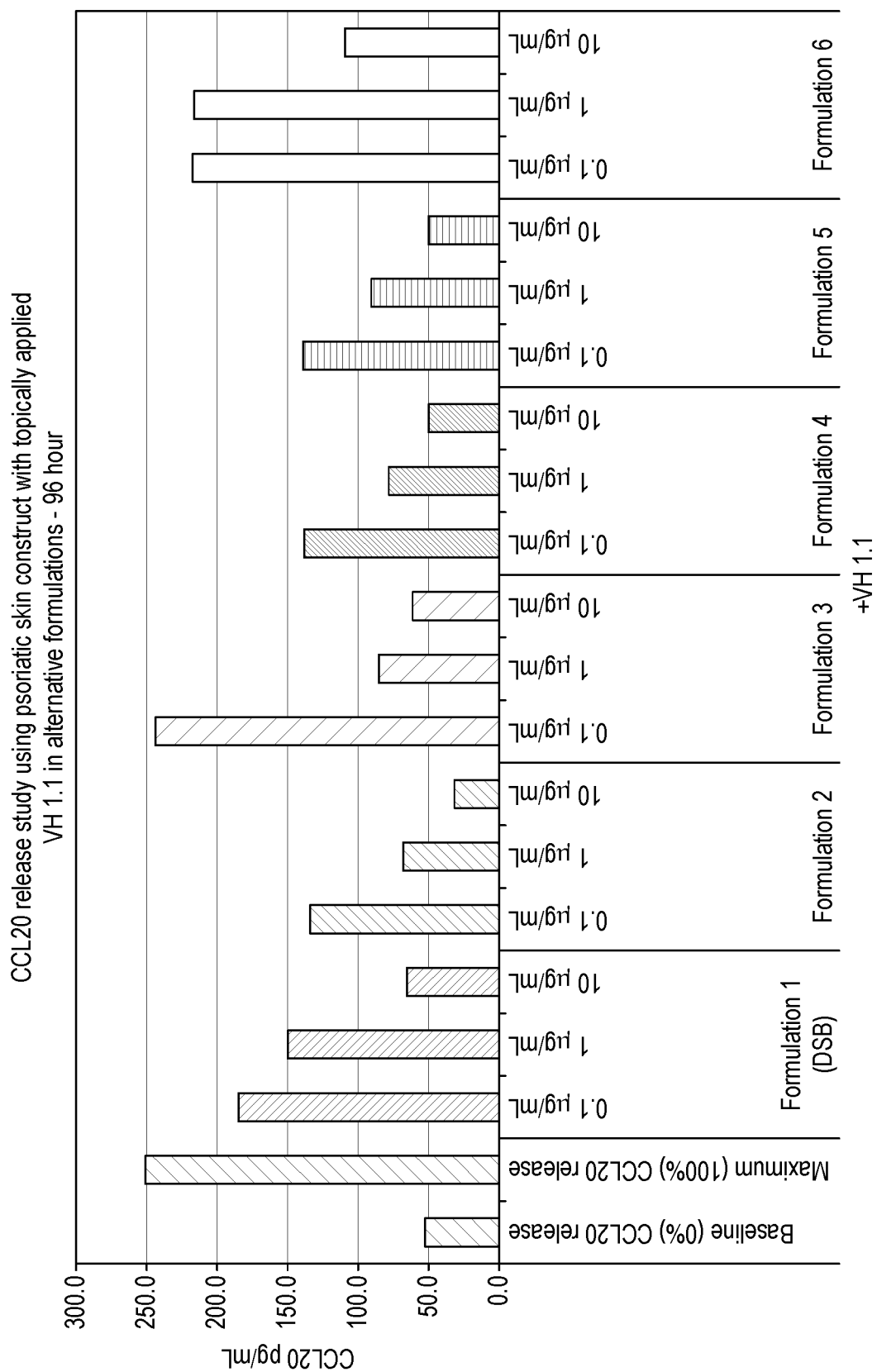

FIG. 9. CCL20 release study using psoriatic skin construct with topically applied $V_H$1.1 (SEQ ID NO: 74) in alternative formulations—96 hour. Formulations tested are as per tables 3 to 5.

Figure 10:
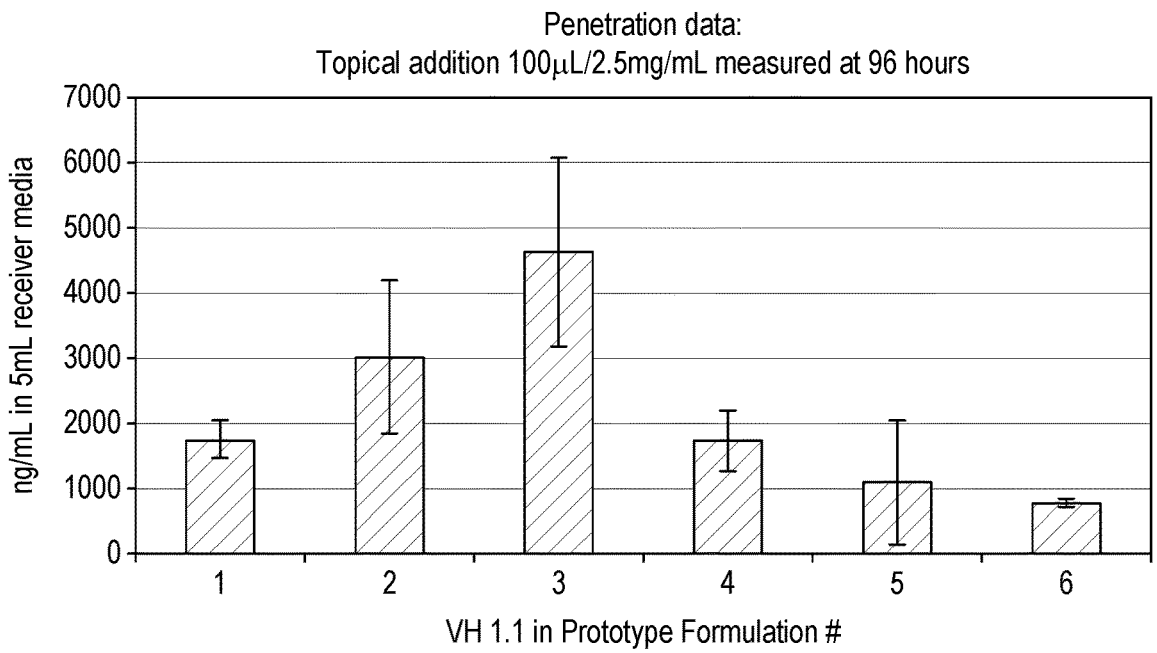

FIG. 10. Penetration of psoriatic tissue samples by anti IL-17A $V_H$1.1 (SEQ ID NO: 74) in alternative formulations using FRET analysis. Formulations tested are as per tables 3 to 5.

Figure 11:
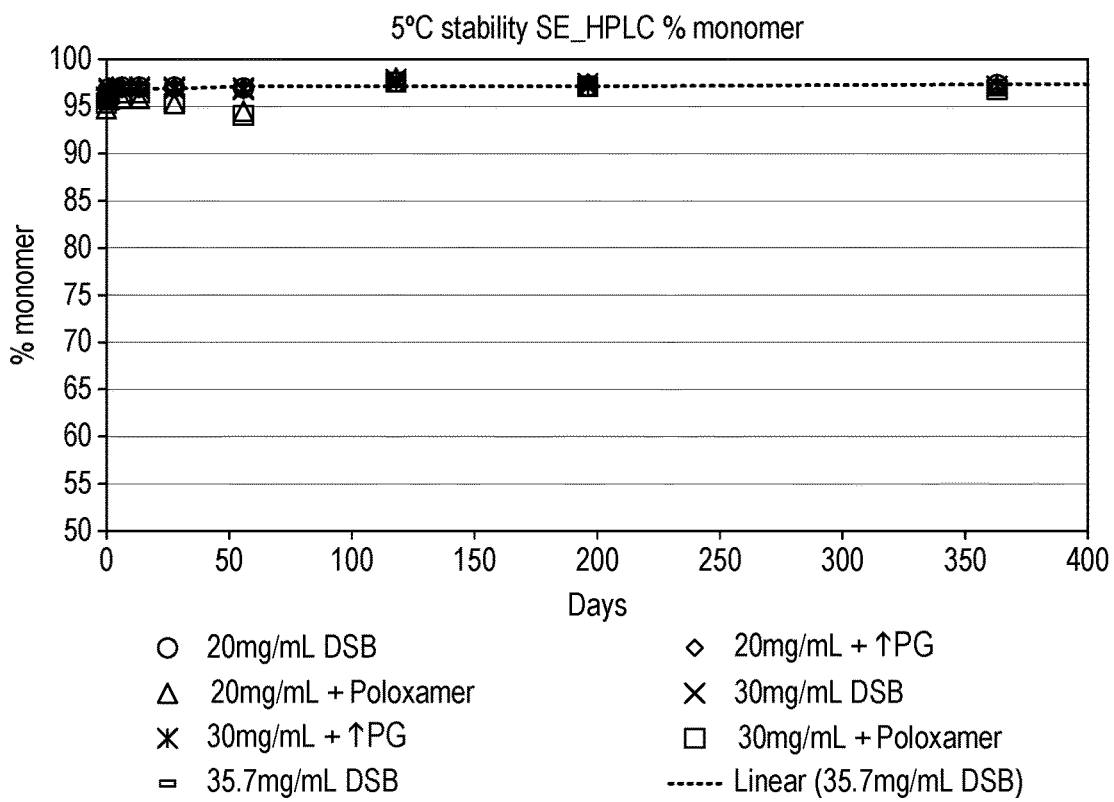

FIG. 11. Stability of Drug Substance formulation and additional formulations at 5° C. at 12 months. SE HPLC.

Figure 12:
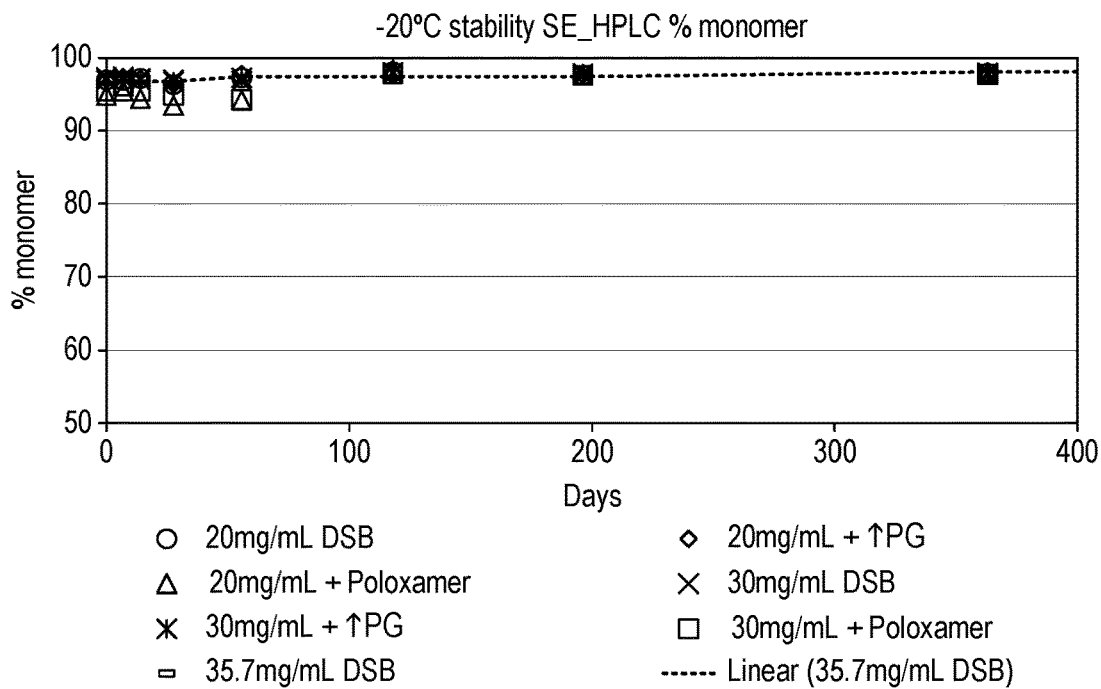

FIG. 12. Stability of Drug Substance formulation and additional formulations at −20° C. at 12 months. SE HPLC.

Figure 13:
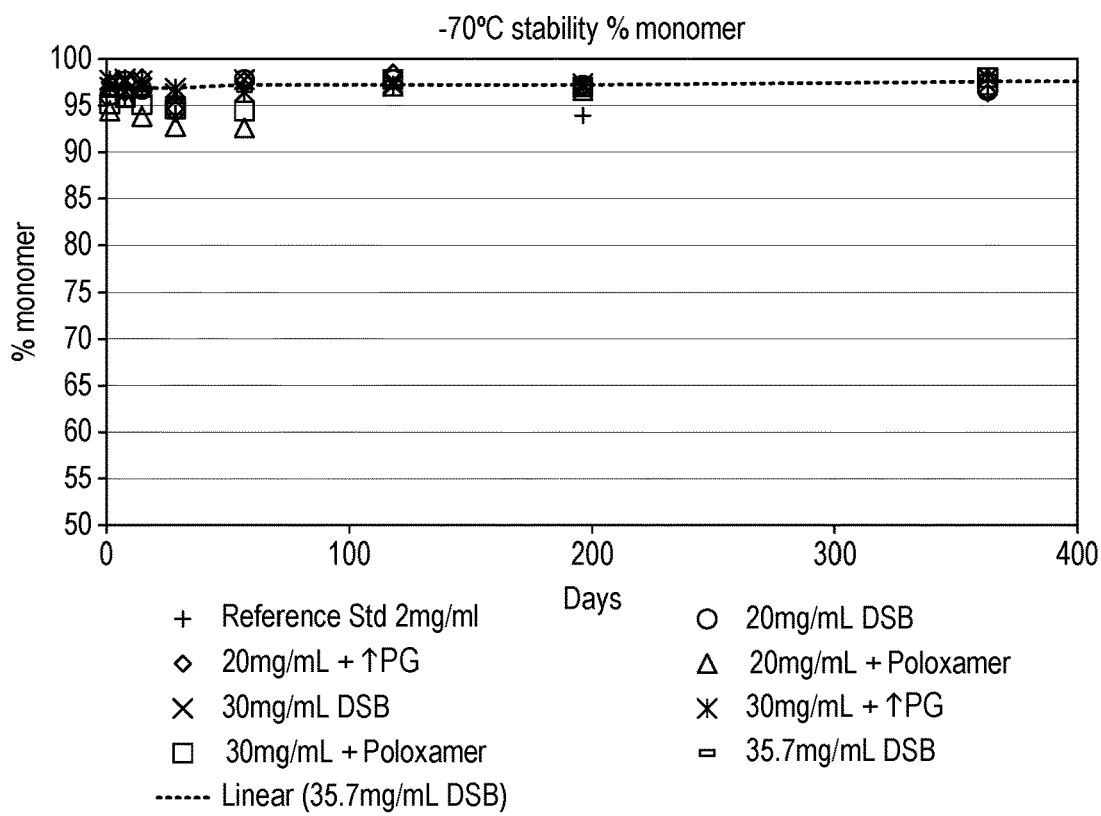

FIG. 13. Stability of Drug Substance formulation and additional formulations at −70° C. at 12 months using SE-HPLC.

Figure 14:
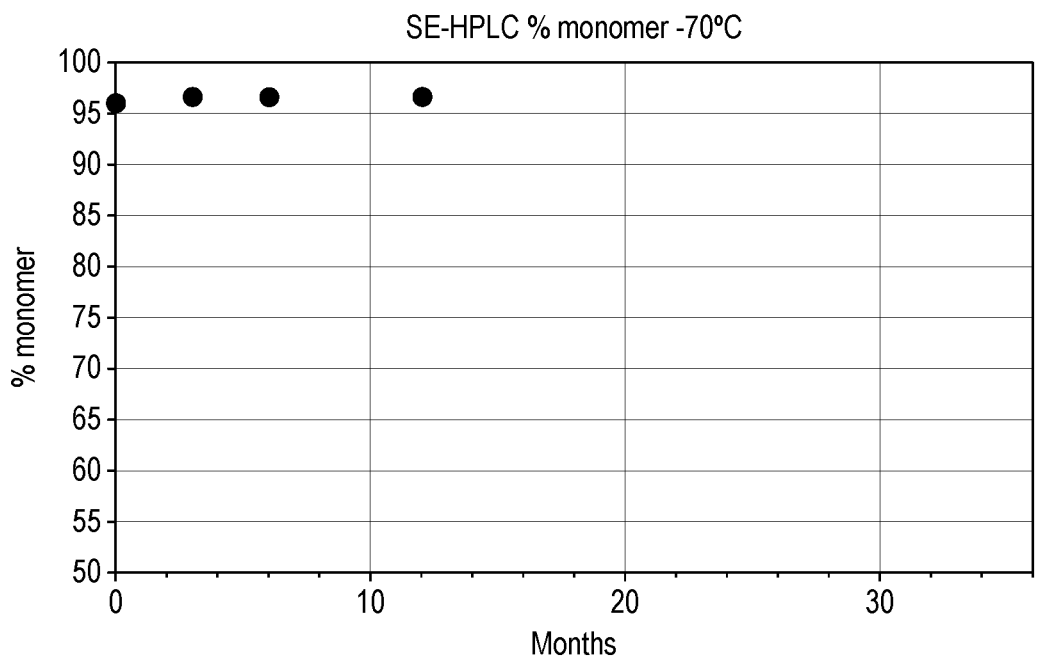

FIG. 14. 12 month data of stability study on bulk drug substance at −70° C. using SE-HPLC.

Figure 15:
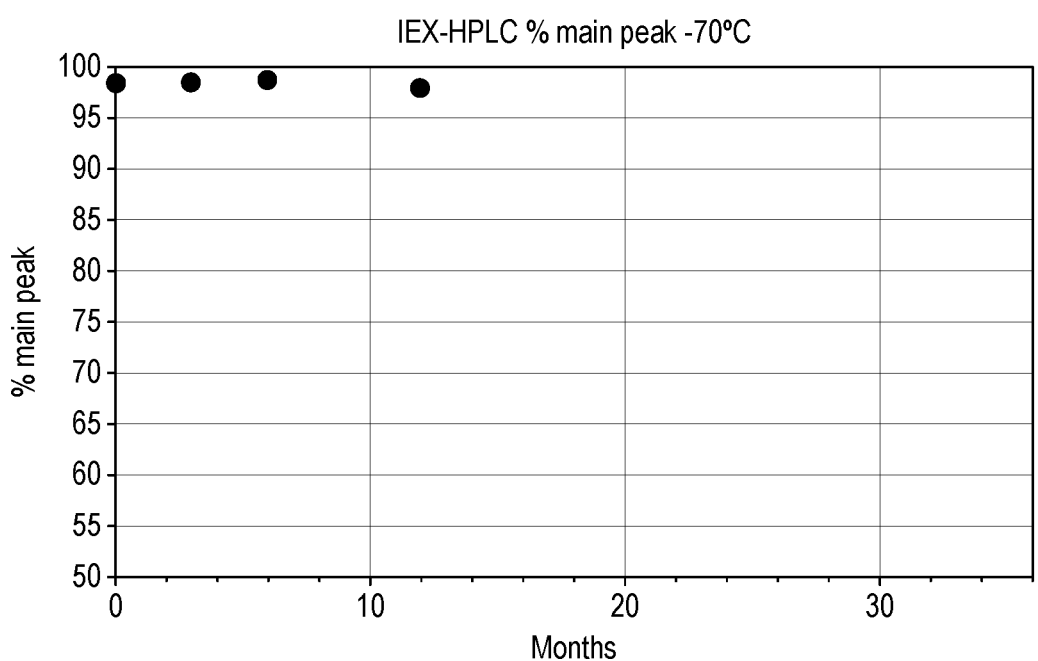

FIG. 15. 12 month data of stability study on bulk drug substance at −70° C. using IEX-HPLC.

Figure 16:
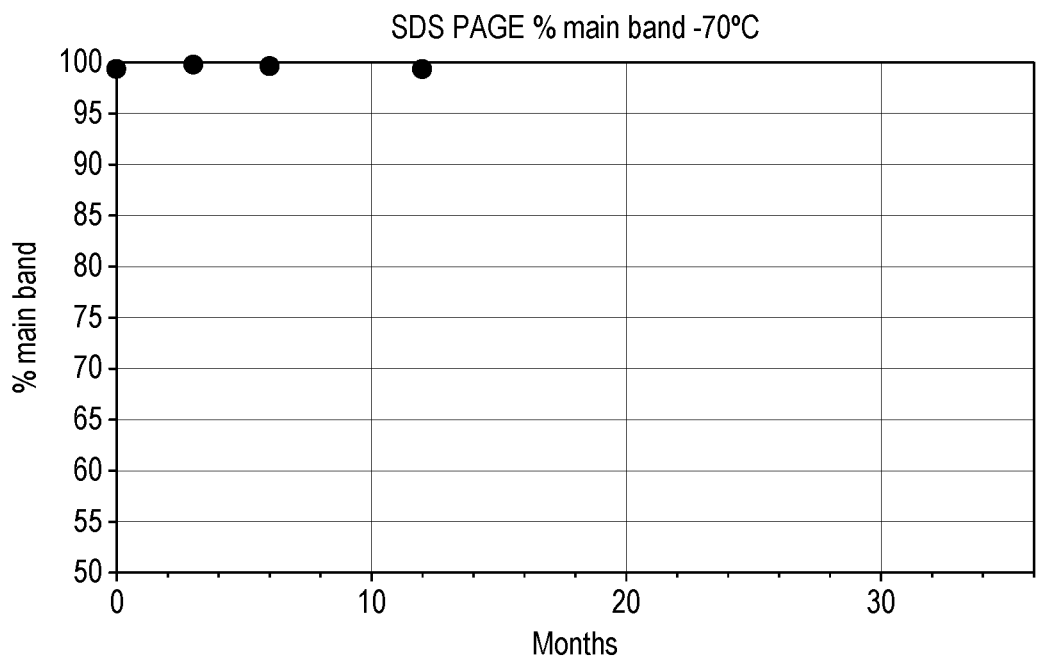

FIG. 16. 12 month data of stability study on bulk drug substance at −70° C. using SDS PAGE.

Figure 17:
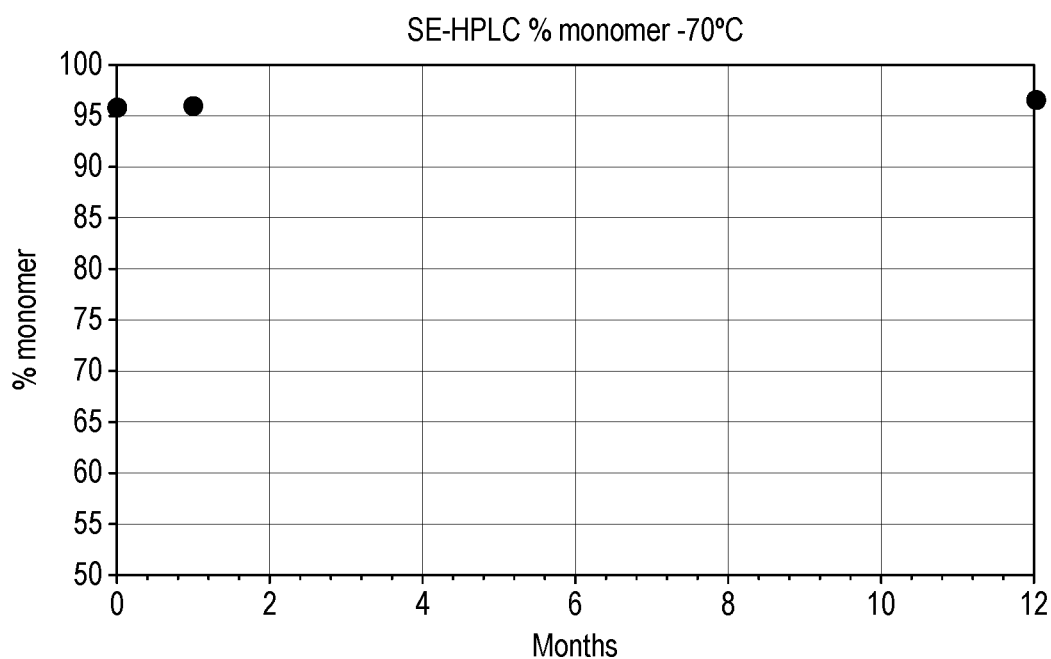

FIG. 17. 12 month data of stability study on bulk drug substance (formulation without PG) at −70° C. using SE-HPLC.

Figure 18:
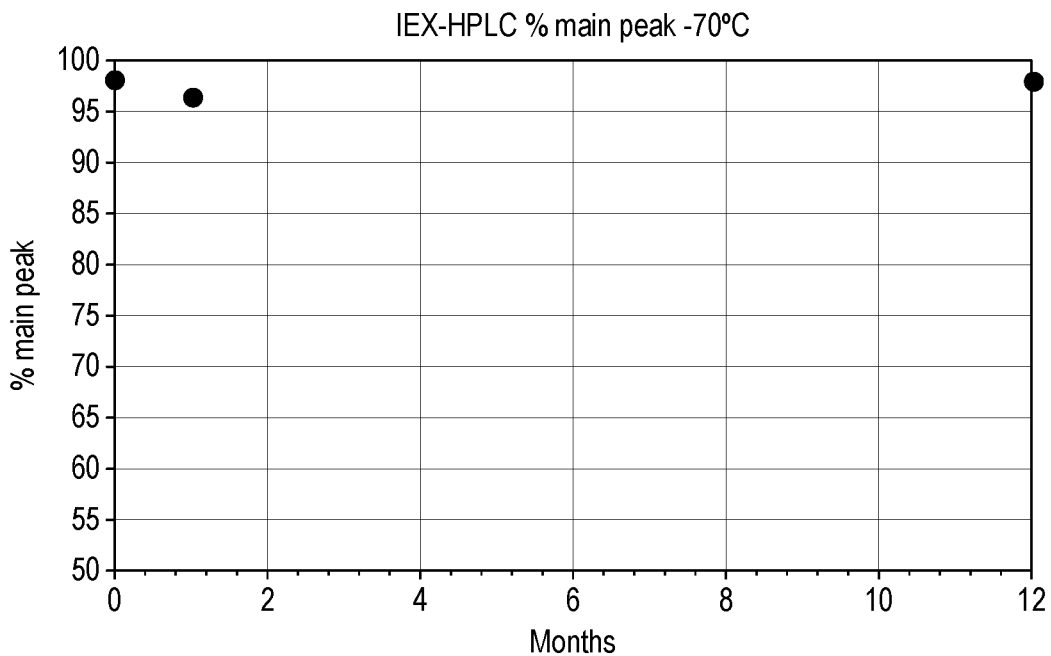

FIG. 18. 12 month data of stability study on bulk drug substance (formulation without PG) at −70° C. using IEX-HPLC.

Figure 19:
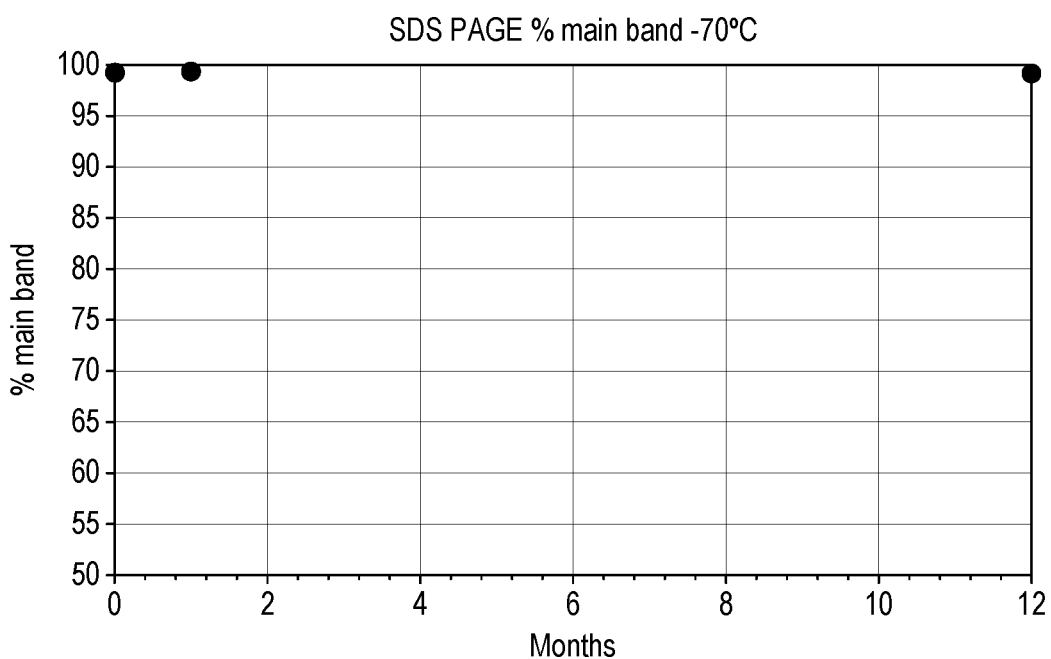

FIG. 19. 12 month data of stability study on bulk drug substance (formulation without PG) at −70° C. using SDS PAGE.

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Generally, nomenclatures used in connection with, and techniques of, cell and tissue culture, pathology, oncology, molecular biology, immunology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated. See, e.g., Sambrook et al., Molecular Cloning: A Laboratory Manual (4th ed., Cold Spring Harbor Laboratory Press, Cold Spring Harbor, N.Y. (2012)). Enzymatic reactions and purification techniques are performed according to the manufacturer's specifications, as commonly accomplished in the art or as described herein. The nomenclatures used in connection with, and the laboratory procedures and techniques of, analytical chemistry, synthetic organic chemistry, medicinal and pharmaceutical chemistry described herein are those well-known and commonly used in the art. Standard techniques are used for chemical syntheses, chemical analyses, pharmaceutical preparation, formulation, and delivery, and treatment of patients.

The inventors have demonstrated that isolated IL-17A binding molecules can be formulated for topical delivery using suitable excipients as described herein. The invention thus provides stable and non-aggregating compositions/formulations, in particular compositions and formulations suitable for topical delivery, comprising an IL-17A binding molecule. In one aspect, the invention provides such compositions formulated as freeze or spray dried compositions. These can be reconstituted for administration. In another aspect, the invention provides compositions that are formulated as a liquid, gel, cream, lotion, ointment or a vapour for powder inhalation or compositions that are administered using a plaster, patch or the like.

Thus, in one aspect, the invention provides a composition comprising
a) an effective amount of a binding molecule, for example at least one single domain antibody, capable of binding human IL-17A and
b) 10-150 mM Tris/glycine wherein the pH of said composition is about 5 to about 9.

As further explained herein, in one embodiment, the IL-17A binding molecule is preferably selected from a single domain antibody (sdAb). In one embodiment, the single domain antibody is a single variable domain antibody. In one embodiment, the single variable domain is a heavy chain variable domain. In one embodiment, the IL-17A binding molecule is selected from at least one single domain antibody comprising a $V_H$ or $V_{HH}$ domain capable of binding human IL-17A ('a $V_H$ or $V_{HH}$ single domain antibody'). $V_H$ domains are generally understood to designate human variable heavy chain domains. $V_{HH}$ domains are generally understood to designate camelid variable heavy chain domains.

In one embodiment of the compositions of the invention, the composition comprises an effective amount of at least one single domain antibody comprising a $V_H$ domain capable of binding human IL-17A wherein said $V_H$ domain has a sequence comprising a CDR3 sequence having the amino acid residues GEILPLYFDY (SEQ ID NO:4) or sequence comprising a CDR3 with a sequence having at least 80%, for example at least 90%, 91%, 92%, 93%, 94%, 95%, 96%, 97%, 98% or 99% homology to SEQ ID NO:4. In one embodiment, said CDR3 sequence is a variant of SEQ ID NO:4 and comprises substitutions, insertions, additions or deletions of one or more amino acid residue of said SEQ ID NO:4.

In one embodiment, said $V_H$ domain comprises a CDR1 having the amino acid residues SYSMY (SEQ ID NO: 2) or a sequence with a sequence with 1, 2, 3, 4 or 5 amino acid modifications. In one embodiment, said CDR1 sequence is a variant of SEQ ID NO:2 and comprises substitutions, insertions, additions or deletions of one or more amino acid residue of said SEQ ID NO:2.

In one embodiment, said $V_H$ domain comprises a CDR2 having the amino acid residues EIKQDGSVQYYVSDVKG (SEQ ID NO. 3) or a sequence with at least 80%, for example at least 90%, 91%, 92%, 93%, 94%, 95%, 96%, 97%, 98% or 99% homology to SEQ ID NO:3. In one embodiment, said CDR2 sequence is a variant of SEQ ID NO:3 and comprises substitutions, additions, insertions or deletions of one or more amino acid residue of said SEQ ID NO:3.

In one embodiment, the $V_H$ domain has a CDR1, CDR2 and CDR3, wherein said CDR1 has SEQ ID NO:2 or a variant thereof that comprises substitutions, additions or deletions of one or more amino acid residue, said CDR2 has SEQ ID NO:3 or a variant thereof that comprises substitutions additions, insertions or deletions of one or more amino acid residue and said CDR3 has SEQ ID NO:4 or a variant thereof that comprises substitutions additions, insertions or deletions of one or more amino acid residue. In one embodiment, the $V_H$ domain has a CDR1, CDR2 and CDR3, wherein said CDR1 has SEQ ID NO:2, said CDR2 has SEQ ID NO:3 and said CDR3 has SEQ ID NO:4.

In another embodiment, said $V_H$ domain comprises or consists of SEQ ID NO:1 or a sequence having at least 50%, 55%, 60%, 65%, 70% or 75% homology thereto. SEQ ID NO: 1 is shown below:

```
(CDR1, 2 and 3 in bold and underlined)
                                         SEQ ID NO: 1
EVQLVESGGGLVQPGGSLRLSCAASGFTFSSYSMYWVRQAPGKGLEWVA
EIKQDGSVQYYVSDVKGRFTISRDNAKNSLYLQMNSLRAEDTAVYYCAK
GEILPLYFDYWGQGTLVTVSS
```

As will be further explained herein, in one aspect, one or more optional excipient can be added to the composition described above, in particular for topical delivery. Topical delivery is used herein to describe administration to a particular spot of the body and includes administration to the surface of the body as well as pulmonary administration by topical agents. Topical administration can be to the skin, eye, gums, a membrane or lung. In a second aspect, a composition of the invention described above can be freeze or spray dried with one or more optional excipient. Such compositions may be reconstituted with one or more excipient suitable for topical delivery prior to administration.

Throughout the present disclosure, all expressions of percentage, ratio, and the like are "by weight" unless otherwise indicated. As used herein, "by weight" is synonymous with the term "by mass," and indicates that a ratio or percentage defined herein is done according to weight rather than volume, thickness, or some other measure.

The invention relates to formulations and compositions that are pharmaceutical compositions and formulations. As used herein, the terms "formulation" or "composition" describe the active molecule in combination with a pharmaceutically acceptable excipient. The terms "pharmaceutical composition" or "pharmaceutical formulation" refer to preparations which are in such form as to permit the biological activity of the active ingredients to be effective. The term "pharmaceutically acceptable" refers to a compound or protein that can be administered to an animal (for example, a mammal) without significant adverse medical consequences.

The IL-17 family of cytokines includes six members, IL-17/IL-17A, IL-17B, IL-17C, IL-17D, IL-17E/IL-25, and IL-17F, which are produced by multiple cell types. Members of this family have a highly conserved C-terminus containing a cysteine-knot fold structure. Most IL-17 proteins are secreted as disulfide-linked dimers, with the exception of IL-17B, which is secreted as a non-covalent homodimer.

Signaling by IL-17 family cytokines is mediated by members of the IL-17 receptor family, IL-17 R/IL-17 RA, IL-17 B R/IL-17 RB, IL-17 RC, IL-17 RD, and IL-17 RE.

Activation of these receptors triggers intracellular pathways that induce the production of pro-inflammatory cytokines and anti-microbial peptides. IL-17A, IL-17F, and IL-17A/F are produced primarily by activated T cells and signal through an oligomerized receptor complex consisting of IL-17 RA and IL-17 RC. Ligand binding to this complex leads to recruitment of the intracellular adaptor proteins, Act1 and TRAF-6, and downstream activation of the transcription factors, NF kappa B, AP-1, and C/EBP. IL-17E activates similar signaling pathways through a receptor complex formed by IL-17 RA and IL-17 B R/IL-17RB. Signaling by IL-17E induces Th2-type immune responses and may be involved in promoting the pathogenesis of asthma. Less is known about the signaling pathways activated by other IL-17 family cytokines. Recent studies suggest that IL-17C is produced primarily by epithelial cells and binds to a receptor complex consisting of IL-17 RA and IL-17 RE. Autocrine signaling by IL-17C in epithelial cells stimulates the production of anti-microbial peptides and pro-inflammatory cytokines, but like IL-17A, overexpression of IL-17C may contribute to the development of autoimmune diseases. Similar to IL-17E, IL-17B binds to IL-17 B R/IL-17 RB, but the major target cells and effects of IL-17B signaling have not been reported. In addition, the receptor for IL-17D and the ligand for IL-17 RD are currently unknown.

An IL-17A binding molecule as used herein binds to human IL-17A (Accession number Q16552 (Swiss-Prot) showing the full-length precursor IL-17A including the signal peptide, SEQ ID NO:75) and/or cynomolgus monkey IL-17 (Uniprot G7P4U9). Human IL-17A is a homodimer consisting of two 155 amino acid chains. Each polypeptide chain includes a 23 amino acid N-terminal peptide which is cleaved to produce a mature polypeptide of 132 residues. IL-17A binds to and exerts its effects via activation of the IL-17 receptors A and C.

SEQ ID NO: 75
MTPGKTSLVSLLLLLSLEAIVKAGITIPRNPGCPNSEDKNFPRTVMVNL

NIHNRNTNTNPKRSSDYYNRSTSPWNLHRNEDPERYPSVIWEAKCRHLG

CINADGNVDYHMNSVPIQQEILVLRREPPHCPNSFRLEKILVSVGCTCV

TPIVHHVA

The terms "IL-17 binding molecule", "anti-IL-17 binding molecule" "IL-17 binding protein" "anti-IL-17 single domain antibody" or "anti-IL-17 antibody" all refer to a molecule capable of binding to the human IL-17A antigen. Thus, as used herein, IL-17 usually refers to IL-17A, unless otherwise stated or unless the context directs otherwise. The binding reaction may be shown by standard methods (qualitative assays) including, for example, a binding assay, competition assay or a bioassay for determining the inhibition of IL-17 binding to its receptor or any kind of binding assays, with reference to a negative control test in which an antibody of unrelated specificity. The term "IL-17 binding molecule" includes an IL-17 binding protein or a part thereof that is capable of binding human IL-17A. In preferred embodiments, the IL-17 binding molecule is an antibody or fragment thereof, for example an anti-IL-17 single domain antibody. In a more preferred embodiment, the IL-17 binding molecule is an anti-IL-17 single domain antibody comprising a $V_H$ domain as described herein.

The term "antibody", broadly refers to any immunoglobulin (Ig) molecule, or antigen binding portion thereof, comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. In a full-length antibody, each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity-determining regions (CDR), interspersed with regions that are more conserved, termed framework regions (FR). Each $V_H$ and $V_L$ is composed of three CDRs and four FRs, arranged from amino-terminus to carboxy terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "CDR" refers to the complementarity determining region within antibody variable sequences. There are three CDRs in each of the variable regions of the heavy chain and the light chain, which are designated CDR1, CDR2 and CDR3, for each of the variable regions.

The term "CDR set" refers to a group of three CDRs that occur in a single variable region capable of binding the antigen. The exact boundaries of these CDRs have been defined differently according to different systems. The system described by Kabat is used herein. The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al., (1971) Ann. NY Acad. Sci. 190:382-391 and Kabat, et al., (1991) Sequences of Proteins of Immunological Interest, Fifth Edition, U.S. Department of Health and Human Services, NIH Publication No. 91-3242).

The term "antigen binding site" refers to the part of the antibody or antibody fragment that comprises the area that specifically binds to an antigen. An antigen binding site may be provided by one or more antibody variable domains. Preferably, an antigen binding site is comprised within the associated $V_H$ and $V_L$ of an antibody or antibody fragment.

An antibody fragment is a portion of an antibody, for example as F(ab')$_2$, Fab, Fv, sFv and the like. Functional fragments of a full length antibody retain the target specificity of a full length antibody. Recombinant functional antibody fragments, such as Fab (Fragment, antibody), scFv (single chain variable chain fragments) and single domain antibodies (dAbs) have therefore been used to develop therapeutics as an alternative to therapeutics based on mAbs.

scFv fragments (~25 kDa) consist of the two variable domains, $V_H$ and $V_L$. Naturally, $V_H$ and $V_L$ domain are non-covalently associated via hydrophobic interaction and tend to dissociate. However, stable fragments can be engineered by linking the domains with a hydrophilic flexible linker to create a single chain Fv (scFv).

The smallest antigen binding fragment is the single variable fragment, namely the $V_H$ or $V_L$ domain. Binding to a light chain/heavy chain partner respectively is not required for target binding. Such fragments are used in single domain antibodies. A single domain antibody (~12 to 15 kDa) therefore consists of or comprises either the $V_H$ or $V_L$ domain.

The terms "single domain antibody, variable single domain or immunoglobulin single variable domain (ISV)" are all well known in the art and describe the single variable fragment of an antibody that binds to a target antigen. These terms are used interchangeably herein. As explained below, in preferred embodiments of the various aspects of the invention, the single variable domain may be a domain antibody ("dAb") or an amino acid sequence that is suitable for use as a domain antibody, a single domain antibody (or an amino acid sequence that is suitable for use as a single domain antibody) other single variable domains, or any suitable fragment of any one thereof. Single domain antibodies have been described in the art; they are antibodies whose complementary-determining regions are part of a single domain polypeptide, for example a variable domain, such as a human heavy chain variable domain ($V_H$) polypeptide. Single variable domain antibodies wherein the variable domain is a $V_{HH}$ domain are also within the scope of the invention. For a general description of (single) domain antibodies, reference is also made to Ward et al. 1989 (Nature 341 (6242): 544-546) and to Holt et al. 2003 (Trends Biotechnol. 21(11): 484-490).

In one embodiment, the binding molecules of the invention comprise a single variable domain antibody wherein said variable domain is a $V_H$ domain. Such molecules are termed $V_H$ single domain antibody or single $V_H$ domain antibody. Human heavy chain variable domain antibodies are particularly preferred. Binding molecules that comprise a single variable domain antibody wherein said domain is a human $V_H$ domain are also termed Humabody® $V_H$ herein. Thus, in one embodiment, the IL-17A binding molecule is a Humabody® $V_H$. Humabody® is a registered trademark of Crescendo Biologics Ltd.

As used herein, the term $V_H$ or "variable domain" refers to immunoglobulin variable domains defined by Kabat et al. (1991). The numbering and positioning of CDR amino acid residues as used herein is in accordance with the well-known Kabat numbering convention.

In one embodiment, the isolated binding molecules used in the formulation and other aspects of the invention comprise or consist of at least one single domain antibody wherein said domain is a human $V_H$ domain. Thus, in one aspect, the binding molecules of the invention comprise or consist of at least one immunoglobulin single variable heavy chain domain antibody that has a $V_H$ domain, but is devoid of $V_L$ domains.

Each single $V_H$ domain antibody comprises three CDRs and four FRs, arranged from amino-terminus to carboxy-terminus in the following order: FR1-CDR1-FR2-CDR2-FR3-CDR3-FR4. Thus, in one embodiment of the invention, the domain is a $V_H$ domain with the following formula FR1-CDR1-FR2-CDR2-FR3-CDR3-FR4.

IL17A binding molecules including single domain antibodies used in the compositions according to the invention are isolated molecules. The term "isolated" single domain antibody refers to a single domain antibody that is substantially free of other single domain antibodies, antibodies or antibody fragments having different antigenic specificities. Moreover, an isolated single domain antibody may be substantially free of other cellular material and/or chemicals.

As explained further herein, in preferred embodiments, the single $V_H$ domain antibodies are generated in transgenic mice that express human V, D and J regions are used according to the invention.

According to the various aspects and embodiments of the invention, the variable domain of the single domain antibodies of the invention is preferably a human variable domain (human variable domains are typically termed $V_H$). As used herein, a human $V_H$ domain includes a fully human or substantially fully human $V_H$ domain. As used herein, the term human $V_H$ domain also includes $V_H$ domains that are isolated from heavy chain only antibodies made by transgenic mice expressing fully human immunoglobulin heavy chain loci, in particular in response to an immunisation with an antigen of interest, for example as described in WO2016/062990 and in the examples. In one embodiment, a human $V_H$ domain can also include a $V_H$ domain that is derived from or based on a human $V_H$ domain amino acid or nucleic acid sequence encoding such $V_H$ domain. Thus, the term includes variable heavy chain regions derived from or encoded by human germline immunoglobulin sequences. A substantially human $V_H$ domain or $V_H$ domain that is derived from or based on a human $V_H$ domain may include amino acid residues not encoded by human germline immunoglobulin sequences (e.g., mutations introduced in vitro, e.g. by random or site-specific mutagenesis, or introduced by somatic mutation in vivo). The term "human $V_H$ domain" therefore also includes a substantially human $V_H$ domain wherein one or more amino acid residue has been modified. For example, a substantially human $V_H$ domain may include up to 10, for example 1, 2, 3, 4 or 5 amino acid modifications compared to a fully human sequence.

However, the term "human $V_H$ domain" or "substantially human $V_H$ domain", as used herein, is not intended to include antibodies in which CDR sequences derived from the germline of another mammalian species, such as a mouse, have been grafted onto human framework sequences. In some embodiments, the term "human $V_H$ domain", as used herein, does not include camelized $V_H$ domains, that is human $V_H$ domains that have been specifically modified, for example in vitro by conventional mutagenesis methods to select predetermined positions in the $V_H$ domains sequence and introduce one or more point mutation at the predetermined position to change one or more predetermined residue to a specific residue that can be found in a camelid $V_{HH}$ domain.

Thus, in one embodiment, the IL-17A binding molecule is selected from at least one single domain antibody comprising a human $V_H$ domain capable of binding human IL-17A. In one embodiment, the IL-17A binding molecule is selected from at least one single $V_H$ domain antibody capable of binding human IL-17A. In another embodiment, the $V_H$ domain comprises or consists of SEQ ID NO: 1 or a sequence having at least 50%, 55%, 60%, 65%, 70% or 75% homology thereto.

Modifications to the $V_H$ framework may be made to improve binding and/or other properties. For example, the $V_H$ domain may comprise C or N terminal extensions.

"Homology" generally refers to the percentage of amino acid residues in the candidate sequence that are identical with the residues of the polypeptide with which it is compared, after aligning the sequences and in some embodiments after introducing gaps, if necessary, to achieve the maximum percent homology, and not considering any conservative substitutions as part of the sequence identity. Neither N- or C-terminal extensions, tags or insertions shall be construed as reducing identity or homology. Methods and computer programs for the alignment are well known.

As set out herein, in one embodiment, the compositions of the invention comprise an effective amount of at least one single $V_H$ domain antibody capable of binding human IL-17A wherein said $V_H$ domain comprises SEQ ID NO: 1 or a sequence having at least 50%, 55%, 60%, 65%, 70% or 75% homology thereto. In one embodiment, said sequence homology or identity is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

In some embodiments, the invention provides a single $V_H$ domain antibody that is a variant of the single $V_H$ domain antibody as defined in SEQ ID NO:1 having one or more amino acid modifications compared to SEQ ID NO:1 and which retains a biological function of the single domain antibody. The modification can be one or more substitution, deletion, insertion or other addition of an amino acid residue. Variants can be selected from SEQ ID NOs: 5 to 73 as shown in Table 1.

In one embodiment, a variant single $V_H$ domain antibody can be sequence engineered. Modifications include at least one substitution, deletion or insertion of one or more codons encoding the single domain antibody or polypeptide that results in a change in the amino acid sequence as compared with the native sequence $V_H$ single domain antibody or polypeptide. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 10, for example 1, 2, 3, 4, 5, 6, 7, 8, 9 or 10 amino acids. The variation allowed may be determined by systematically making insertions, deletions or substitutions of amino acids in the sequence and testing the resulting variants for activity exhibited by the full-length or mature native sequence. A variant of the $V_H$ single domain antibody defined in SEQ ID NO: 1 has preferably at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence homology to the non-variant molecule, preferably at least 95%, 96%, 97%, 98% or 99% sequence homology.

In one embodiment, the modification is a conservative sequence modification. As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of a single domain antibody of the invention can be replaced with other amino acid residues from the same side chain family and the altered antibody can be tested for retained function (i.e., the functions set forth in (c) through (I) above) using the functional assays described herein.

In some embodiments, the invention provides a variant of $V_H$ single domain antibody as defined in SEQ ID NO:1 that comprises one or more sequence modification and has improvements in one or more of a property such as binding affinity, specificity, thermostability, expression level, effector function, glycosylation, reduced immunogenicity, or solubility as compared to the unmodified single domain antibody.

In one embodiment, modifications can be made to decrease the immunogenicity of the single domain antibody. For example, one approach is to revert one or more framework residues to the corresponding human germline sequence. More specifically, a single domain antibody that has undergone somatic mutation may contain framework residues that differ from the germline sequence from which the single domain antibody is derived. Such residues can be identified by comparing the single domain antibody framework sequences to the germline sequences from which the single domain antibody is derived.

To return one or more of the amino acid residues in the framework region sequences to their germline configuration, the somatic mutations can be "backmutated" to the germline sequence by, for example, site-directed mutagenesis or PCR-mediated mutagenesis.

Another type of framework modification involves mutating one or more residues within the framework region, or even within one or more CDR regions, to remove T cell epitopes to thereby reduce the potential immunogenicity of the antibody.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

A skilled person will know that there are different ways to identify, obtain and optimise the antigen binding molecules as described herein, including in vitro and in vivo expression libraries. This is further described in the examples. Optimisation techniques known in the art, such as display (e.g., ribosome and/or phage display) and/or mutagenesis (e.g., error-prone mutagenesis) can be used. The invention therefore also comprises sequence optimised variants of the single domain antibodies described herein.

In one embodiment, the $V_H$ domain comprises or consists of SEQ ID NO:1, but comprises one or more amino acid substitutions, for example 1, 2, 3, 4, 5, 6, 7, 8, 9 or 10 amino acid substitutions. In one embodiment, the one or more amino acid substitution is in one or more of the framework areas, for example FR1, FR2, FR3 and/or FR4. In another embodiment, the one or more amino acid substitution is in one or more of the CDRs. In another embodiment, the $V_H$ domain comprises or consists of SEQ ID NO:1, but comprises 1, 2, 3, 4 or 5 amino acid substitutions in a CDR sequences, for example a CDR1, CDR2 or CDR3. For example, in CDR3 (SEQ ID NO:4) of SEQ ID NO:1 or a variant thereof, one or more Y may be replaced with H.

In one embodiment, the $V_H$ single domain antibody is selected from one of the amino acid sequences shown below in Table 1 (Table 1 shows the full length $V_H$ amino acid sequence; sequences for FR1, CDR1, FR2, CDR2, FR3, CDR3 and FR4 respectively are shown in the separate columns of Table 1 for ease of reference).

TABLE 1

| SEQ ID NO of full length VH | FR1 | CDR1 | FR2 | CDR2 | FR3 | CDR3 | FR4 |
|---|---|---|---|---|---|---|---|
| 5 | EVQLVESGGGLVQPGGSLRLSCAASGFTFS | SYSMY | WVRQAPGKGLEWVA | NIKQDGSEKYYVDSVKG | RFTISRDNAKNSLFLQMNSLRAEDTAVYYCAK | GEILPLHFDY | WGQGTLVTVSS |
| 6 | EVQLVESGGGLVQPGGSLRLSCAASGFTFS | SYSMY | WVRQAPGKGLEWVA | EIKQDGSVQYYVDSVKG | RFTISRDNAKNSLYLQMNSLRAEDTAVYYCAK | GEILPLYFDY | WGQGTLVTVSS |
| 7 | EVQLVESGGGLVQPGGSLRLSCAASGFTFS | SYSMY | WVRQAPGKGLEWVA | EIKQTGSVQYYVDSVKG | RFTISRDNAKNSLYLQMNSLRAEDTAVYYCAK | GEILPLYFDY | WGQGTLVTVSS |
| 8 | EVQLVESGGGLVQPGGSLRLSCAASGFTFS | SYSMY | WVRQAPGKGLEWVA | EIKPTGSVQYYVDSVKG | RFTISRDNAKNSLYLQMNSLRAEDTAVYYCAK | GEILPLYFDY | WGQGTLVTVSS |
| 9 | EVQLVESGGGLVQPGGSLRLSCAASGFTFS | SYSMY | WVRQAPGKGLEWVA | EIKQDGSEQYYVDSVKG | RFTISRDNAKNSLYLQMNSLRAEDTAVYYCAK | GEILPLYFDY | WGQGTLVTVSS |
| 10 | QVQLVESGGGLVQPGGSLRLSCAASGFTFS | SYGMY | WVRQAPGKGLEWVA | KIEQDGSEEYYVDSVKG | RFTISRDNAKKSLYLQMNSLRAEDTAVYYCAK | GEILPLYFDY | WGQGTLVTVSS |
| 11 | QVQLVESGGGLVQPGGSLRLSCAASGFTFS | SYGMY | WVRQAPGKGLEWVA | KIEQDGSEKYYVDSVKG | RFTISRDNAKNSLFLQMNSLRAEDTAVYYCAK | GEILPLYFDY | WGQGTLVTVSS |
| 12 | QVQLVESGGGLVQPGGSLRLSCAASGFTFS | SYGMY | WVRQAPGKGLEWVA | EIKQDGSEKYYVDSVKG | RFTISRDNAKNSLYLQMNSLRAEDTAVYYCAK | GEILPLYFDY | WGQGTLVTVSS |
| 13 | EVQLVESGGGLVQPGGSLRLSCAASGFTFS | SYRMY | WVRQAPGKGLEWVA | SIEQDGSEEYYVDSVKG | RFTISRDNAKKSLFLQMNSLRAEDTAVYYCAK | GEILPLYFDY | WGQGTLVTVSS |
| 14 | EVQLVESGGGLVQPGGSLRLSCAASGFTFS | SYQMY | WVRQAPGKGLEWVA | SIKQDGSEEYYVDSVKG | RFTISRDNAKNSLFLQMNSLRAEDTAVYYCAK | GEILPLYFDY | WGQGTLVTVSS |
| 15 | QVQLVESGGGLVQPGGSLRLSCAASGFTFS | SYGMY | WVRQAPGKGLEWVA | KIEQDGSEEYYVDSVKG | RFTISRDNAKNSLYLQMNSLRAEDTAVYYCAK | GEILPLYFDY | WGQGTLVTVSS |
| 16 | EVQLVESGGGLVQPGGSLRLSCAASGFTFS | SYGMY | WVRQAPGKGLEWVA | SIEQDGSEKYYVDSVKG | RFTISRDNAKNSLYLQMNSLRAEDTAVYYCAK | GEILPLYFDY | WGQGTLVTVSS |
| 17 | EVQLVESGGGLVQRGGSLRLSCAASGFTFS | SYRMY | WVRQAPGKGLEWVA | SIEQDGSEEYYVDSVKG | RFTISRDNAKKSLFLQMNSLRAEDTAVYYCAK | GEILPLYFDY | WGQGTLVTVSS |
| 18 | EVQLVESGGGLVQPGGSLRLSCAASGFTFS | SYSMY | WVRQAPGKGLEWVA | EIRQDGSEQYYVDSVKG | RFTISRDNAKNSLYLQMNSLRAEDTAVYYCAK | GEILPLYFDY | WGQGTLVTVSS |
| 19 | EVQLVESGGGLVQPGGSLRLSCAASGFTFS | SYSMY | WVRQAPGKGLEWVA | EIKQDGSEQYYVDSVKG | RFTISRDNAKNSLYLQMNGLRAEDTAVYYCAK | GEILPLYFDY | WGQGTLVTVSS |

TABLE 1-continued

| SEQ ID NO of full length VH | FR1 | CDR1 | FR2 | CDR2 | FR3 | CDR3 | FR4 |
|---|---|---|---|---|---|---|---|
| 20 | EVQLVESGG GLVQPGGSL RLSCAASGF TFS | SYSMY | WVRQAPGK GLEWVA | EIKPTGSVQ YYVSDVKG | RFTISRDNAK NSLYLQMNS LRAEDTAVY YCAK | GEILPLYFDY | WGQGTLVT VSS |
| 21 | EVQLVESGG GLVQPGGSL RLSCAASGF TFS | SYSMY | WVRQAPGK GLEWVA | EIKQDGSVQR YYVGGVKG | FTISRDNAK NSLYLQMNS LRAEDTAVY YCAK | GEILPLYFDY | WGQGTLVT VSS |
| 22 | EVQLVESGG GLVQPGGSL RLSCATSGFT FS | SYGMY | WVRQAPGK GLEWVA | EIKQDGSEK YYVDSVKG | RFTISRDNAK NSLYLQMNS LRAEDTAVY YCAK | GEILPLYFDY | WGQGTLVT VSS |
| 23 | EVQLVESGG GLVQPGGSL RLSCAASGF TFS | SYGMY | WVRQAPGK GLEWVA | KIEQDGSEE YYADSVKG | RFTISRDNAK KSLYLQMNS LRAEDTAVY YCAK | GEILPLYFDY | WGQGTLVT VSS |
| 24 | EVQLVESGG GLVLPGGSL RLSCAASGF TFS | SYSMY | WVRQAPGK GLEWVA | EIKQDGSEQ YYVDSVKG | RFTISRDNAK NSLYLQMNS LRAEDTAVY YCAK | GEILPLYFDY | WGQGTLVT VSS |
| 25 | EVQLVESGG GLVRPGGSL RLSCAASGF TFS | SYGMY | WVRQAPGK GLEWVA | KIEQDGSEE YYVDSVKG | RFTISRDNAK KSLYLQMNS LRAEDTAVY YCAK | GEILPLYFDY | WGQGTLVT VSS |
| 26 | QVQLVESGG GLVQPGGSL RLSCAASGF TFS | SYGMY | WVRQAPGK GLEWVA | EIKQDGSEK YYVDSVKG | RFTISRDNAK NSLFLQMNS LRAEDTAVY YCAK | GEILPLYFDY | WGQGTLVT VSS |
| 27 | QVQLVESGG GLVQPGGSL RLSCAASGF TFS | SYGMY | WVRQAPGK GLEWVA | EIKQDGSEQ YYVDSVKG | RFTISRDNAK NSLFLQMNS LRAEDTAVY YCAK | GEILPLYFDY | WGQGTLVT VSS |
| 28 | EVQLVESGG GLVQPGGSL RLSCAASGF TFS | SYEMY | WVRQAPGK GLEWVA | SIKQDGSEQ YYVDSVKG | RFTISRDNAK NSLYLQMNS LRAEDTAVY YCAK | GEILPLYFDY | WGQGTLVT VSS |
| 29 | QVQLVESGG GLVQPGGSL RLSCAASGF TFS | SYGMY | WVRQAPGK GLEWVA | RIGQDGSEE YYVDSVKG | RFTISRDNAK NSLYLQMNS LRAEDTAVY YCAK | GEILPLYFDY | WGQGTLVT VSS |
| 30 | EVQLVESGG GLVQPGGSL RLSCAASGF TFS | SYRMY | WVRQAPGK GLEWVA | SIEQDGSEE YYVDSVKG | RFTISRDNAK KSLFLQMNS LRAGDTAVY YCAK | GEILPLYFDY | WGQGTLVT VSS |
| 31 | EVQLVESGG GLVQPGGSL RLSCAASGF TFS | SYRMY | WVRQAPGK GLEWVA | SIEQDGSEE YYVDSVKG | RFTISRDNAK KSLFLQMNS LRAEDTAVY YCAK | GEILPLYFDY | WGQGTLVA VSS |
| 32 | EVQLVESGG GLVQPGGSL RLSCAASGF TFS | SYSMY | WVRQAPGK GLEWVA | SIDQDGSEE YYVDSVKG | RFTISRDNAK KSLYLQMNS LRAEDTAVY YCAK | GEILPLYFDY | WGQGTLVT VSS |
| 33 | EVQLVESGG GLVQPGGSL RLSCAASGF TFS | SYRMY | WVRQAPGK GLEWVA | SIDQDGSEE YYVDSVKG | RFTISRDNAK NSLYLQMNS LRAEDTAVY YCAK | GEILPLYFDY | WGQGTLVT VSS |
| 34 | QVQLVESGG GLVQPGGSL RLSCAASGF TFS | SYNMY | WVRQAPGK GLEWVA | NIEQDGSEE YYVDSVKG | RFTISRDNAK NSLYLQMNS LRAEDTAVY YCAK | GEILPLYFDY | WGQGTLVT VSS |

TABLE 1-continued

| SEQ ID NO of full length VH | FR1 | CDR1 | FR2 | CDR2 | FR3 | CDR3 | FR4 |
|---|---|---|---|---|---|---|---|
| 35 | QVQLVESGG GLVQPGGSL RLSCAASGF TFS | SYRMY | WVRQAPGK GLEWVA | GIEQDGSEE YYVDSVKG | RFTISRDNAK NSLYLQMNS LRAEDTAVY YCAK | GEILPLYFDY | WGQGTLVT VSS |
| 36 | EVQLVESGG GLVQPGGSL RLSCAASGF TFS | SYGMY | WVRQAPGK GLEWVA | GIEQDGSEK YYVDSVKG | RFTISRDNAK NSLYLQMNS LRAEDTAVY YCAK | GEILPLYFDY | WGQGTLVT VSS |
| 37 | EVQLVESGG GLVQPGGSL RLSCAASGF TFS | SYGMY | WVRQAPGK GLEWVA | GIEQDGSEK YYVDSVKG | RFTISRDNAK NSLYLQMNS LRAEDTAVY YCAK | GEILPLYFDY | WGQGTLVT VSS |
| 38 | EVQLVESGG GLVQPGGSL RLSCAASGF TFS | SYGMY | WVRQAPGK GLEWVA | GIEQDGSEK YYVDSVKG | RFTISRDNAK KSLYLQMNS LRAEDTAVY YCAK | GEILPLYFDY | WGQGTLVT VSS |
| 39 | EVQLVESGG GLVQPGGSL RLSCAASGF TFS | SYGMY | WVRQAPGK GLEWVA | GIEQDGSEE YYVDSVKG | RFTISRDNAK NSLFLQMNS LRAEDTAVY YCAK | GEILPLYFDY | WGQGTLVT VSS |
| 40 | EVQLVESGG GLVQPGGSL RLSCAASGF TFS | SYGMY | WVRQAPGK GLEWVA | RIEQDGSEQ YYVDSVKG | RFTISRDNAK NSLYLQMNS LRAEDTAVY YCAK | GEILPLYFDY | WGQGTLVT VSS |
| 41 | EVQLVESGG GLVQPGGSL RLSCAASGF TFS | SYGMY | WVRQAPGK GLEWVA | NIKQDGSEE YYVDSVKG | RFTISRDNAK NSLYLQMNS LRAEDTAVY YCAK | GEILPLYFDY | WGQGTLVT VSS |
| 42 | EVQLVESGG GLVQPGGSL RLSCAASGF TFS | SYGMY | WVRQAPGK GLEWVA | NIKQDGSEE YYVDSVKG | RFTISRDNAK NSLYLQMNS LRAEDTAVY YCAK | GEILPLYFDY | WGQGTLVT VSS |
| 43 | EVQLVESGG GLVQPGGSL RLSCAASGF MFS | SYGMY | WVRQAPGK GLEWVA | NIEQDGSEK YYVDSVKG | RFTISRDNAK KSLYLQMNS LRAEDTAVY YCAK | GEILPLHFDY | WGQGTLVT VSS |
| 44 | EVQLVESGG GLVKPGGSL RLSCAASGF MFS | SYGMY | WVRQAPGK GLEWVA | NIEQDGSEK YYVDSVKG | RFTISRDNAK KSLYLQMNS LRAEDTAVY YCAK | GEILPLHFDY | WGQGTLVT VSS |
| 45 | EVQLVESGG GLVQPGGSL RLSCAASGF TFS | SYGMY | WVRQAPGK GLEWVA | NIKQDGSEQ YYVDSVKG | RFTISRDNAK KSLYLQMNS LRAEDTAVY YCAK | GEILPLHFDY | WGQGTLVT VSS |
| 46 | EVQLVESGG GLVQPGGSL RLSCAVSGF TFS | SYSMY | WVRQAPGK GLEWVA | NIKQDGSEK YYVDSVKG | RFTISRDNAK NSLYLQMNS LRAEDTAVY YCAK | GEILPLHFDY | WGQGTLVT VSS |
| 47 | EVQLVESGG GLVQPGGSL RLSCAASGF TFS | SYSMY | WVRQAPGK GLEWVA | NIKQDGSEK YYVDSVKG | RFTISRDNAK NSLYLQMNS LRAEDTAVY YCAK | GEILPLYFDH | WGQGTLVT VSS |
| 48 | EVQLVESGG GLVQRGGSL RLSCAASGF TFS | SYWMY | WVRQAPGK GLEWVA | KIKQDGSEK YYVDSVKG | RFTISRDNAK NSLFLQMNS LRAEDTAVY YCAK | GEILPLQFDY | WGQGTLVT VSS |
| 49 | EVQLVESGG GLVQRGGSL RLSCAASGF TFS | SYWMY | WVRQAPGK GLEWVA | KINQDGSEK YYVDSVKG | RFTISRDNAK NSLYLQMNS LRAEDTAVY YCAK | GEILPLQFDY | WGQGTLVT VSS |

TABLE 1-continued

| SEQ ID NO of full length VH | FR1 | CDR1 | FR2 | CDR2 | FR3 | CDR3 | FR4 |
|---|---|---|---|---|---|---|---|
| 50 | QVQLVESGGGLVQRGGSLRLSCAASGFTFS | SYWMY | WVRQAPGKGLEWVA | KINQDGSEKYYVDSVKG | RFTISRDNAKNSLYLQMNSLRAEDTAVYYCAK | GEILPLQFDY | WGQGTLVTVSS |
| 51 | QVQLVESGGGLVQPGGSLRLSCAASGFTFS | SYWMY | WVRQAPGKGLEWVA | KINQDGSEKYYVDSVKG | RFTISRDNAKNSLYLQMNSLRAEDTAVYYCAK | GEILPLQFDY | WGQGTLVTVSP |
| 52 | EVQLVESGGGLVQPGGSLRLSCAASGFTFS | SYQMY | WVRQAPGKGLEWVA | EIKQDGSEQYYVDSVKG | RFTISRDNAKNSLFLQMNSLRAEDTAVYYCAK | GEILPLYFDH | WGQGTLVTVSS |
| 53 | EVQLVESGGGLVQPGGSLRLSCAASGFTFS | SYSMI | WVRQAPGKGLEWVA | DIKQDGSEKYYVDSVKG | RFTISRDNAKNSLYLQMNSYLRAEDTAVYYCAK | GEVLPLYFD | WGQGTLVTVSS |
| 54 | EVQLVESGGGLVQPGGSLRLSCAASGFTFS | SYSMI | WVRQAPGKGLEWVA | DIKQDGSEKYYVDSVKG | RFTISRDNAKNSLYLQMNSYLRAEDTAVYYCAK | GEVLPLYFD | WGQGTLVTVSS |
| 56 | EVQLVESGGGLVQPGGSLRLSCAASGFTFS | SYNMY | WVRQAPGKGLEWVA | EIDQDGSEKYYVDSVKG | RFTISRDNAKNSLFLQMNSLRAEDTAVYYCAK | GEILPLYFDH | WGQGTLVTVSS |
| 57 | QVQLVESGGGLVQPGGSLRLSCAASGFTFS | SYRMY | WVRQAPGKGLEWVA | SIEQDGSEEYYVDSVKG | RFTISRDNAKRSLFLQMSSLRAEDSAVYYCAK | GEILPLYFDY | WGQGTLVTVSS |
| 58 | QVQLVESGGGLVQPGGSLRLSCAASGFTFS | SYQMY | WVRQAPGKGLEWVA | GIEQDGSEEYYVDSVKG | RFTISRDNAKNSLYLQM NSLRAEDTAVYYCAK | GEILPLYFDH | WGQGTLVTVSS |
| 59 | QVQLVESGGGLVQPGGSLRLSCAVSGFTFS | SYEMY | WVRQAPGKGLEWVA | NIKQDGSEKYYVDSVKG | RFTISRDNAKNSLYLQM NSLRAEDTAMYYCAK | GEILPLHFDY | RGQGTLVTVSS |
| 60 | EVQLVESGGGLVQPGGSLRLSCAVSGFTFS | SYSMY | WVRQAPGKGLEWVA | NIKQDGSEKYYVDSVKG | RFTISRDNAKNLLYLQMNSLRVEDTAVYYCAK | GEILPLYFDY | RGQGTLVTVSS |
| 61 | QVQLVESGGGLVQPGGSLRLSCAVSGFTFS | SYRMY | WVRQAPGKGLEWVA | SINQDGSEKYYVDSVKG | RFTISRDNAKNSLYLQMNSLRAEDTAMYYCAK | GEILPLHFDY | RGQGTLVTVSS |
| 62 | QVQLVESGGGMVQPGGSLRLSCAVSGFTFS | SYRMY | WVRQAPGKGLEWVA | SINQDGSEKYYVDSVKG | RFTISRDNAKNSLYLQMNSLRAEDTAMYYCAK | GEILPLHFDY | RGQGTLVTVSS |
| 63 | QVQLQESGGDWVQPGGSLRLSCGASGFTFS | SYWMY | WVRQAPGKGLEWVA | KIKQDGTEKYYVDSVKG | RFTISRDNAKNSLYLQMNSLRAEDTAVYYCAK | GEILPHYFDY | WGQGTLVTVSS |
| 64 | EVQLVESGGGLVQPGGSLRLSCTASGFTFS | NYSMY | WVRQAPGKGLEWVA | NIKQDGSEEYYVDSVKG | RFTISRDNARNSLYLQMISLRAEDTAVYYCAK | GEILPLYFDH | WGQGTLVTVSS |
| 65 | EVQLVESGGGLVQPGGSLRLSCTASGFTFS | NYSMY | WVRQAPGKGLEWVA | NIKQDGSEEYYVDSVKG | RFTISRDNARNSLYLQMISLRAEDTAVYYCAK | GEILPLYFDH | WGQGTLVTVSS |

TABLE 1-continued

| SEQ ID NO of full length VH | FR1 | CDR1 | FR2 | CDR2 | FR3 | CDR3 | FR4 |
|---|---|---|---|---|---|---|---|
| 66 | QVQLVESGG GLVQPGGSL RLSCTASGFT FS | NYSMY | WVRQAPGK GLEWVA | NIKQDGSEE YYVDSVKG | RFTISRDNAR NSLYLQMISL RAEDTAVYY CAK | GEILPLYFDH | WGQGTLVT VSS |
| 67 | EVQLVESGG GLVQPGGSL RLSCAASGF TFS | SYGMY | WVRQAPGK GLEWVA | KIEQDGSEE YYVDSVKG | RFTISRDNAK NSLYLQMNS LRAEDTAVY YCAK | GEILPLYFDY | WGQGTLVT VSS |
| 68 | EVQLVESGG GLVQPGGSL RLSCAASGF TFS | SYGMY | WVRQAPGK GLEWVA | KIEQDGSVE YYVDSVKG | RFTISRDNAK NSLYLQMNS LRAEDTAVY YCAK | GEILPLYFDY | WGQGTLVT VSS |
| 69 | EVQLVESGG GLVQPGGSL RLSCAASGF TFS | SYQMY | WVRQAPGK GLEWVA | GIKQDGSEQ YYVDSVKG | RFTISRDNAK KSLYLQMNS LRAEDTAVY YCAK | GEILPLYFDH | WGQGTLVT VSS |
| 70 | EVQLVESGG GLVQPGGSL RLSCAASGF TFS | SYGMY | WVRQAPGK GLEWVA | EIKQDGSEE YYVDSVKG | RFTISRDNAK NSLFLQMNS LRAEDTAVY YCAK | GEILPLYFDY | WGQGTLVT VSS |
| 71 | EVQLVESGG GLVQPGGSL RLSCAASGF TFS | SYSMY | WVRQAPGK GLEWVA | GIEQDGSEE YYVDSVKG | RFTISRDNAK NSLFLQMNS LRAEDTAVY YCAK | GEILPLYFDY | WGQGTLVT VSS |
| 72 | EVQLVESGG GMVQPGGS LRLSCAASGF TFS | SYRMY | WVRQAPGK GLEWVA | EIEQDGSEQ YYVDSVKG | RFTISRDNAK NSLFLQMNS LRAEDTAVY YCAK | GEILPLYFDY | WGQGTLVT VSS |
| 73 | EVQLVESGG GLVQPGGSL RLSCAASGF TFS | SYGMY | WVRQAPGK GLEWVA | EINQDGSEQ YYVDSVKG | RFTISRDNAK NSLYLQMNS LRAEDTAVY YCAK | GEILPLYFDY | WGQGTLVT VSS |

The C terminus of a $V_H$ domain ends in VTVSS (SEQ ID NO:77). In one embodiment of the binding molecules described herein, the $V_H$ domain comprises additional C terminal residues, for example 1 to 15 additional C terminal residues, for example 1, 2, 3, 4, 5, 6, 7, 8, 9 or 10 additional amino acids. In one embodiment, the $V_H$ domain comprises additional C terminal residues of from 1 to 15 amino acid residues, for example 1, 2, 3, 4, 5, 6, 7, 8, 9 or 10 wherein said residues are residues of the $C_H1$ domain. In other words, the $V_H$ domain is extended into the $C_H1$ domain. In one embodiment, said extension comprises at least one alanine residue, for example a single alanine residue, a pair of alanine residues or a triplet of alanine residues. Such extended $V_H$ domains are within the scope of the invention. In one embodiment, the C terminus of a $V_H$ domain is truncated and one or more of VTVSS (SEQ ID NO:77) may be deleted. In one embodiment, one or more of VTVSS (SEQ ID NO:77) may be substituted for another residue.

Also within the scope of the invention are $V_H$ domains that comprise additional C or N terminal residues, for example linker residues and/or labels of tags, such as His tags, e.g., hexa-His. In one embodiment, the $V_H$ domain comprises or consists of a variant of SEQ ID NO. 1 and is designated $V_H$ 1.1 (SEQ ID NO:74) having the following amino acid sequence as shown in the examples.

SEQ ID NO: 74
EVQLVESGGGLVQPGGSLRLSCAASGFTFSSYSMYWVRQAPGKGLEWVAE
IKQDGSVQYYVSDVKGRFTISRDNAKNSLYLQMNSLRAEDTAVYYCAKGE
ILPLYFDYWGQGTLVTVSSA

Thus, in one aspect, the invention relates to a composition for topical delivery comprising
a) an effective amount of at least one single domain antibody capable of binding human IL-17A wherein said single domain antibody comprises SEQ ID NO:1 or a sequence having at least 75% homology thereto and
b) 10-150 mM Tris/glycine, wherein the pH of said composition is about 5 to about 9.

In one embodiment, the $V_H$ domain comprises or consists of SEQ ID NO:1 or 74.

In one embodiment, the composition comprises Tris/glycine at a concentration of about 10 to about 150 mM, for example 10, 20, 30, 40, 50, 60, 70, 80, 90, 100, 110, 120, 130, 140 or 150 mM. In one embodiment of the compositions of the invention, the concentration of Tris/glycine is about 50 to about 150 mM, for example 50, 60, 70, 80, 90, 100, 110, 120, 130, 140 or 150 mM. In one embodiment, the concentration is about 90 to about 110 mM. In one embodiment, the concentration is about 100 mM.

In one embodiment, the composition further comprises one or more of the following excipients: about 0.1 to about 150 mM L-arginine/glutamic acid, about 0.1 to about 15% sorbitol and/or about 0.1to about 30% propylene glycol. In one embodiment, the composition further comprises 0.1-150 mM L-arginine/glutamic acid. In one embodiment, the composition further comprises 0.1-15% sorbitol. In one embodiment, the composition further comprises 0.1-30% propylene glycol. In one embodiment, the composition further comprises 0.1-150 mM L-arginine/glutamic acid and 0.1-15% sorbitol. In one embodiment, the composition further comprises 0.1-15% sorbitol and 0.1-30% propylene glycol. In one embodiment, the composition further comprises 0.1-150 mM L-arginine/glutamic acid and 0.1-30% propylene glycol. In one embodiment, the composition further comprises 0.1-150 mM L-arginine/glutamic acid, 0.1-15% sorbitol and 0.1-30% propylene glycol.

In one embodiment of the compositions of the invention, the concentration of L-arginine/glutamic acid is about 50 to about 150 mM, for example about 50, 60, 70, 80, 90, 100, 110, 120, 130, 140 or 150 mM. In one embodiment, the concentration is about 90 to 110 mM. In one embodiment, the concentration is about 125 mM.

In one embodiment of the compositions of the invention, the concentration of sorbitol is 5-15%, for example 5%, 6%, 7%, 8%, 9%, 10%, 11%, 12%, 13%, 14% or 15%. In one embodiment, the concentration is about 10%.

In one embodiment of the compositions of the invention, the concentration of propylene glycol about 4 about 30%, for example 4%, 5%, 6%, 7%, 8%, 9%, 10%, 11%, 12%, 13%, 14% or 15%, 16%, 17%, 18%, 19%, 20%, 21%, 22%, 23%, 24%, 25%, 26%, 27%, 28%, 29% or 30%. In one embodiment, the concentration is about 5 to 15%, 10% to 15%, 15% to 20% or 20% to 25%. In one embodiment, the concentration is about 6%. In one embodiment, the concentration is about 14%.

According to some embodiments of the composition of the invention, the pH is in the range of between about 7 and about 8.5, preferably between 7.5 and 8.5. In some embodiments the pH can be selected from about pH 7.0, 7.1, 7.2, 7.3, 7.4, 7.5, 7.6, 7.7, 7.8, 7.9, 8.0, 8.1, 8.2, 8.3, 8.4 or 8.5. In one embodiment, the pH is about 8.0.

A skilled person will understand that various concentration of the components of the composition as set out above can be combined.

In one embodiment, the composition comprises 50 to 150 mM Tris/glycine, 50 to 150 mM L-arginine/glutamic acid, 5 to 15% sorbitol and 4 to 30% propylene glycol wherein the pH of said composition is about 5 to about 9, for example between 7.5 and 8.5.

In one embodiment, the composition comprises about 100 mM Tris/glycine, about 125 mM L-arginine/glutamic acid, about 10% sorbitol and about 6% propylene glycol wherein the pH of said composition is between 7.5 and 8.5, for example about 8.

In some embodiments, the composition comprises at least one anti-IL-17A binding molecule, for example a $V_H$ single domain antibody as described herein. In some embodiments, more than one anti-IL-17A $V_H$ single domain antibody may be present. In one embodiment, the composition comprises a biparatopic or bivalent anti-IL-17A $V_H$ single domain antibody. In another embodiment, the composition further comprises a second antibody or antibody fragment which is not a $V_H$ single domain antibody. The anti-IL-17A $V_H$ single domain antibody can also be used and administered in conjunction with other agents that serve to enhance and/or complement the effectiveness of the antibodies.

Multispecific binding molecules for use in the formulation of the present invention can be constructed using methods known art.

In biparatopic or multispecific binding molecules, the moieties are generally joined by a linker, for example a polypeptide linker. Suitable linkers, for example comprising linker including GS residues such as (Gly4Ser)n, where n=from 1 to 10, e.g., 2, 3, 4, 5, 6, 7, 8, 9 or 10, are known in the art.

If desired, bispecific or multispecific binding molecules can be linked to an antibody Fc region or a fragment thereof, comprising one or both of $C_H2$ and $C_H3$ domains, and optionally a hinge region. For example, vectors encoding bispecific or multispecific binding molecules linked as a single nucleotide sequence to an Fc region or a fragment thereof can be used to prepare such polypeptides.

Exemplary second antigen targets include leukocyte receptors, e.g., MHC, CD2, CD3, CD4, CD7, CD8, CD25, CD28, CD4, CD45, CD58, CD80, CD86 or their ligands; TNF, IL-1 IL-15, IL-23, IL-6 or CD20. This list is not limited to the agents mentioned.

In one embodiment, a second (or third, fourth, fifth etc) moiety can be linked to the $V_H$ domain that binds IL-17A, for example to prolong the half-life of the binding molecule. This moiety may comprise a protein, for example an antibody, or part thereof that binds a serum albumin, e.g., human serum albumin (HSA). In one embodiment, the second moiety may comprise a $V_H$ domain that binds serum albumin, e.g. human serum albumin (HSA).

The second moiety may comprise a serum albumin, e.g. a human serum albumin (HSA) or a variant thereof such as C34S. Further provided is a binding molecule as described herein comprising a $V_H$ domain and an Fc domain or a fragment thereof, e.g., wherein the $V_H$ domain is connected to an Fc domain or a fragment thereof. Further provided is a binding molecule that comprises a second variable domain that specifically binds a second antigen, where the second antigen is an antigen other than human IL-17A. The second antigen may be a cluster of differentiation (CD) molecule or a Major Histocompatibility Complex (MHC) Class II molecule.

Binding molecules described herein can be obtained by using transgenic knock out (KO) rodents, for example mice, that lack endogenous immunoglobulins. Preferably, the mouse does not comprise a functional heavy chain, lambda light chain and kappa light chain locus. The loci may be rendered non-functional through deletion, insertion, gene editing or other techniques known in the art. A mouse having a non-functional endogenous lambda and kappa L-chain loci may, for example, be made as disclosed in WO 2003/000737, which is hereby incorporated by reference in its entirety. A mouse having a non-functional heavy chain locus may, for example, be made as disclosed in WO 2004/076618, which is hereby incorporated by reference in its entirety.

For example, the transgenic mouse comprises a vector, for example a Yeast Artificial Chromosome (YAC) for expressing a heterologous heavy chain locus. YACs are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopaedia of Life Sciences 2002 Macmillan Publishers Ltd, Nature Publishing Group/www.els.net).

For example, the YAC may comprise a plethora of human $V_H$, D and J genes in combination with mouse immunoglobulin constant region genes lacking $C_H1$ domains, mouse enhancer and regulatory regions, as disclosed in WO2016/062990, which is hereby incorporated by reference in its entirety.

Transgenic mice can be created according to standard techniques. The transgenic mouse may be immunized with an IL-17A antigen and a library of sequences comprising $V_H$ domain sequences from said mouse is then generated. Sequences comprising $V_H$ domain sequences from said libraries are isolated using standard techniques.

The active molecule present in the composition, e.g. the antibody, antibody fragment, single domain antibody or $V_H$ single domain antibody binding to human IL-17A, may be present in the composition at a concentration ranging from about 0.5 mg/ml to about 300 mg/ml. In some embodiments the concentration of the active molecule is about 10 mg/ml to 200 mg/ml or about 10 mg/ml to 100 mg/ml. In some embodiment, the concentration is about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, about 30 mg/ml, about 31 mg/ml, about 32 mg/ml, about 33 mg/ml, about 34 mg/ml, about 35 mg/ml, about 36 mg/ml, about 37 mg/ml, about 38 mg/ml, about 39 mg/ml, about 40 mg/ml, about 41 mg/ml, about 42 mg/ml, about 43 mg/ml, about 44 mg/ml, about 45 mg/ml, about 46 mg/ml, about 47 mg/ml, about 48 mg/ml, about 49 mg/ml, about 50 mg/ml, about 51 mg/ml, about 52 mg/ml, about 53 mg/ml, about 54 mg/ml, about 55 mg/ml, about 56 mg/ml, about 57 mg/ml, about 58 mg/ml, about 59 mg/ml, about 61 mg/ml, about 62 mg/ml about 63 mg/ml about 64 mg/ml about 65 mg/ml, about 66 mg/ml, about 67 mg/ml, about 68 mg/ml, about 69 mg/ml, about 70 mg/ml, about 70 mg/ml, about 71 mg/ml, about 72 mg/ml, about 73 mg/ml, about 74 mg/ml, about 75 mg/ml, about 76 mg/ml, about 77 mg/ml, about 78 mg/ml, about 79 mg/ml, about 80 mg/ml, about 80 mg/ml, about 81 mg/ml, about 82 mg/ml, about 83 mg/ml, about 84 mg/ml, about 85 mg/m, about 86 mg/m, about 87 mg/m, about 88 mg/m, about 89 mg/ml, about 90 mg/ml, about 91 mg/ml, about 92 mg/ml, about 93 mg/ml, about 94 mg/ml, about 95 mg/ml, about 96 mg/ml, about 97 mg/ml, about 98 mg/ml, about 99 mg/ml, about 100 mg/ml. In one embodiment, the concentration is about 20 mg/ml to 40 mg/mi. In one embodiment, the concentration is about 20 mg/mi. In one embodiment, the concentration is about 40 mg/mi.

In one embodiment, the concentration of the $V_H$ domain is about 20 mg/ml to about 50 mg/ml, for example about 20 mg/ml or about 40 mg/ml.

Osmolality of a formulation for therapeutic application is important. Normal osmolality of blood/serum is about 300-310 mOsm/L. As shown in the examples, the binding molecule in formulation showed osmolality that was greater than physiological levels. Thus, in one embodiment, osmolality of the formulation is at physiological level or higher. For example, osmolality is about 2 mOsm/kg or higher. In one embodiment, osmolality is about 2,386 mOsm/kg.

As shown in the examples, compositions according to the invention are stable under various conditions. As used herein, the term "stability" generally relates to maintaining the integrity or to minimizing the degradation, denaturation, aggregation or unfolding of a biologically active agent, i.e. the IL-17 binding molecule described herein. Stability of the active molecule in the composition can be determined by various means known to the skilled person.

In some embodiments, the antibody stability or aggregation is determined by size exclusion chromatography (SEC), a separation technique based on the molecular size of the components, for example antibodies or fragments thereof, their diffusion coefficient, and surface properties. Thus, for example, SEC can separate antibodies or antibody fragments in their natural three-dimensional conformation from antibodies in various states of denaturation, and/or antibodies that have been degraded. In SEC, the stationary phase is generally composed of inert particles packed into a dense three-dimensional matrix within a glass or steel column. The mobile phase can be pure water, an aqueous buffer, an organic solvent, mixtures of these, or other solvents. The stationary-phase particles have small pores and/or channels which will only allow species below a certain size to enter. Large particles are therefore excluded from these pores and channels, but the smaller particles are removed from the flowing mobile phase. The time particles spend immobilized in the stationary-phase pores depends, in part, on how far into the pores they can penetrate. Their removal from the mobile phase flow causes them to take longer to elute from the column and results in a separation between the particles based on differences in their size.

For the separation of biomolecules in aqueous or aqueous/organic mobile phases, SEC is referred to as gel filtration chromatography (GFC), while the separation of organic polymers in non-aqueous mobile phases is called gel permeation chromatography (GPC).

SEC can be combined with an identification technique to identify or characterize proteins, or fragments thereof known to the skilled person. Protein identification and characterization can be accomplished by various techniques, including but not limited chromatographic techniques, e.g., high-performance liquid chromatography (HPLC), immunoassays, electrophoresis, ultraviolet/visible/infrared spectroscopy, Raman spectroscopy, surface enhanced Raman spectroscopy, mass spectroscopy, gas chromatography, static light scattering (SLS), Fourier Transform Infrared Spectroscopy (FTIR), circular dichroism (CD), urea-induced protein unfolding techniques, intrinsic tryptophan fluorescence, differential scanning calorimetry, and/or ANS protein binding.

Proteins can be identified by high-pressure liquid chromatography. A well-known technique is HPLC, for example reverse phase HPLC (RP-HPLC) or Anion exchange high performance liquid chromatography (AIEX-HPLC). A liquid solvent containing the protein of interest is loaded onto a separation column, in which the separation occurs. The HPLC separation column is filled with solid particles (e.g. silica, polymers, or sorbents), and the sample mixture is separated into compounds as it interacts with the column particles. SEC and HPLC can be combined, often referred to as SE-HPLC.

In some embodiments, stability refers to a formulation having low to undetectable levels of aggregation, containing no more than 5%, no more than 4%, no more than 3%, no more than 2%, no more than 1% and no more than 0.5% aggregation by weight of protein as measured by high performance size exclusion chromatography (HPSEC), static light scattering (SLS), Fourier Transform Infrared Spectroscopy (FTIR), circular dichroism (CD), urea-induced protein unfolding techniques, intrinsic tryptophan fluorescence, differential scanning calorimetry, and I-anilino-8-naphthalenesulfonic acid (ANS) protein binding techniques or other techniques known in the art.

Stability of the liquid compositions can also be determined by examining biological activities of the antibody (including fragments/parts thereof) during the prolonged storage under the conditions described above, as assessed by various immunological assays including, for example, enzyme-linked immunosorbent assay (ELISA) and radioimmunoassay to measure the ability of the antibody or part thereof (including a $V_H$ domain) to immunospecifically bind to an antigen. In one embodiment, the compositions of the present invention retain, after storage for the above-defined periods, more than 80%, more than 85%, more than 90%, more than 95%, more than 98%, more than 99% or more than 99.5% of the initial biological activities of the formulation prior to the storage, i.e., compared to a reference molecule or formulation representing the IL-17 binding $V_H$ domain prior to storage.

In one embodiment, the compositions of the invention maintain an improved aggregation and stability profile upon storage. In another embodiment, the compositions of the invention have a reduced incidence of insoluble aggregation. In one embodiment, the compositions of the invention maintain an improved stability and/or aggregation profile when stored for extended periods of time at room temperature (between about 20° C. to about 25° C.).

In one embodiment, the compositions of the invention maintain an improved stability and/or aggregation profile when stored for extended periods of time at reduced temperatures (below about 10° C., between about 2° C. to about 8° C., for example, at 5° C.), for up to about 1 week, 2 weeks, 3 weeks, 1 month, 2 months, 3 months, 6 months, 1 year, 2 years, 3 years, 4 years or 5 years.

In another embodiment, the compositions of the invention maintain an improved stability and/or aggregation profile when stored for extended periods at low temperatures, for example 0° C. or below, such from 0° C. to –70° C., such as –1° C., –2° C., –3° C., –4° C., –5° C., –6° C., –7° C., –8° C., –9° C. or –10° C. for up to about 1 week, 2 weeks, 3 weeks, 1 month, 2 months, 3 months, 6 months, 1 year, 2 years, 3 years, 4 years or 5 years.

In one embodiment, a composition of the invention further comprises a penetration enhancer. Numerous chemical penetration enhancers are known in the art and can be used in the composition of the invention. These include, but are not limited to: water, alcohols, preferably alcohols with up to six carbon atoms, for example ethanol, glycols, for example alcohol diethylene glycol (Transcutol®), alkyl-N,N-disubstituted aminoacetates, for example dodecyl-N,N-dimethyl-aminoacetate, esters, for example ethylacetate, Azone® and derivatives, surfactants, for example sodium dodecyl sulphate, terpenes and terpenoids, for example d-Limonene, fatty acids, for example oleic acid, urea and derivatives, for example 1,3-Diphenyl-urea, pyrrolidones, for example N-Methyl-2-pyrrolidone, pyrrolidone carboxylic acid, such as 2-pyrrolidone-5-carboxylic acid, cyclodextrins, for example beta-cyclodextrin, sulphoxides, for example dimethylsulphoxide. Other skin penetration enhancers are known to the skilled person. In one embodiment, the skin penetration enhancers are selected from one or more of Transcutol®, isopropyl myristate or Azone.

Thus, in one embodiment, the invention relates to a composition as described above further comprising Transcutol®. As shown in the examples, it was demonstrated that compositions comprising Transcutol® showed improved penetration and retained good stability. The concentration of Transcutol® can be about 1-60%, for example about 40%.

In one embodiment, the invention relates to a composition as described above having a concentration of propylene glycol of more than 10%, for example 11%, 12%, 13%, 14%, 15% or higher. As shown in the examples, it was demonstrated that compositions comprising a higher concentration of propylene glycol showed improved penetration and retained good stability.

In one embodiment, a composition of the invention comprises a gelling agent to increase viscosity of the composition for topical administration. This can be selected from carbomers, poloxamer or cellulose derivatives, such as methylcellulose, hydroxypropyl cellulose, hydroxypropylmethyl cellulose. Concentration of the gelling agent can be from 0.5% to 20%. In one embodiment, the gelling agent is poloxamer. The concentration of poloxamer is for example selected from 0.5% to 20%, for example 1%, 2%, 3%, 4%, 5%, 6%, 7%, 8%, 9%, 10%, 11%, 12%, 13%, 14%, 15%, 16%, 17%, 18%, 19% or 20%.

In one embodiment, a composition of the invention comprises a penetration enhancer and a gelling agent, for example Transcutol® and poloxamer.

In a further embodiment, the invention relates to
a) an effective amount of a single domain antibody comprising a $V_H$ domain capable of binding human IL-17A wherein said $V_H$ domain comprises SEQ ID NO:1 or a sequence having at least 75% homology thereto,
b) about 100 mM Tris/glycine,
c) about 125 mM L arginine/glutamic acid,
d) about 10% sorbitol and
e) about 14% propylene glycol wherein the pH of said composition is 7.5 to 8.5, for example 8.

In a further embodiment, the invention relates to
a) an effective amount of a single domain antibody comprising a $V_H$ domain capable of binding human IL-17A wherein said $V_H$ domain comprises SEQ ID NO:1 or a sequence having at least 75% homology thereto,
b) about 100 mM Tris/glycine,
c) about 125 mM L arginine/glutamic acid,
d) about 10% sorbitol,
e) about 6% propylene glycol and
f) about 20% Transcutol® wherein the pH of said composition is 7.5 to 8.5 for example 8.

In some embodiments of the invention, the composition can comprise a preservative. The preservative can be selected from Phenol, m-cresol, benzyl alcohol, benzalkonium chloride, benzalthonium chloride, phenoxyethanol and methyl paraben.

In some embodiments, the compositions can comprise an antioxidant agent. In some embodiments, the antioxidant is selected from the group comprising, methionine, sodium thiosulfate, catalase, and platinum.

In one embodiment, the compositions of the invention comprise one or more of the following excipients: Azone, B-cyclodextrin, benzyl alcohol, glyceryl monostearate, PEG 100 Stearate, hexylene glycol, histidine, hydroxypropyl cellulose, isopropyl myristate, liquid parrafin (light mineral oil), medium chain triglycerides (captex 300), methyl salicylate, N-methyl-2-pyrrolidone, octyldodecanol, oleyl alcohol, poloxamer, for example poloxamer-407, polyvinyl alcohol, Potassium Sorbate, proline, propyl gallate, pyrrolidinone carboxylic acid, sorbitan mono oleate (Span 80), sorbitan stearate (Span 60), steareth-20, stearic acid, Tefose 63, Transcutol®, triacetin, steareth-20, steareth-2, dimethyl Sulfoxide, octyldodecanol, Captex 300, polysorbate 80, Span 80, proline, light mineral oil or Arlacel 165.

Other contemplated excipients, which may be utilized in the compositions of the invention include, for example, antimicrobial agents, antioxidants, antistatic agents, lipids such as phospholipids or fatty acids, steroids such as cholesterol, gelatin, casein, salt-forming counterions such sodium and the like. These and additional known pharmaceutical excipients, such as physiologically acceptable carriers and/or additives suitable for use in the formulations of the invention are known in the art, e.g., as listed in "The Handbook of Pharmaceutical Excipients, 4th edition, Rowe et al., Eds., American Pharmaceuticals Association (2003) incorporated herein by reference; and Remington: the Science and Practice of Pharmacy, 21st edition, Gennaro, Ed., Lippincott Williams & Wilkins (2005) incorporated herein by reference. The term "physiologically acceptable carrier" refers to a carrier which does not have a significant detrimental impact on the treated host and which retains the therapeutic properties of the compound with which it is administered.

In some embodiments, the compositions of the invention comprise one or more further excipient as shown in table 3. Thus, the excipient is selected from one or more of Transcutol®, steareth-20, steareth-2, octyldecanol or isopropyl myristate.

In one embodiment, a composition of the invention as described above is formulated for topical administration to the skin, gum or surface of the eye. Thus, the composition is in the form of a liquid, gel, suspension, ointment, cream, lotion or the like.

In another embodiment, a composition of the invention as described above is freeze or spray dried. In one embodiment, the freeze or spray dried composition comprises the components set out above but lacks propylene glycol and/or sorbitol.

As explained above, the invention provides a freeze or spray dried composition comprising an effective amount of at least one single domain antibody capable of binding human IL-17A and 10-150 mM Tris/glycine wherein the pH of said composition is about 5 to about 9. In one embodiment of the compositions of the invention, the concentration of Tris/glycine is 10, 20, 30, 40, 50, 60, 70, 80, 90, 100, 110, 120, 130, 140 or 150 mM. In one embodiment of the compositions of the invention, the concentration of Tris/glycine is about 50 to about 150 mM, for example 50, 60, 70, 80, 90, 100, 110, 120, 130, 140 or 150 mM. In one embodiment, the concentration is about 90 to 110 mM. In one embodiment, the concentration is about 100 mM. In one embodiment, composition further comprises 50-150 mM L-arginine/glutamic acid wherein the pH of said composition is about 5 to about 9. In one embodiment of the compositions of the invention, the concentration of L-arginine/glutamic acid is 10, 20, 30, 40, 50, 60, 70, 80, 90, 100, 110, 120, 130, 140 or 150 mM. In one embodiment of the compositions of the invention, the concentration of L-arginine/glutamic acid is about 50 to about 150 mM, for example about 50, 60, 70, 80, 90, 100, 110, 120, 130, 140 or 150 mM. In one embodiment, the concentration is about 90 to 110 mM. In one embodiment, the concentration is about 125 mM.

In one embodiment of the freeze or spray dried compositions of the invention, the composition comprises
  a) an effective amount of a single domain antibody comprising a $V_H$ domain capable of binding human IL-17A wherein said $V_H$ domain comprises SEQ ID NO:1 or a sequence having at least 75% homology thereto,
  b) about 100 mM Tris/glycine and
  c) about 125 mM L arginine/glutamic acid
  wherein the pH of said composition is 7.5 to 8.5, for example 8.

In the freeze or spray dried composition, the IL-17A binding molecule is as described elsewhere herein. For example, the IL-17A binding molecule comprises at least one single domain antibody comprising a $V_H$ domain capable of binding human IL-17A. In another embodiment, said $V_H$ domain comprises CDR3 of SEQ ID NO:4. In another embodiment, said $V_H$ domain comprises SEQ ID NO:1 or a sequence having at least 50%, 60%, 70% or 75% homology thereto. In another embodiment, said $V_H$ domain comprises a $V_H$ domain selected from Table 1 and defined as in any of SEQ ID NOs: 5 to 73 or SEQ ID NO:74.

The freeze or spray dried compositions of the invention are reconstituted using one or more acceptable excipient/reconstitution agent. For example a penetration enhancer such as propylene glycol may be included.

In another aspect, the invention thus relates to a reconstituted freeze or spray dried composition comprising a composition as described above and further comprising propylene glycol, for example at a concentration of 4-30%, for example 4%, 5%, 6%, 7%, 8%, 9%, 10%, 11%, 12%, 13%, 14% or 15%, 16%, 17%, 18%, 19%, 20%, 21%, 22%, 23%, 24%, 25%, 26%, 27%, 28%, 29% or 30%. In one embodiment, the concentration is about 5-15%, 10%-15%, 15%-20% or 20% to 25%. In one embodiment, the concentration is about 6% or 14%.

In one embodiment, the freeze dried or spray dried composition is reconstituted for topical administration. In one embodiment, the reconstitution excipients are selected from one or more of L-arginine/glutamic acid, sorbitol and/or propylene glycol.

In one embodiment, the reconstitutions excipients comprise 50-150 mM L-arginine/glutamic acid, for example 50, 60, 70, 80, 90, 100, 110, 120, 130, 140 or 150 mM L-arginine/glutamic acid, 5-15% sorbitol, for example 5%, 6%, 7%, 8%, 9%, 10%, 11%, 12%, 13%, 14% or 15% sorbitol and/or 4-30% propylene glycol, for example 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% propylene glycol.

Preferably, the pH of said composition is 5 to 9, for example 7.5 to 8.5, for example 8.

In another aspect, the invention relates to a method for making a reconstituted formulation for topical administration comprising providing a freeze or spray dried composition as described above and adding an acceptable excipient/reconstitution agent, for example a penetration enhancer such as propylene glycol. Propylene glycol may be added at a concentration of 4-30%, for example for example 4%, 5%, 6%, 7%, 8%, 9%, 10%, 11%, 12%, 13%, 14% or 15%, 16%, 17%, 18%, 19%, 20%, 21%, 22%, 23%, 24%, 25%, 26%, 27%, 28%, 29% or 30%. In one embodiment, the concentration is about 5-15%, 10%-15%, 15%-20% or 20% to 25%. In one embodiment, the concentration is about 6% or 14%.

In one embodiment, the freeze or spray dried compositions of the invention maintain an improved stability and aggregation profile when stored for extended periods of time at room temperature (between about 20° C. to about 25° C.) or at reduced temperatures (below about 10° C., between about 2° C. to about 8° C., for example at 5° C.), for up to about 1 week, 2 weeks, 3 weeks, 1 month, 2 months, 3 months, 6 months, 1 year, 2 years, 3 years, 4 years or 5 years.

In another embodiment, the freeze or spray dried compositions of the invention maintain an improved stability and/or aggregation profile when stored for a period of time, such as up to about 1 week, up to about 2 weeks, up to about 3 weeks, up to about 1 month, up to about 2 months, up to about 3 months, or up to about 6 months at a temperature of between about 0° C. to about 8° C., for example at about 5° C.

In another embodiment, the freeze or spray dried compositions of the invention maintain an improved stability and/or aggregation profile when stored for extended periods at reduced temperature, for example 0° C. or below, such from 0° C. to −70° C., such as −1° C., −2° C., −3° C., −4° C., −5° C., −6° C., −7° C., −8° C., −9° C. or −10° C. for up to about 1 week, 2 weeks, 3 weeks, 1 month, 2 months, 3 months, 6 months, 1 year, 2 years, 3 years, 4 years or 5 years.

In a preferred embodiment, the freeze or spray dried compositions of the invention maintain an improved stability and/or aggregation profile when stored for extended period, for example for up to about 1 week, 2 weeks, 3 weeks, 1 month, 2 months, 3 months, 6 months, 1 year, 2 years, 3 years, 4 years or 5 years, at about 20° C. to about 25° C., for example 20° C., 21° C., 22° C., 23° C., 24° C. or 25° C.

The invention further relates to a method for the prevention and/or treatment of a disease comprising administering a composition of the invention to a subject.

The term "subject" for purposes of treatment includes any subject, and preferably is a subject who is in need of the treatment of the targeted pathologic condition for example autoimmune disease. For purposes of prevention, the subject is any subject, and preferably is a subject that is at risk for, or is predisposed to, developing the targeted pathologic condition for example autoimmune disease. The term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

More in particular, the invention relates to a method for the prevention and/or treatment of a disease selected from the non-limiting group consisting of the diseases and disorders listed herein, said method comprising administering, to a subject in need thereof, a pharmaceutically active amount of a binding molecule or a pharmaceutical composition of the invention. Examples of the immune related diseases that can be treated according to the invention will be clear to the skilled person based on the disclosure herein, and for example include autoimmune diseases, inflammatory conditions, allergies and allergic conditions, hypersensitivity reactions, severe infections, and organ or tissue transplant rejection.

The invention also relates to a composition of the invention for use in the treatment of disease. In another aspect, the invention relates to a composition of the invention for use in the treatment of a disease selected from the non-limiting group consisting of the diseases and disorders listed herein.

In another aspect, the invention relates to the use of a composition of the invention in the manufacture of a medicament for the treatment of a disease, selected from the non-limiting group consisting of the diseases and disorders listed herein, for example autoimmune disease, inflammatory conditions, allergies and allergic conditions, hypersensitivity reactions, severe infections, and organ or tissue transplant rejection.

According to the different aspects above, the disease may be selected from the following non-limiting list: psoriasis, systemic lupus erythematosis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain Barre syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease, gluten-sensitive enteropathy, and Whipple's disease, autoimmune or immune-mediated skin diseases including bullous skin diseases, erythema multiforme and contact dermatitis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, autoimmune haematological disorders (including e.g., hemolytic anaemia, aplastic anaemia, pure red cell anaemia and idiopathic thrombocytopenia), autoimmune inflammatory bowel disease (including e.g., ulcerative colitis, Crohn's disease and Irritable Bowel Syndrome), transplantation associated diseases including graft rejection and graft-versus-host-disease.

A composition of the invention is also useful for the treatment, prevention, or amelioration of asthma, bronchitis, pneumoconiosis, pulmonary emphysema, and other obstructive or inflammatory diseases of the airways.

In a preferred embodiment, the disease is a skin disease. In one embodiment, the disease is selected from psoriasis, spondyloarthropathies, uveitis, gingivitis atopic dermatitis and asthma.

A composition of the invention is useful for treating undesirable acute and hyperacute inflammatory reactions which are mediated by IL-17, or involve IL-17 production, or the promotion of TNF release by IL-17, e.g., acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS-related cachexia, e.g., associated with or consequential to HIV infection.

A composition of the invention are particularly useful for treating diseases of bone metabolism including osteoarthritis, osteoporosis and other inflammatory arthritis, and bone loss in general, including age-related bone loss, and in particular periodontal disease.

A composition of the invention may be administered as the sole active ingredient or in combination with one or more other drug, e.g., an immunosuppressive or immunomodulating agent or other anti-inflammatory agent, e.g., for the treatment or prevention of diseases mentioned above. For example, the binding molecule of the invention maybe used in combination with immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g., a recombinant binding molecule having at least a portion of the extracellular domain of CTLA4 or a mutant thereof, e.g., an at least extracellular portion of CTLA4 or a mutant thereof joined to a non-CTLA4 protein sequence, e.g., CTLA4lg (e.g., designated ATCC 68629) or a mutant thereof, e.g., LEA29Y; adhesion molecule inhibitors, e.g., LFA-I antagonists, ICAM-I or -3 antagonists, VCAM-4 antagonists or VLA-4 antagonists; or a chemotherapeutic agent, e.g., paclitaxel, gemcitabine, cisplatinum, doxorubicin or 5-fluorouracil; anti TNF agents, e.g., monoclonal antibodies to TNF, e.g., infliximab, adalimumab, CDP870, or receptor constructs to TNF-RI or TNF-RII, e.g., Etanercept®, PEG-TNF-RI;

blockers of proinflammatory cytokines, IL-I blockers, e.g., Anakinra or IL-I trap, AAL160, ACZ 885, IL-6 blockers; chemokines blockers, e.g., inhibitors or activators of proteases, e.g., metalloproteases, anti-IL-15 antibodies, anti-IL-6 antibodies, anti-CD20 antibodies, NSAIDs, such as aspirin or an anti-infectious agent. This list is not limited to the agents mentioned.

A composition of the invention may be administered at the same time or at a different time as the other drug e.g., simultaneously, separately or sequentially.

The compositions according to the invention are of particular use in topical delivery.

Accordingly, the compositions are preferably in the form of a cream, lotion, spray, powder, vapour, solution, gel, ointment, paste, suspension, emulsion, foam, or the like.

The compositions may also be applied as a plaster, patch, bioadhesive or dressing. Thus, the invention also relates to a plaster, patch, bioadhesive or dressing comprising a formulation of the invention.

In one embodiment, topical delivery is to the lung by way of inhalation. The compositions of the invention are thus administered as a vapour or, in particular in the case of spray or freeze dried compositions directly as a powder.

The compositions can be formulated using any dermatologically acceptable carrier. Exemplary carriers include a solid carrier, such as alumina, clay, microcrystalline cellulose, silica, or talc; and/or a liquid carrier, such as water, an alcohol, a glycol, or a water-alcohol/glycol blend. The therapeutic agents may also be administered in liposomal formulations that allow therapeutic agents to enter the skin.

In specific embodiments, it can be desirable to administer the composition locally to the area in need of treatment.

Thus, in a preferred embodiment of all aspects of the invention, administration of the composition of the invention is by topical administration to healthy or diseased skin. The binding molecule is capable of penetrating at least the outer layer of the skin and can therefore be delivered dermally or transdermally. Accordingly, in one embodiment of the various aspects of the invention, topical delivery of the composition or binding molecule of the invention to the skin is direct delivery into the skin for local non-systemic exposure. In another embodiment, topical delivery of the composition or binding molecule of the invention to the skin is direct delivery to the skin to provide systemic exposure following penetration through all layers of the skin.

The skin that is treated may be diseased or healthy skin. In a preferred embodiment, the skin disease is psoriasis or atopic dermatitis.

Preferably, the surface area to which it is applied is 1%-30% of the body surface area, for example 1%-10% or 1-20%. Administration may thus be to 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 27%, 26%, 28%, 29% or 30% of body surface area. In one embodiment, the disease state is mild. In another embodiment, the disease state is moderate. In another embodiment, the disease state is severe. For the treatment of psoriasis, administration is to areas affected, typically one or more area selected from elbows, knees, palms of hands, scalp, soles of feet, genitals, upper thighs, groin, buttocks, face and torso. For the treatment of atopic dermatitis administration is to areas affected, typically one or more area selected from face, forearms and wrists.

The amount of the binding molecule of the present invention that is effective/active in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions of the invention comprise an effective amount of a binding molecule of the present invention such that a suitable dosage will be obtained. The correct dosage of the compounds will vary according to the particular formulation, the mode of application, and its particular site, host and the disease being treated. Other factors like age, body weight, sex, diet, time of administration, rate of excretion, condition of the host, drug combinations, reaction sensitivities and severity of the disease shall be taken into account.

According to one embodiment, the dose contains an amount of the active molecule that is about 1 μg/kg, about 10 μg/kg, about 20 μg/kg, about 25 μg/kg, about 50 μg/kg, about 100 μg/kg, about 200 μg/kg, about 250 μg/kg, about 500 μg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, or about 11 mg/kg (of mass of the mammal to which the dose it to be administered). In some embodiments, the dose contains about 20 μg/kg, about 25 μg/kg, about 50 μg/kg, about 100 μg/kg, about 200 μg/kg, about 250 μg/kg, 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg of the active molecule.

Dosage regimens may depend on the pattern of pharmacokinetic decay that the practitioner wishes to achieve. For example, in some embodiments, dosing from one-four times a week is contemplated. Even less frequent dosing may be used. In some embodiments, the dose is administered once every 1 week, every 2 weeks, every 3 weeks, every 4 weeks, every 5 weeks, every 6 weeks, every 7 weeks, every 8 weeks, every 9 weeks, every 10 weeks, every 15 weeks, every 20 weeks, every 25 weeks, or longer. In some embodiments, the dose is administered once every 1 month, every 2 months, every 3 months, every 4 months, every 5 months, every 6 months, or longer. The progress of this therapy is easily monitored by conventional techniques and assays. The dosing regimen can vary over time.

The IL17 binding molecule used in the compositions of the invention for medical treatment is as described elsewhere herein. For example, it can be selected from a $V_H$ single domain antibody comprising the CDR1, CDR2 and CDR3 sequences SEQ ID NOs. 2, 3 and 4 as described herein. In one embodiment, the $V_H$ single domain antibody is selected from Table 1. In one embodiment, the $V_H$ single domain antibody comprises SEQ ID NO:1 or a sequence having at least 75% homology thereto, for example SEQ ID NO: 74.

In another aspect, the invention provides a kit or article of manufacture comprising a composition of the invention useful for the treatment of a disease described above. The kit can comprise a container with the composition of interest, for example in the form suitable for topical administration and optionally instructions for use. In one aspect, the invention provides a container, for example a nebulizer or inhaler, comprising a composition of the invention. In one embodiment, the composition is a freeze or spray dried composition of the invention. The IL17 binding molecule used in the composition of the container or kit is a composition of the invention as described elsewhere herein. For example, it can be selected from a $V_H$ single domain antibody comprising the CDR1, CDR2 and CDR3 sequences SEQ ID Nos. 2, 3 and 4 as described herein. In one embodiment, the $V_H$ single domain antibody is selected from Table 1. In one embodiment, the $V_H$ single domain antibody comprises SEQ ID NO:1 or a sequence having at least 75% homology thereto, for example SEQ ID NO: 74.

In another aspect, the invention relates to use of a buffer comprising
a) 50-150 mM Tris/glycine,
b) 50-150 mM L-arginine/glutamic acid
c) 5-15% sorbitol and
d) 4-30% propylene glycol
wherein the pH of said composition is about 5 to 9, e.g. 7.5 to 8.5.

in preparing a formulation comprising an effective amount of a single domain antibody capable of binding human IL-17A, for example a single domain antibody wherein said $V_H$ domain comprises SEQ ID NO:1 or a sequence having at least 75% homology thereto.

In one embodiment, the buffer comprises
a) about 100 mM Tris/glycine,
b) about 125 mM L-arginine/glutamic acid,
c) about 10% sorbitol and
d) about 6% propylene glycol wherein the pH of said composition is 7.5 to 8.5, for example about 8.

The IL17 binding molecule used in the compositions is as described elsewhere herein. For example, it can be selected from a $V_H$ single domain antibody comprising the CDR1, CDR2 and CDR3 sequences SEQ ID Nos. 2, 3 and 4 as described herein. In one embodiment, the $V_H$ single domain antibody is selected from Table 1. In one embodiment, the $V_H$ single domain antibody comprises SEQ ID NO:1 or a sequence having at least 75% homology thereto, for example SEQ ID NO: 74.

In another aspect, the invention relates to a method for preparing a formulation for the treatment of a disorder comprising adding an effective amount of a single domain antibody capable of binding human IL-17A a buffer comprising
a) 50-150 mM Tris/glycine,
b) 50-150 mM L-arginine/glutamic acid,
c) 5-15% sorbitol and
d) 4-30% propylene glycol.

The IL17 binding molecule used in the compositions is as described elsewhere herein. For example, it can be selected from a $V_H$ single domain antibody comprising the CDR1, CDR2 and CDR3 sequences SEQ ID Nos. 2, 3 and 4 as described herein. In one embodiment, the $V_H$ single domain antibody is selected from Table 1. In one embodiment, the $V_H$ single domain antibody comprises SEQ ID NO:1 or a sequence having at least 75% homology thereto, for example SEQ ID NO: 74.

In another aspect, the invention provides a composition as set out in the examples and/or accompanying figures.

Unless otherwise defined herein, scientific and technical terms used in connection with the present disclosure shall have the meanings that are commonly understood by those of ordinary skill in the art. While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety, including references to any gene accession numbers.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein. Unless context dictates otherwise, the descriptions and definitions of the features set out above are not limited to any particular aspect or embodiment of the invention and apply equally to all aspects and embodiments which are described.

The invention is further described in the non-limiting examples.

EXAMPLES

Example 1 Generation of $V_H$ Domain 1.1 Construction of Tg/TKO mice

Mice carrying a heavy-chain antibody transgenic locus in germline configuration within a background that is silenced for endogenous heavy and light chain antibody expression (triple knock-out, or TKO) were created as previously described (VV02004/076618 and WO2003/000737, Ren et al. Genomics, 84, 686, 2004; Zou et al., J. Immunol., 170, 1354, 2003 and WO2016/062990). Briefly, transgenic mice were derived following pronuclear microinjection of freshly fertilised oocytes with a yeast artificial chromosome (YAC) comprising a plethora of human $V_H$, D and J genes in combination with mouse immunoglobulin constant region genes lacking $C_H1$ domains, mouse enhancer and regulatory regions. The transgenic founder mice were back-crossed with animals that lacked endogenous immunoglobulin expression to create the Tg/TKO lines used in the immunisation studies described.

1.2. Antigen for Immunisation

The immunisations used recombinant purified protein. Recombinant human IL-17A was purchased from Peprotech (Peprotech, cat #AF-200-17).

1.3. Immunisation Protocol In the present case, recombinant protein was administered to the Tg/TKO. Briefly, mice aged 8-12 weeks of age each received a total of 10 ug of recombinant protein, emulsified in Complete Freund's Adjuvant and delivered subcutaneously, followed by boosts of 1-10 ug of recombinant protein, emulsified in Incomplete Freund's Adjuvant, also administered subcutaneously, given at various intervals following the initial priming. A final dose of antigen was administered intraperitoneally, in phosphate buffered saline, in the absence of adjuvant. Alternative immunisation routes and procedures can also be employed. For example, different adjuvants or immune potentiating procedures may be used instead of Freund's adjuvant. DNA immunisations are often delivered intramuscularly or via a Genegun. Transfected cells or membrane preparations from such cells are often, although not exclusively, administered intraperitoneally.

1.4. Serum ELISA

During and following immunisation, serum was collected from mice and checked for the presence of heavy-chain antibody responses to the immunogen by ELISA. Nunc Maxisorp plates (Nunc Cat. No. 443404) were coated overnight at 4° C. with 50μl/well of a 5 μg recombinant antigen/ml of PBS solution. Following decanting of the antigen solution, plates were washed using PBS (prepared from PBS tablets, Oxoid cat no. BRO014G) supplemented with 0.05% Tween® 20 (sigma P1379), followed by washes with PBS without added Tween®. To block non-specific protein interactions, a solution of 3% skimmed milk powder (Marvel) in PBS was added to the wells and the plate was incubated for at least one hour at room temperature. Dilutions of serum in 3% skimmed milk powder/PBS were prepared in polypropylene tubes or plates and incubated for at least one hour at room temperature prior to transfer to the blocked ELISA plate where a further incubation of at least one hour took place. Unbound protein was then washed away using repetitive washes with PBS/Tween® followed by PBS. A solution of biotin-conjugated, goat anti mouse IgG, Fcgamma subclass 1 specific antibody (Jackson 115-065-205), prepared in PBS/3% μ was then added to each well and a further incubation at room temperature for at least one hour took place. Unbound detection antibody was removed by repeated washing using PBS/Tween® and PBS. Neutravidin-HRP solution (Pierce 31030) in 3% Marvel/PBS was then added to the ELISA plates and allowed to bind for at least 30 minutes. Following further washing, the ELISA was developed using TMB substrate (Sigma cat. no. T0440) and the reaction was stopped after 10 minutes by the addition of 0.5M $H_2SO_4$ solution (Sigma cat. no. 320501). Absorbances were determined by reading at 450 nm. Alternative assays, such as ELISPOT assays, may also be used to check for immunisation-induced heavy-chain antibody responses.

1.5. Generation of Libraries from Immunised Mice a. Processing Tissues, RNA Extraction and cDNA Manufacture Spleen, inguinal and brachial lymph nodes were collected into RNAlater from each immunised animal. For each animal, ⅓ of the spleen and 4 lymph nodes were processed separately. Initially, the tissues were homogenised; following transfer of tissues to Lysing matrix D bead tubes (MP Bio cat #116913100), 600 μl of RLT buffer containing β-mercaptoethanol (from Qiagen RNeasy® kit cat #74104) was added before homogenisation in a MP Bio Fastprep homogeniser (cat #116004500) using 6 m/s 40 seconds cycles. The tubes containing the homogenised tissues were transferred to ice and debris was pelleted by microcentrifugation at 10 g for 5 minutes. 400 μl of the supernatant was removed and used for RT-PCR.

Initially, RNA was extracted using Qiagen RNeasy® kit cat #74104 following the manufacturer's protocol. Each RNA sample was then used to make cDNA using Superscript III RT-PCR high-fidelity kit (Invitrogen cat #12574-035). For each spleen and LN RNA sample, 5 RT-PCR reactions were performed, each with VH_J/F (long) primer in combination with a primer for each $V_H$ family present. Mastermixes were prepared for the RT-PCR reactions, based on the following tube reaction components.

12.5 μl 2× reaction mix
0.5 μl forward primer (10 uM)
0.5 μl reverse primer (10 uM)
0.5 μl enzyme mix
500 ng-1 μg RNA
Up to 25 μl with water The RT-PCR reactions were carried out in a thermal cycler using the following conditions;

50° C. 20 min
94° C. 2 min
35 cycles of

94° C. 15 sec
58° C. 30 sec
68° C. 30 sec
68° C. 5 min
Hold at 4° C.

Products in the range of 370 bp were confirmed by gel electrophoresis.

For each mouse, the $V_H$ products amplified for a given family from the ⅓ spleen and each of the 4 lymph nodes were then pooled for purification using Thermo/Fermentas GeneJet PCR purification kit (cat #K0702) which was used according to the Manufacturer's instructions, with the products eluted in 50 μl of water.

b. Cloning into Phagemid Vector

The phagemid vector, pUCG3, was employed in these studies. As indicated, $V_H$ may be cloned into pUCG3, using conventional methods involving restriction enzyme digestions with NcoI and XhoI, ligation and transformation. Alternatively, a PCR-based method may be used to construct the $V_H$ phagemid libraries. Both of these procedures were used to generate libraries from the amplified $V_H$ sequences. The former method is widely used in the art. Phusion High fidelity PCR master mix with GC buffer (cat #F532L, NEB) was used for the PCR reactions which comprised the following reagents;

| Phusion GC 2x mix | 25 μl |
| pUCG3 | 5-10 ng |
| Primers (10uM) | 1.25 μl of each |
| DMSO | 1.5 μl |
| Nuclease-free $H_2O$ | to final volume of 50 μl |

The cycling conditions used were

98° C. 30 seconds
10 cycles of

98° C. 10 seconds
58° C. 20 seconds
68° C. 2 minutes, 30 seconds
20 cycles of

98° C. 10 seconds
58° C. 20 seconds
68° C. 3 minutes
68° C. 5 minutes
4° C. hold The PCR product (3152 bp) was gel purified using Fermentas GeneJet Gel purification kit (cat #K0691), according to the manufacturer's instructions, with final elution in 40 μl of elution buffer. The purified $V_H$ RT-PCR products were employed as megaprimers with the linearised pUCG3 to give phagemid products for transformation and library creation, based on the following reactions;

| Phusion GC 2x mix | 25 μl |
| Linearised pUCG3 | 700 ng |
| $V_H$ PCR product | 250 ng |
| DMSO | 1.5 μl |
| Nuclease-free $H_2O$ | to 50 μl final volume |

PCR was performed as follows;

| | |
|---|---|
| 98° C. 30 sec | |
| 98° C. 10 sec | |
| 58° C. 20 sec | 10 cycles |
| 72° C. 2 min | |
| 72° C. 5 min | |
| Hold at 10° C. | |

The products of PCR were analysed on a 1% agarose gel.

The various family $V_H$/phagemid products were purified using Ferment as PCR purification kit (cat #K0702) according to the manufacturer's instructions with the final elution being in 25 µl $H_2O$ and used for transformations of TG1 *E. coli* (Lucigen, Cat: 60502-2) by electroporation using Bio-Rad® 10×1 mm cuvettes (BioRad® cat #165-2089, a Eppendorf® Eporator and pre-warmed recovery medium (Lucigen, proprietary mix). 41 of the purified products were added to 25 ul of cells for the electroporation, with up to 10 electroporations being performed for each $V_H$/phagemid product at 1800v. Electroporated cells were pooled and recovered in 50 ml Falcon tubes incubated for 1 hour at 37° C. with shaking at 150 rpm. A 10-fold dilution series of an aliquot of the transformations was performed and plated in petri dishes containing 2×TY agar supplemented with 2% (w/v) glucose and 100 ug/ml ampicillin. Resulting colonies on these dishes were used to estimate the library size. The remainder of the transformation was plated on large format Bioassay dishes containing 2×TY agar supplemented with 2% (w/v) glucose and 100 ug/ml ampicillin. All agar plates were incubated overnight at 30° C. 10 ml of 2×TY broth was added to the large format bioassay dishes and colonies were scraped and OD600 measured (OD of 1.0=5×10$^8$ cells/ml). Aliquots were stored at −80° C. in cryovials after addition of 50% v/v glycerol solution (50%) or used directly in a phage selection process.

In some instances, clones were picked directly and sequence was determined to give an estimate of the diversity of the library. Typically, for each mouse a phage display library with greater than 1e8 recombinants was constructed to fully capture the $V_H$ diversity in that mouse. Naive $V_H$ libraries were then constructed. Preparation of library phage stocks and phage display selections were performed according to published methods (Antibody Engineering, Edited by Benny Lo, chapter 8, p161-176, 2004).

$V_H$ from the different selections were screened in using binding ELISA assays to identify specific $V_H$ with neutralising properties. $V_H$, both purified and crude periplasmic extracts, were also tested for their ability to inhibit the interaction of IL-17A with recombinant IL-17RA-Fc.

An assay was developed to measure the ability of IL-17A-binding $V_H$ to inhibit IL-17A-induced IL6 release from the cell line, HT1080 (ECACC cat #85111505). The cell line was maintained in exponential growth in MEM with Earles's salts, supplemented with non-essential amino acids, 10% FBS, 2 mM L-Glutamine and penicillin/streptomycin and incubated in a humidified incubator at 37° C., 5% $CO_2$. For the assay, 50,000 cells/well were seeded into a 96 flat bottomed tissue culture plate and cultured overnight. Serial dilution of purified $V_H$ were prepared and incubated at 37° C. for 1 hour with culture medium/PBS supplemented with 10 ng/ml IL-17A (Peprotech cat #AF200-17). Following incubation, the $V_H$/IL-17A mixture (or suitable controls) were transferred to the HT1080 cells (from which culture medium had been aspirated) and incubated for a further 5 hours in the $CO_2$ incubator. The cell culture supernatant was collected and assayed for IL6 using the IL-6 Duoset (R & D Systems, cat #DY206), following manufacturer's instructions. Binding kinetics of anti-IL-17A $V_H$ antibodies were measured on a BIAcore® T200 instrument. Following the above screening cascade, $V_H$ domain binding to IL-17A was identified that demonstrated inhibitory properties. This $V_H$ domain was optimised yielding a $V_H$ domain as identified in SEQ ID No. 1. Optimisation was carried out by aligning lead $V_H$ with other members of the same lineage to identify somatic hypermutation hot-spots targeted during the immune response. Optimised $V_H$ show improved affinities to IL-17 and improved potencies in the IL-17 cell based assay due to slower off-rates. The $V_H$ domains as disclosed herein were characterised to establish binding specificity by ELISA as described above. A number of $V_H$ domains, including that identified in SEQ ID NO: 1 were shown to have good binding properties to human IL-17A. $V_H$s identified were shown not to cross-react with close relatives such as IL-17C and IL-17F. The nucleic acid encoding for SEQ ID NO: 1 is shown below.

(SEQ ID NO: 76)
GAGGTTCAGTTGGTGGAAAGCGGCGGTGGCCTGGTCCAGCCGGGTGGTAG

CCTGCGCCTGTCCTGCGCGGCTAGCGGTTTCACGTTTAGCAGCTACAGCA

TGTACTGGGTGCGTCAAGCGCCAGGCAAAGGTCTGGAATGGGTTGCCGAG

ATTAAGCAAGACGGTTCTGTTCAGTATTATGTCAGCGACGTGAAGGGTCG

TTTTACCATCAGCCGTGACAACGCGAAAAACAGCCTGTATTTGCAGATGA

ATTCCCTGCGCGCTGAAGATACCGCGGTGTATTACTGTGCGAAAGGTGAG

ATTCTGCCGCTGTACTTCGATTACTGGGGCCAAGGCACCCTGGTTACTGT

CTCGAGC

Example 2 Drug Substance Excipient Screening 2.1. Making the Drug Substance Buffer Formulation: Concentration of Various Parts of the Composition and pH Initial compatibility screening using $V_H$1.1 (SEQ ID NO: 74) was carried out to identify optimal drug substance buffer excipients and optimal pH. The optimal pH range for $V_H$1.1 was identified as pH 7.5 to 8.5, preferably 8.0. Screening studies followed by design of experiments (DOE) was then used to examine $V_H$1.1 formulated in a number of different buffer species at different concentrations at this pH.

Formulation screening studies were initially performed under accelerated conditions (high temperature). Analysis was performed using visual appearance, UV analysis (concentration and light scattering), SE-HPLC, NR SDS PAGE, RP HPLC, AIEX and binding ELISA. $V_H$1.1 was tested in an initial accelerated stability study to evaluate buffers across a broad pH range. These were then also tested with and without five excipients at a single concentration. It was observed that higher pH (about pH8.0) buffers improved the stability of CB001 as measured by SE-HPLC and AIEX-HPLC and ELISA. Of the excipients tested in this screen Propylene Glycol was shown to also increase stability of the product. Stability was confirmed by extending the study to 1 month at 2-8° C., where no degradation was observed.

A further accelerated, screening, stability study was then undertaken with alternatives buffers around the optimal pH with and without further excipients to be tested. Of the buffer only samples Tris/Glycine and Phosphate/Citrate were shown to improve stability over the other buffers tested. A concentration of 100 mM was also shown to give a higher stability. From this study the two buffer systems were further tested in a DoE study. This evaluated the buffer with varying levels of one of four different excipients (Propylene Glycol, L-Arginine/L-Glutamic acid, Poloxamer and Sorbitol). Tris-Glycine was then chosen as the final buffer system as it showed more consistently stable monomer levels over the phosphate/citrate system. From the DoE analysis the following formulation was predicted to be the most stable: 100 mM Tris/glycine, 125 mM Arg/glu, 10% sorbitol, 15% propylene glycol pH8.0. This was then further tested in a six week accelerated stability study against 3 other combinations predicted to be stable following the DoE analysis. The different formulations were tested in an accelerated stability study and examined by SE-UPLC, UV A280 nm & visual appearance. Following statistical modelling the four most optimal drug substance buffer (DSB) formulations (as shown in Table 2a see also 2b) were selected.

As used herein, the term Drug Substance Buffer refers to the inactive buffer without the active IL-17 binding molecule. As used herein, the term Drug Substance (DS) refers to a formulation comprising the active molecule binding to human IL17A and Drug Substance Buffer.

TABLE 2a

Optimal formulation buffers from initial DOE

| Formulation # | Formulation buffer details |
|---|---|
| 1 | 100 mM Tris/Glycine, 125 mM L-Arginine/Glutamic acid, 6% Propylene Glycol, 10% Sorbitol, pH 8.0 |
| 2 | 100 mM Tris/Glycine, 80 mM L-Arginine/Glutamic acid, 15% Propylene Glycol, 10% Sorbitol, pH 8.0 |
| 3 | 100 mM Tris/Glycine, 125 mM L-Arginine/Glutamic acid, 6% Propylene Glycol, 5% Trehalose dihydrate, pH 8.0 |
| 4 | 100 mM Tris/Glycine, 150 mM L-Arginine/Glutamic acid, 7% Propylene Glycol, pH 8.0 |

Formulation 1 was formulated as shown below.

TABLE 2b

Formulation of #1

| Buffer component | Molecular weight (g/mol or Daltons) | Target concentration | Amount to add to H₂0 for one litre final volume |
|---|---|---|---|
| Trizma base | 121.1 | 100 mM | 12.1 g |
| Glycine | 75.1 | 100 mM | 7.5 g |
| L-Arginine | 174.2 | 125 mM | 21.8 g |
| L-Glutamic acid | 147.1 | 125 mM | 18.4 g |
| D-Sorbitol | 182.2 | 10% | 100 g |
| Propylene glycol | 76.1 | 6% | 60 mL |

Following addition of all components, pH adjust to 8.0 with HCl or NaOH as required.

The four combinations as shown in table 2 were tested on a 6 week accelerated stability study and analyzed using SE-UPLC, AIEX-HPLC, RP-HPLC, UV A280 nm, SDS PAGE & ELISA. The experimental data demonstrated that a formulation comprising 100 mM Tris/Glycine, 125 mM L-Arginine/Glutamic acid, 6% Propylene Glycol, 10% Sorbitol, pH 8.0 was stable and showed reduced aggregation see FIG. 1.

2.2. Longer Term Stability Screening for DS

A large scale batch of $V_H$ 1.1 was manufactured at 40 mg/mL in 100 mM Tris/Glycine, 125 mM L-Arginine/ Glutamic acid, 6% Propylene Glycol, 10% Sorbitol, pH 8.0 (DS) and put on long term stability at multiple temperatures. Samples were analysed for: pH, UV A280 nm, SE-UPLC, RP-UPLC, AIEX-HPLC, SDS PAGE, ELISA, endotoxin and bioburden. Example data demonstrating good stability of the DS at 2-8° C. storage over 3 months is shown in FIG. 2 and FIG. 3.

$V_H$1.1 at 40 mg/mL in drug substance buffer showed osmolality of 2,386 mOsm/kg measured using osmolality by freezing point depression which is higher than physiological levels. Normal osmolality of blood/serum is about 300-310 mOsm/L.

Example 3 Further Development of the Formulation for Topical Administration 3.1 Compatibility Testing Excipients/formulation components were tested for compatibility with the active molecule for use with a topical formulation on an accelerated stability study, assed using SE-HPLC. Formulations were further tested in stability and efficacy studies see Table 3 and Table 4.

TABLE 3

Top seven shortlisted topical formulations-parent compositions

| Material | 1 | 2 | 3 | 4 | 5 | 6 | 7 |
|---|---|---|---|---|---|---|---|
| Drug Substance Buffer | 100% | 60% | 50% | 70% | 70% | 50% | |
| Transcutol HP | | 40% | | | | | 50% |
| Propylene Glycol | | | 50% | | | | 20% |
| Steareth-20 | | | | 5% | 3% | 9% | 5% |
| Steareth-2 | | | | 5% | 7% | 21% | 5% |
| Octyldodecanol | | | | | 20% | 20% | 20% |
| Isopropyl Myristate | | | | 20% | | | |
| Total | 100% | 100% | 100% | 100% | 100% | 100% | 100% |

TABLE 4

Top seven shortlisted topical drug substance (DS) formulations-active compositions

| Material | 1 | 2 | 3 | 4 | 5 | 6 | 7 |
|---|---|---|---|---|---|---|---|
| Parent Formulation | 50% | 50% | 50% | 50% | 50% | 50% | 50% |
| Drug Substance (40 mg/mL) | 50% | 50% | 50% | 50% | 50% | 50% | 50% |
| Total | 100% | 100% | 100% | 100% | 100% | 100% | 100% |
| [VH 1.1] (mg/mL) | 20 | 20 | 20 | 20 | 20 | 20 | 20 |

TABLE 5

Final concentration of Drug substance buffer component in the top seven shortlisted topical formulations as shown in table 3

| Material | | 1 | 2 | 3 | 4 | 5 | 6 | 7 |
|---|---|---|---|---|---|---|---|---|
| Tris/Glycine | mM | 100 | 80 | | 75 | 85 | 85 | 75 |
| L-Arginine/ Glutamic acid | mM | 125 | 100 | | 93.75 | 106.25 | 106.25 | 93.75 |
| Propylene Glycol | % | 6 | 4.8 | 29.5 | 5.1 | 5.1 | 4.5 | |
| Sorbitol | % | 10 | 8 | | 7.5 | 8.5 | 8.5 | 7.5 |

Where Drug Substance Buffer is 100 mM Tris/Glycine, 125 mM L-Arginine/Glutamic acid, 6% Propylene Glycol, 10% Sorbitol, pH 8.0 and Drug Substance is 40 mg/mL $V_H$ 1.1 in Drug Substance Buffer. These were assessed by an accelerated stability study using SE-HPLC and efficacy and penetration efficiency using an in vitro 3D skin construct (see also section 2.2).

These studies demonstrated that formulations 1-6 all showed in vitro efficacy and penetration and formulations 1, 2 and 3 showed superior penetration with 1 and 3 the highest stability.

3.2 In Vitro Efficacy: MatTek Model (In Vitro Efficacy of DS and Other Formulations)

A model based on MatTek's 3D psoriatic tissue model (Ayehunie, 2012) was used. The psoriasis tissue model is cultured using normal human epidermal keratinocytes and psoriatic fibroblasts. The reconstructed psoriasis tissues adopt a psoriatic phenotype as evidenced by increased basal cell proliferation, expression of psoriasis-associated biomarkers, and elevated cytokine release (MatTek Corporation, 2016). The MatTek's 3D psoriatic tissue model modified by addition of IL-17A was used for efficacy testing of $V_H$ 1.1 in a test buffer and drug substance buffer.

It was demonstrated that addition of IL-17A to the model (via the culture medium) further upregulated the psoriatic phenotype as evidenced by gene expression (significant upregulation (>2 fold) Gene expression was noted for CCL20, CXCL5, HBD-2, IL-8 and psoriasin) and cytokine/chemokine release (significant increases in cytokine/chemokine production were noted for CCL20, CXCL6, IL-6, IL-8 and TNF-α). This upregulated model was then used to test for efficacy of the $V_H$ 1.1 in this model.

Figure 5:
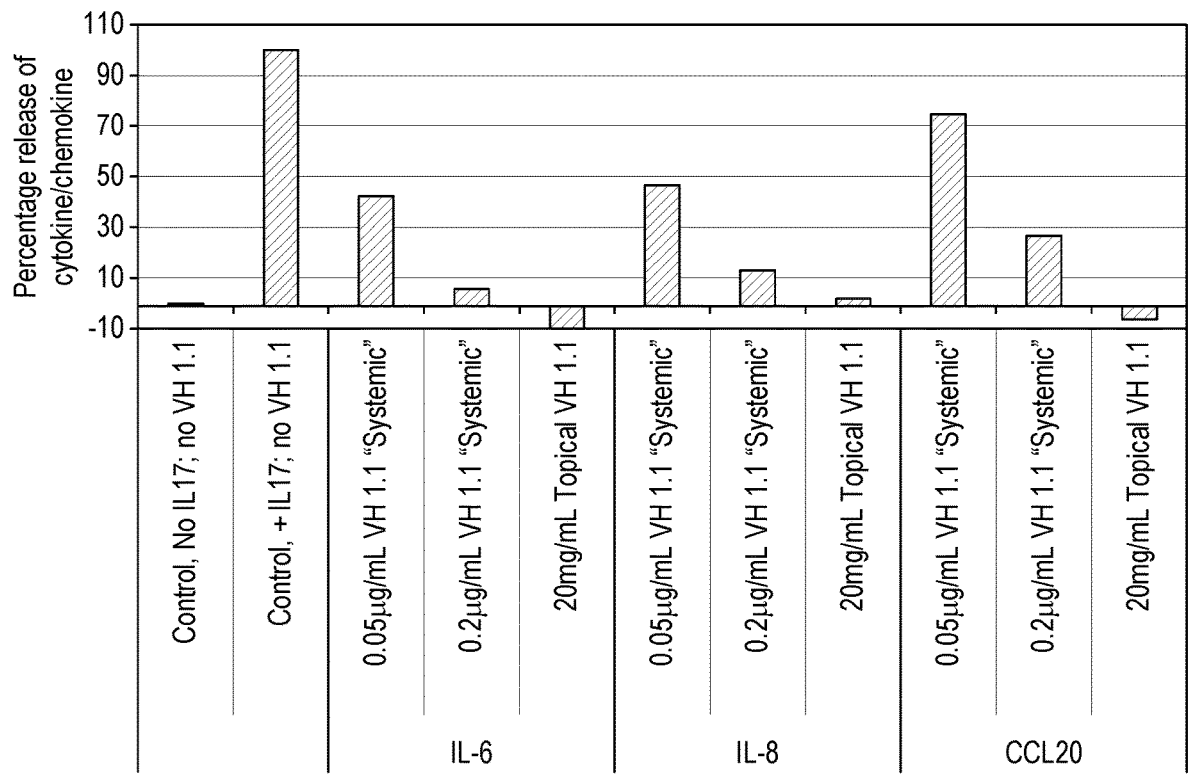

Tissues were exposed either topically or systemically (i.e. basolateral delivery via addition the culture media or to the apical surface of the tissue construct) to $V_H$ 1.1 in a preliminary buffer (50 mM Tricine) pH8.0. Tissues were treated over 4 days and assessed at 48 and 96 hours. For gene analysis, RNA was isolated using standard RNA isolation protocol. Quantitative RT-PCR was performed to determine expression levels of 6 psoriatic and skin associated genes. Additionally chemokine/cytokine levels were assessed using commercially available kits. This demonstrated that these psoriatic markers could all be significantly reduced thus demonstrating efficacy of $V_H$ 1.1 in the model (FIG. 4 and FIG. 5).

CCL20 was chosen for use in further studies of the topical formulations as it showed a clear dose dependant effect and is a clinically relevant biomarker. The study was then expanded to further evaluate the dose required to have an effect when $V_H$ 1.1 was added topically (as Drug Substance as described above).

$V_H$ 1.1 was added daily, over 4 days, followed by media exchange 24 hrs later as detailed in Table 6. Media was stored at −80° C. until analysis.

TABLE 6

Experimental design used for topical addition in MatTek model

| Time = 0 | Time = 6 hours | Time = 24 hours | Time = 48 hours | Time = 72 hours | Time = 96 hours |
|---|---|---|---|---|---|
|  |  | Harvest media | Harvest media | Harvest media | Harvest media and skin |
| Topical addition of $V_H$ 1.1 100 μl |  | Topical addition of $V_H$ 1.1 100 μl | Topical addition of $V_H$ 1.1 100 μl | Topical addition of $V_H$ 1.1 100 μl |  |
|  | IL-17A addition | Fresh media addition | Fresh media addition | Fresh media addition |  |

TABLE 6-continued

Experimental design used for topical addition in MatTek model

| Time = 0 | Time = 6 hours | Time = 24 hours | Time = 48 hours | Time = 72 hours | Time = 96 hours |
|---|---|---|---|---|---|
|  |  | to media containing IL-17A | containing IL-17A | containing IL-17A |  |

Subsequent study then demonstrated that CCL20 was inhibited even by low dose topical addition of $V_H$ 1.1 in a test buffer (50 mM Tricine) pH8.0 (FIG. 8) and this study design was used to compare 7 drug product (DP) formulations (FIG. 9).

$V_H$ 1.1 was formulated according to tables 2 to 4. Penetration of the tissue construct was then measured either using a FRET assay as described in FIG. 6, or a Gyros assay using a biotinylated type 2 anti idiotype Fab (binds $V_H$ 1.1 with or without IL-17A) captured using a streptavidin coated bead. Detection is then with a fluorophore labelled rabbit anti $V_H$ 1.1 pAb as FIG. 7.

A Fluorescence Resonance Energy Transfer (FRET) complex is formed from binding of biotinylated IL-17 $V_H$ to a rabbit polyclonal anti $V_H$ antibody. Detection of this interaction is carried out using streptavidin europium-cryptate as the donor fluorophore and goat anti rabbit-Alexa Fluor-647 as the acceptor fluorophore in the FRET complex. Once the complex is formed excitation of the donor fluorophore results in FRET to the acceptor fluorophore due to their close proximity. The time resolved acceptor fluorescence emission is then measured.

The assay can be used to detect non biotinylated IL-17 $V_H$ in a competition format. The IL-17 $V_H$ competes with biotinylated IL-17 $V_H$ for binding to the rabbit polyclonal anti $V_H$ antibody resulting in a reduced fluorescence emission from the acceptor fluorophore. The degree of competition is dependent on the concentration of the IL-17 $V_H$. The amount of $V_H$ present in a test sample is quantified using a standard curve of emission signal in the presence of known concentrations of purified IL-17 $V_H$. Due to the competitive assay format the linear range for quantification if limited thus samples are tested at multiple dilutions to ensure they are within this range.

Formulations 1-6 all showed good skin penetration, with formulations 1-3 demonstrating the highest level of skin penetration (FIG. 10).

Example 4. Additional Drug Product Development

Additional development was undertaken with Transcutol® (penetration enhancer from formulation 2); Propylene Glycol (penetration enhancer from formulation 3).

An initial accelerated stability study (as assayed with SE-UPLC) was carried out with different concentrations of these excipients and $V_H$ 1.1 in drug substance buffer, to determine a practical range that was used in a DOE. In addition, the range of poloxamer 407 that was required to produce a light gel was determined. Where Drug Substance Buffer is 100 mM Tris/Glycine, 125 mM L-Arginine/Glutamic acid, 6% Propylene Glycol, 10% Sorbitol, pH 8.0; with components adjusted accordingly. Where PG was added the value as shown in Table 7 was the final concertation adjusted to include the amount already in the DSB.

Following this, two formulations with different $V_H$ concentration (at 20 mg/mL and 30 mg/mL respectively) plus the Drug Substance (at 20, 30 and 40 mg/mL respectively) (Table 7) were chosen to put on long term stability, as measured by SE-UPLC and AIEX-HPLC.

TABLE 7

Drug Product formulations

| Formulation # | Concentration of $V_H$ 1.1 | Total % v/v PG | % w/w Poloxamer |
|---|---|---|---|

```
<400> SEQUENCE: 2

Ser Tyr Ser Met Tyr
1               5

<210> SEQ ID NO 3
<211> LENGTH: 17
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: CDR2 of SEQ ID NO.1

<400> SEQUENCE: 3

Glu Ile Lys Gln Asp Gly Ser Val Gln Tyr Tyr Val Ser Asp Val Lys
1               5                   10                  15

Gly

<210> SEQ ID NO 4
<211> LENGTH: 10
<212> TYPE: PRT
<213> ORGANISM: Homo sapiens
<220> FEATURE:
<221> NAME/KEY: MISC_FEATURE
<222> LOCATION: (1)..(10)
<223> OTHER INFORMATION: CDR3 of SEQ ID NO.1

<400> SEQUENCE: 4

Gly Glu Ile Leu Pro Leu Tyr Phe Asp Tyr
1               5                   10

<210> SEQ ID NO 5
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu His Phe Asp Tyr Trp Gly Gln Gly
            100                 105                 110

Thr Leu Val Thr Val Ser Ser
        115

<210> SEQ ID NO 6
<211> LENGTH: 119
<212> TYPE: PRT
<213> ORGANISM: Homo sapiens
```

```
<220> FEATURE:
<221> NAME/KEY: MISC_FEATURE
<222> LOCATION: (1)..(119)
<223> OTHER INFORMATION: IL17 binding single doamin antibody

<400> SEQUENCE: 6
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Asp Gly Ser Val Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

```
<210> SEQ ID NO 7
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 7
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Thr Gly Ser Val Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

```
<210> SEQ ID NO 8
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 8
```

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Pro Thr Gly Ser Val Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115

<210> SEQ ID NO 9
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115

<210> SEQ ID NO 10
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 10

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val

```
                35                  40                  45
Ala Lys Ile Glu Gln Asp Gly Ser Glu Glu Tyr Tyr Val Asp Ser Val
 50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp Tyr Trp Gly Gln Gly
                100                 105                 110

Thr Leu Val Thr Val Ser Ser
            115

<210> SEQ ID NO 11
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 11

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Gly Met Tyr Trp Val Arg Gln Ala Pro Gly Lys Gly Leu Glu Trp Val
                 35                  40                  45

Ala Lys Ile Glu Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp Tyr Trp Gly Gln Gly
                100                 105                 110

Thr Leu Val Thr Val Ser Ser
            115

<210> SEQ ID NO 12
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 12

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Gly Met Tyr Trp Val Arg Gln Ala Pro Gly Lys Gly Leu Glu Trp Val
                 35                  40                  45

Ala Glu Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80
```

Leu Gln Met Asn Ser Leu Arg Ala Glu Asp Thr Ala Val Tyr Tyr Cys
              85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 13
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Ser Ile Glu Gln Asp Gly Ser Glu Tyr Tyr Val Asp Ser Val
    50                  55                  60

Lys Gly Arg Phe Thr Ile Ser Arg Asp Asn Ala Lys Lys Ser Leu Phe
65                  70                  75                  80

Leu Gln Met Asn Ser Leu Arg Ala Glu Asp Thr Ala Val Tyr Tyr Cys
              85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 14
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Tyr Trp Val Arg Gln Ala Pro Gly Lys Gly Leu Glu Trp Val
        35                  40                  45

Ala Ser Ile Lys Gln Asp Gly Ser Glu Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
              85                  90                  95

Ala Lys Gly Glu Ile Leu Pro Leu Tyr Phe Asp Tyr Trp Gly Gln Gly
            100                 105                 110

```
Thr Leu Val Thr Val Ser Ser
        115

<210> SEQ ID NO 15
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Lys Ile Glu Gln Asp Gly Ser Glu Glu Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Gly Glu Ile Leu Pro Leu Tyr Phe Asp Tyr Trp Gly Gln Gly
        100                 105                 110

Thr Leu Val Thr Val Ser Ser
        115

<210> SEQ ID NO 16
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Ser Ile Glu Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Gly Glu Ile Leu Pro Leu Tyr Phe Asp Tyr Trp Gly Gln Gly
        100                 105                 110

Thr Leu Val Thr Val Ser Ser
        115

<210> SEQ ID NO 17
<211> LENGTH: 119
<212> TYPE: PRT
```

<213> ORGANISM: Homo sapiens
<220> FEATURE:
<221> NAME/KEY: MISC_FEATURE
<223> OTHER INFORMATION: IL17 binding single domain antibody

<400> SEQUENCE: 17

```
Glu Val Gln Leu Val Glu Ser Gly Gly Gly Leu Val Gln Arg Gly Gly
1               5                   10                  15
Ser Leu Arg Leu Ser Cys Ala Ala Ser Gly Phe Thr Phe Ser Ser Tyr
            20                  25                  30
Arg Met Tyr Trp Val Arg Gln Ala Pro Gly Lys Gly Leu Glu Trp Val
        35                  40                  45
Ala Ser Ile Glu Gln Asp Gly Ser Glu Gly Tyr Tyr Val Asp Ser Val
    50                  55                  60
Lys Gly Arg Phe Thr Ile Ser Arg Asp Asn Ala Lys Lys Ser Leu Phe
65                  70                  75                  80
Leu Gln Met Asn Ser Leu Arg Ala Glu Asp Thr Ala Val Tyr Tyr Cys
                85                  90                  95
Ala Lys Gly Glu Ile Leu Pro Leu Tyr Phe Asp Tyr Trp Gly Gln Gly
            100                 105                 110
Thr Leu Val Thr Val Ser Ser
        115
```

<210> SEQ ID NO 18
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 18

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ser Met Tyr Trp Val Arg Gln Ala Pro Gly Lys Gly Leu Glu Trp Val
        35                  40                  45
Ala Glu Ile Arg Gln Asp Gly Ser Glu Gln Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Lys Gly Glu Ile Leu Pro Leu Tyr Phe Asp Tyr Trp Gly Gln Gly
            100                 105                 110
Thr Leu Val Thr Val Ser Ser
        115
```

<210> SEQ ID NO 19
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Gly Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115
```

<210> SEQ ID NO 20
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Pro Thr Gly Ser Val Gln Tyr Tyr Val Ser Asp Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115
```

<210> SEQ ID NO 21
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
```

```
                35                  40                  45
Ala Glu Ile Lys Gln Asp Gly Ser Val Gln Tyr Tyr Val Gly Gly Val
            50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Lys Gly Glu Ile Leu Pro Leu Tyr Phe Asp Tyr Trp Gly Gln Gly
            100                 105                 110
Thr Leu Val Thr Val Ser Ser
            115

<210> SEQ ID NO 22
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 22

Glu Val Gln Leu Val Glu Ser Gly Gly Gly Leu Val Gln Pro Gly Gly
1               5                   10                  15
Ser Leu Arg Leu Ser Cys Ala Thr Ser Gly Phe Thr Phe Ser Ser Tyr
            20                  25                  30
Gly Met Tyr Trp Val Arg Gln Ala Pro Gly Lys Gly Leu Glu Trp Val
            35                  40                  45
Ala Glu Ile Lys Gln Asp Gly Ser Glu Lys Tyr Tyr Val Asp Ser Val
            50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Lys Gly Glu Ile Leu Pro Leu Tyr Phe Asp Tyr Trp Gly Gln Gly
            100                 105                 110
Thr Leu Val Thr Val Ser Ser
            115

<210> SEQ ID NO 23
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 23

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Gly Met Tyr Trp Val Arg Gln Ala Pro Gly Lys Gly Leu Glu Trp Val
            35                  40                  45
Ala Lys Ile Glu Gln Asp Gly Ser Glu Glu Tyr Tyr Ala Asp Ser Val
            50                  55                  60
Lys Gly Arg Phe Thr Ile Ser Arg Asp Asn Ala Lys Lys Ser Leu Tyr
65                  70                  75                  80
```

-continued

```
Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 24
<211> LENGTH: 119
<212> TYPE: PRT
<213> ORGANISM: Homo sapiens
<220> FEATURE:
<221> NAME/KEY: MISC_FEATURE
<223> OTHER INFORMATION: IL17 binding single domain antibody

<400> SEQUENCE: 24

Glu Val Gln Leu Val Glu Ser Gly Gly Gly Leu Val Leu Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Glu Ile Lys Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 25
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 25

Glu Val Gln Leu Val Glu Ser Gly Gly Gly Leu Val Arg Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Lys Ile Glu Gln Asp Gly Ser Glu Glu Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
```

-continued

```
<210> SEQ ID NO 26
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 26

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Glu Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 27
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 27

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Glu Ile Lys Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 28
<211> LENGTH: 119
<212> TYPE: PRT
<213> ORGANISM: Homo sapiens
```

-continued

```
<220> FEATURE:
<221> NAME/KEY: MISC_FEATURE
<222> LOCATION: (1)..(119)
<223> OTHER INFORMATION: IL17 binding single domain antibody

<400> SEQUENCE: 28
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Tyr Trp Val Arg Gln Ala Pro Gly Lys Gly Leu Glu Trp Val
        35                  40                  45

Ala Ser Ile Lys Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

```
<210> SEQ ID NO 29
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 29
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Arg Ile Gly Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

```
<210> SEQ ID NO 30
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 30
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
            35                  40                  45

Ala Ser Ile Glu Gln Asp Gly Ser Glu Glu Tyr Tyr Val Asp Ser Val
            50                  55                  60

Lys Gly Arg Phe Thr Ile Ser Arg Asp Asn Ala Lys Lys Ser Leu Phe
65                  70                  75                  80

Leu Gln Met Asn Ser Leu Arg Ala Gly Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115

<210> SEQ ID NO 31
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
            35                  40                  45

Ala Ser Ile Glu Gln Asp Gly Ser Glu Glu Tyr Tyr Val Asp Ser Val
            50                  55                  60

Lys Gly Arg Phe Thr Ile Ser Arg Asp Asn Ala Lys Lys Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Ala Val Ser Ser
            115

<210> SEQ ID NO 32
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val

```
                35                  40                  45

Ala Ser Ile Asp Gln Asp Gly Ser Glu Glu Tyr Tyr Val Asp Ser Val
             50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115

<210> SEQ ID NO 33
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 33

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Arg Met Tyr Trp Val Arg Gln Ala Pro Gly Lys Gly Leu Glu Trp Val
            35                  40                  45

Ala Ser Ile Asp Gln Asp Gly Ser Glu Glu Tyr Tyr Val Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115

<210> SEQ ID NO 34
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 34

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Asn Met Tyr Trp Val Arg Gln Ala Pro Gly Lys Gly Leu Glu Trp Val
            35                  40                  45

Ala Asn Ile Glu Gln Asp Gly Ser Glu Glu Tyr Tyr Val Asp Ser Val
         50                  55                  60

Lys Gly Arg Phe Thr Ile Ser Arg Asp Asn Ala Lys Asn Ser Leu Tyr
 65                  70                  75                  80
```

Leu Gln Met Asn Ser Leu Arg Ala Glu Asp Thr Ala Val Tyr Tyr Cys
            85                  90                  95

Ala Lys Gly Glu Ile Leu Pro Leu Tyr Phe Asp Tyr Trp Gly Gln Gly
        100                 105                 110

Thr Leu Val Thr Val Ser Ser
        115

<210> SEQ ID NO 35
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 35

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Gly Ile Glu Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Gly Glu Ile Leu Pro Leu Tyr Phe Asp Tyr Trp Gly Gln Gly
        100                 105                 110

Thr Leu Val Thr Val Ser Ser
        115

<210> SEQ ID NO 36
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Gly Ile Glu Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Gly Glu Ile Leu Pro Leu Tyr Phe Asp Tyr Trp Gly Gln Gly
        100                 105                 110

```
Thr Leu Val Thr Val Ser Ser
        115

<210> SEQ ID NO 37
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Gly Ile Glu Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 38
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Gly Ile Glu Gln Asp Gly Ser Glu Lys Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 39
<211> LENGTH: 119
<212> TYPE: PRT
```

```
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Gly Ile Glu Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 40
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Arg Ile Glu Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 41
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 41
```

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
            35                  40                  45

Ala Asn Ile Lys Gln Asp Gly Ser Glu Glu Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 42
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
            35                  40                  45

Ala Asn Ile Lys Gln Asp Gly Ser Glu Glu Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 43
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Met Phe Ser Ser Tyr
            20                  25                  30

-continued

```
Gly Met Tyr Trp Val Arg Gln Ala Pro Gly Lys Gly Leu Glu Trp Val
            35                  40                  45

Ala Asn Ile Glu Gln Asp Gly Ser Glu Lys Tyr Tyr Val Asp Ser Val
 50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu His Phe Asp Tyr Trp Gly Gln Gly
            100                 105                 110

Thr Leu Val Thr Val Ser Ser
            115
```

<210> SEQ ID NO 44
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 44

```
Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Met Phe Ser Ser Tyr
             20                  25                  30

Gly Met Tyr Trp Val Arg Gln Ala Pro Gly Lys Gly Leu Glu Trp Val
            35                  40                  45

Ala Asn Ile Glu Gln Asp Gly Ser Glu Lys Tyr Tyr Val Asp Ser Val
 50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu His Phe Asp Tyr Trp Gly Gln Gly
            100                 105                 110

Thr Leu Val Thr Val Ser Ser
            115
```

<210> SEQ ID NO 45
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 45

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Gly Met Tyr Trp Val Arg Gln Ala Pro Gly Lys Gly Leu Glu Trp Val
            35                  40                  45

Ala Asn Ile Lys Gln Asp Gly Ser Glu Gln Tyr Tyr Val Asp Ser Val
 50                  55                  60

Lys Gly Arg Phe Thr Ile Ser Arg Asp Asn Ala Lys Lys Ser Leu Tyr
```

65                  70                  75                  80

Leu Gln Met Asn Ser Leu Arg Ala Glu Asp Thr Ala Val Tyr Tyr Cys
                    85                  90                  95

Ala Lys Gly Glu Ile Leu Pro Leu His Phe Asp Tyr Trp Gly Gln Gly
                100                 105                 110

Thr Leu Val Thr Val Ser Ser
            115

<210> SEQ ID NO 46
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
                20                  25                  30

Ser Met Tyr Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Lys Gly Glu Ile Leu Pro Leu His Phe Asp Tyr Trp Gly Gln Gly
                100                 105                 110

Thr Leu Val Thr Val Ser Ser
            115

<210> SEQ ID NO 47
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ser Met Tyr Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                    85                  90                  95

Ala Lys Gly Glu Ile Leu Pro Leu Tyr Phe Asp His Trp Gly Gln Gly
                100                 105                 110

```
Thr Leu Val Thr Val Ser Ser
        115

<210> SEQ ID NO 48
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 48

Glu Val Gln Leu Val Glu Ser Gly Gly Gly Leu Val Gln Arg Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Gln Phe Asp Tyr Trp Gly Gln Gly
            100                 105                 110

Thr Leu Val Thr Val Ser Ser
        115

<210> SEQ ID NO 49
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 49

Glu Val Gln Leu Val Glu Ser Gly Gly Gly Leu Val Gln Arg Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Gln Phe Asp Tyr Trp Gly Gln Gly
            100                 105                 110

Thr Leu Val Thr Val Ser Ser
        115

<210> SEQ ID NO 50
<211> LENGTH: 119
```

```
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 50
```

Gln Val Gln Leu Val Glu Ser Gly Gly Gly Leu Val Gln Arg Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Gln Phe Asp Tyr Trp Gly Gln Gly
            100                 105                 110

Thr Leu Val Thr Val Ser Ser
        115

```
<210> SEQ ID NO 51
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 51
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Gln Phe Asp Tyr Trp Gly Gln Gly
            100                 105                 110

Thr Leu Val Thr Val Ser Pro
        115

```
<210> SEQ ID NO 52
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody
```

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Tyr Trp Val Arg Gln Ala Pro Gly Lys Gly Leu Glu Trp Val
        35                  40                  45

Ala Glu Ile Lys Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp His Trp Gly Gln Gly
            100                 105                 110

Thr Leu Val Thr Val Ser Ser
        115

<210> SEQ ID NO 53
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ile Trp Val Arg Gln Ala Pro Gly Lys Gly Leu Glu Trp Val
        35                  40                  45

Ala Asp Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Val Leu Pro Leu Tyr Phe Asp Tyr Trp Gly Gln Gly
            100                 105                 110

Thr Leu Val Thr Val Ser Ser
        115

<210> SEQ ID NO 54
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ser Met Ile Trp Val Arg Gln Ala Pro Gly Lys Gly Leu Glu Trp Val
        35                  40                  45

Ala Asp Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Val Leu Pro Leu Tyr Phe Asp Tyr Trp Gly Gln Gly
            100                 105                 110

Thr Leu Val Thr Val Ser Ser
            115
```

<210> SEQ ID NO 55
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 55

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Asn Met Tyr Trp Val Arg Gln Ala Pro Gly Lys Gly Leu Glu Trp Val
        35                  40                  45

Ala Glu Ile Asp Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp His Trp Gly Gln Gly
            100                 105                 110

Thr Leu Val Thr Val Ser Ser
            115
```

<210> SEQ ID NO 56
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 56

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Asn Met Tyr Trp Val Arg Gln Ala Pro Gly Lys Gly Leu Glu Trp Val
        35                  40                  45

Ala Glu Ile Asp Gln Asp Gly Ser Glu Lys Tyr Tyr Val Asp Ser Val
 50                  55                  60
```

```
Lys Gly Arg Phe Thr Ile Ser Arg Asp Asn Ala Lys Asn Ser Leu Phe
 65                  70                  75                  80

Leu Gln Met Asn Ser Leu Arg Ala Glu Asp Thr Ala Val Tyr Tyr Cys
             85                  90                  95

Ala Lys Gly Glu Ile Leu Pro Leu Tyr Phe Asp His Trp Gly Gln Gly
            100                 105                 110

Thr Leu Val Thr Val Ser Ser
            115
```

<210> SEQ ID NO 57
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 57

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Arg Met Tyr Trp Val Arg Gln Ala Pro Gly Lys Gly Leu Glu Trp Val
         35                  40                  45

Ala Ser Ile Glu Gln Asp Gly Ser Glu Glu Tyr Tyr Val Asp Ser Val
     50                  55                  60

Lys Gly Arg Phe Thr Ile Ser Arg Asp Asn Ala Lys Arg Ser Leu Phe
 65                  70                  75                  80

Leu Gln Met Ser Ser Leu Arg Ala Glu Asp Ser Ala Val Tyr Tyr Cys
             85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115
```

<210> SEQ ID NO 58
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 58

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Gln Met Tyr Trp Val Arg Gln Ala Pro Gly Lys Gly Leu Glu Trp Val
         35                  40                  45

Ala Gly Ile Glu Gln Asp Gly Ser Glu Glu Tyr Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Lys Gly Glu Ile Leu Pro Leu Tyr Phe Asp His Trp Gly Gln Gly
```

```
                         100                 105                 110
Thr Leu Val Thr Val Ser Ser
        115

<210> SEQ ID NO 59
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 59

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Glu Met Tyr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Lys Gly Glu Ile Leu Pro Leu His Phe Asp Tyr Arg Gly Gln Gly
            100                 105                 110

Thr Leu Val Thr Val Ser Ser
        115

<210> SEQ ID NO 60
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Leu Leu Tyr
65                  70                  75                  80

Leu Gln Met Asn Ser Leu Arg Val Glu Asp Thr Ala Val Tyr Tyr Cys
                85                  90                  95

Ala Lys Gly Glu Ile Leu Pro Leu Tyr Phe Asp Tyr Arg Gly Gln Gly
            100                 105                 110

Thr Leu Val Thr Val Ser Ser
        115

<210> SEQ ID NO 61
```

```
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 61
```

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Ser Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Lys Gly Glu Ile Leu Pro Leu His Phe Asp Tyr Arg Gly Gln Gly
            100                 105                 110

Thr Leu Val Thr Val Ser Ser
        115

```
<210> SEQ ID NO 62
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 62
```

Gln Val Gln Leu Val Glu Ser Gly Gly Gly Met Val Gln Pro Gly Gly
1               5                   10                  15

Ser Leu Arg Leu Ser Cys Ala Val Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Ser Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Lys Gly Glu Ile Leu Pro Leu His Phe Asp Tyr Arg Gly Gln Gly
            100                 105                 110

Thr Leu Val Thr Val Ser Ser
        115

```
<210> SEQ ID NO 63
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody
```

<400> SEQUENCE: 63

Gln Val Gln Leu Gln Glu Ser Gly Gly Asp Trp Val Gln Pro Gly Gly
1               5                   10                  15

Ser Leu Arg Leu Ser Cys Gly Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Lys Gln Asp Gly Thr Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro His Tyr Phe Asp Tyr Trp Gly Gln Gly
            100                 105                 110

Thr Leu Val Thr Val Ser Ser
        115

<210> SEQ ID NO 64
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Asn Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Glu Tyr Tyr Val Asp Ser Val
    50                  55                  60

Lys Gly Arg Phe Thr Ile Ser Arg Asp Asn Ala Arg Asn Ser Leu Tyr
65                  70                  75                  80

Leu Gln Met Ile Ser Leu Arg Ala Glu Asp Thr Ala Val Tyr Tyr Cys
                85                  90                  95

Ala Lys Gly Glu Ile Leu Pro Leu Tyr Phe Asp His Trp Gly Gln Gly
            100                 105                 110

Thr Leu Val Thr Val Ser Ser
        115

<210> SEQ ID NO 65
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Asn Tyr

```
                    20                  25                  30
Ser Met Tyr Trp Val Arg Gln Ala Pro Gly Lys Gly Leu Glu Trp Val
            35                  40                  45

Ala Asn Ile Lys Gln Asp Gly Ser Glu Glu Tyr Tyr Val Asp Ser Val
        50                  55                  60

Lys Gly Arg Phe Thr Ile Ser Arg Asp Asn Ala Arg Asn Ser Leu Tyr
 65                  70                  75                  80

Leu Gln Met Ile Ser Leu Arg Ala Glu Asp Thr Ala Val Tyr Tyr Cys
                85                  90                  95

Ala Lys Gly Glu Ile Leu Pro Leu Tyr Phe Asp His Trp Gly Gln Gly
            100                 105                 110

Thr Leu Val Thr Val Ser Ser
            115

<210> SEQ ID NO 66
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 66

Gln Val Gln Leu Val Glu Ser Gly Gly Gly Leu Val Gln Pro Gly Gly
 1               5                  10                  15

Ser Leu Arg Leu Ser Cys Thr Ala Ser Gly Phe Thr Phe Ser Asn Tyr
            20                  25                  30

Ser Met Tyr Trp Val Arg Gln Ala Pro Gly Lys Gly Leu Glu Trp Val
            35                  40                  45

Ala Asn Ile Lys Gln Asp Gly Ser Glu Glu Tyr Tyr Val Asp Ser Val
        50                  55                  60

Lys Gly Arg Phe Thr Ile Ser Arg Asp Asn Ala Arg Asn Ser Leu Tyr
 65                  70                  75                  80

Leu Gln Met Ile Ser Leu Arg Ala Glu Asp Thr Ala Val Tyr Tyr Cys
                85                  90                  95

Ala Lys Gly Glu Ile Leu Pro Leu Tyr Phe Asp His Trp Gly Gln Gly
            100                 105                 110

Thr Leu Val Thr Val Ser Ser
            115

<210> SEQ ID NO 67
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 67

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
            35                  40                  45

Ala Lys Ile Glu Gln Asp Gly Ser Glu Glu Tyr Tyr Val Asp Ser Val
        50                  55                  60
```

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115
```

<210> SEQ ID NO 68
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 68

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Lys Ile Glu Gln Asp Gly Ser Val Glu Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115
```

<210> SEQ ID NO 69
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 69

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gln Met Tyr Trp Val Arg Gln Ala Pro Gly Lys Gly Leu Glu Trp Val
        35                  40                  45

Ala Gly Ile Lys Gln Asp Gly Ser Glu Gln Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95
```

```
Ala Lys Gly Glu Ile Leu Pro Leu Tyr Phe Asp His Trp Gly Gln Gly
            100                 105                 110

Thr Leu Val Thr Val Ser Ser
        115

<210> SEQ ID NO 70
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Glu Ile Lys Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

<210> SEQ ID NO 71
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Gly Ile Glu Gln Asp Gly Ser Glu Glu Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115
```

-continued

```
<210> SEQ ID NO 72
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 72
```

Glu Val Gln Leu Val Glu Ser Gly Gly Gly Met Val Gln Pro Gly Gly
1               5                   10                  15

Ser Leu Arg Leu Ser Cys Ala Ala Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Glu Ile Glu Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

```
<210> SEQ ID NO 73
<211> LENGTH: 119
<212> TYPE: PRT
<213> ORGANISM: Homo sapiens
<220> FEATURE:
<221> NAME/KEY: MISC_FEATURE
<222> LOCATION: (1)..(119)
<223> OTHER INFORMATION: IL17 binding single domain antibody

<400> SEQUENCE: 73
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
        35                  40                  45

Ala Glu Ile Asn Gln Asp Gly Ser Glu Gln Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
        115

```
<210> SEQ ID NO 74
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
```

<223> OTHER INFORMATION: IL17 binding single domain antibody

<400> SEQUENCE: 74

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ser Met Tyr Trp Val Arg Gln Ala Pro Gly Lys Gly Leu Glu Trp Val
        35                  40                  45
Ala Glu Ile Lys Gln Asp Gly Ser Val Gln Tyr Tyr Val Ser Asp Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Lys Gly Glu Ile Leu Pro Leu Tyr Phe Asp Tyr Trp Gly Gln Gly
            100                 105                 110
Thr Leu Val Thr Val Ser Ser Ala
        115                 120
```

<210> SEQ ID NO 75
<211> LENGTH: 155
<212> TYPE: PRT
<213> ORGANISM: Homo sapiens
<220> FEATURE:
<221> NAME/KEY: MISC_FEATURE
<222> LOCATION: (1)..(155)
<223> OTHER INFORMATION: Human IL17

<400> SEQUENCE: 75

```
Met Thr Pro Gly Lys Thr Ser Leu Val Ser Leu Leu Leu Leu Leu Ser
1               5                   10                  15
Leu Glu Ala Ile Val Lys Ala Gly Ile Thr Ile Pro Arg Asn Pro Gly
            20                  25                  30
Cys Pro Asn Ser Glu Asp Lys Asn Phe Pro Arg Thr Val Met Val Asn
        35                  40                  45
Leu Asn Ile His Asn Arg Asn Thr Asn Thr Asn Pro Lys Arg Ser Ser
    50                  55                  60
Asp Tyr Tyr Asn Arg Ser Thr Ser Pro Trp Asn Leu His Arg Asn Glu
65                  70                  75                  80
Asp Pro Glu Arg Tyr Pro Ser Val Ile Trp Glu Ala Lys Cys Arg His
                85                  90                  95
Leu Gly Cys Ile Asn Ala Asp Gly Asn Val Asp Tyr His Met Asn Ser
            100                 105                 110
Val Pro Ile Gln Gln Glu Ile Leu Val Leu Arg Arg Glu Pro Pro His
        115                 120                 125
Cys Pro Asn Ser Phe Arg Leu Glu Lys Ile Leu Val Ser Val Gly Cys
    130                 135                 140
Thr Cys Val Thr Pro Ile Val His His Val Ala
145                 150                 155
```

<210> SEQ ID NO 76
<211> LENGTH: 357
<212> TYPE: DNA
<213> ORGANISM: Homo sapiens
<220> FEATURE:
<221> NAME/KEY: misc_feature
<222> LOCATION: (1)..(357)
<223> OTHER INFORMATION: nucleic acid encoding sequence 1

```
<400> SEQUENCE: 76
gaggttcagt tggtggaaag cggcggtggc ctggtccagc cgggtggtag cctgcgcctg        60
tcctgcgcgg ctagcggttt cacgtttagc agctacagca tgtactgggt gcgtcaagcg       120
ccaggcaaag gtctggaatg ggttgccgag attaagcaag acggttctgt tcagtattat       180
gtcagcgacg tgaagggtcg ttttaccatc agccgtgaca acgcgaaaaa cagcctgtat       240
ttgcagatga attccctgcg cgctgaagat accgcggtgt attactgtgc gaaaggtgag       300
attctgccgc tgtacttcga ttactggggc caaggcaccc tggttactgt ctcgagc         357

<210> SEQ ID NO 77
<211> LENGTH: 5
<212> TYPE: PRT
<213> ORGANISM: Artificial Sequence
<220> FEATURE:
<223> OTHER INFORMATION: C terminal extension

<400> SEQUENCE: 77

Val Thr Val Ser Ser
1               5
```

The invention claimed is:

1. A composition comprising
   a) an effective amount of at least one single variable heavy chain domain antibody capable of binding human IL-17A,
   b) 75-150 mM Tris/glycine, 80-125 mM L-arginine/glutamic acid, 4.5-29.5% propylene glycol and 7.5-10% sorbitol at a pH of 8.0,
   100 mM Tris/glycine, 125 mM L-arginine/glutamic acid, 6% propylene glycol and 5% trehalose dihydrate at a pH of 8.0 or
   100 mM Tris/glycine, 150 mM L-arginine/glutamic acid, 7% propylene glycol at a pH of 8.0;
   wherein said single variable heavy chain domain antibody comprises a CDR1 having SEQ ID NO: 2, a CDR2 having SEQ ID NO: 3, and a CDR3 having SEQ ID NO: 4.

2. A composition according to claim 1 wherein said single variable heavy chain domain antibody comprises SEQ ID NO: 1 or a sequence having at least 95% homology thereto or SEQ ID NO: 74 or a sequence having at least 95% homology thereto.

3. A composition according to claim 1 wherein said composition comprises
   100 mM Tris/glycine, 80-125 0.1 150 mM L-arginine/glutamic acid, 0.1 15% sorbitol, and 0.1 30 6 15% propylene glycol,
   10% sorbitol 8.0;
   100 mM Tris/glycine, 125 mM L-arginine/glutamic acid, 6% propylene glycol and 5% trehalose dehydrate at a pH of 8.0 or
   100 mM Tris/glycine, 150 mM L-arginine/glutamic acid, and 7% propylene glycol at a pH of 8.0.

4. A composition according to claim 1 wherein said composition is suitable for topical administration, and/or comprising a penetration enhancer,
   optionally wherein said penetration enhancer is selected from diethylene glycol monoethyl ether, steareth-20, steareth-2, octyldecanol or isopropyl myristate.

5. A composition according to claim 1 further comprising a viscosity modifier, optionally wherein said viscosity modifier is poloxamer.

6. A composition according to claim 1 wherein the concentration of the single domain antibody is 10 mg/ml to 50 mg/ml, or wherein said composition is stable upon storage at 2-8° C., 20-25° C. or −70° C. for at least 1, 2, 3, 6 or 12 months.

7. A method of treating an autoimmune disease or a skin disorder comprising administering a therapeutically effective amount of a composition according to claim 1 to a subject in need thereof,
   wherein the skin disorder is psoriasis, spondyloarthropathies, uveitis, gingivitis or atopic dermatitis.

8. The method according to claim 7 wherein administration is topical.

9. A kit comprising a composition according to claim 1 and optionally instructions for use,
   optionally wherein the kit further comprises a reconstitution agent.

10. A method for making a formulation of claim 1 comprising combining an excipient and single domain antibody capable of binding IL-17A, wherein said single variable heavy chain domain antibody comprises a CDR1 having SEQ ID NO: 2, a CDR2 having SEQ ID NO: 3, and a CDR3 having SEQ ID NO: 4.

11. A liquid, cream, powder, lotion, gel, dressing, patch or plaster comprising a composition according to claim 1.

12. A composition according to claim 1 wherein said single variable heavy chain domain antibody comprises 75-100 mM Tris/glycine, 93.75-125 mM L-arginine/glutamic acid, 4.5-29.5% propylene glycol and 7.5-10% sorbitol at a pH of 8.0.

13. A freeze or spray dried composition comprising
   a) an effective amount of at least one single variable heavy chain domain antibody comprising a $V_H$ domain capable of binding human IL-17A and
   b) 75-100 mM Tris/glycine, 80-125 mM L-arginine/glutamic acid, 4.5-29.5% propylene glycol and 7.5-10% sorbitol at a pH of 8.0,
   100 mM Tris/glycine, 125 mM L-arginine/glutamic acid, 6% propylene glycol and 5% trehalose dihydrate at a pH of 8.0 or 100 mM Tris/glycine, 150 mM L-arginine/glutamic acid, 7% propylene glycol at a pH of 8.0;

wherein said single variable heavy chain domain antibody comprises a CDR1 having SEQ ID NO: 2, a CDR2 having SEQ ID NO: 3, and a CDR3 having SEQ ID NO: 4.

14. A composition according to claim 13 wherein said single variable heavy chain domain antibody comprises SEQ ID NO: 1 or a sequence having at least 95% homology thereto or SEQ ID NO: 74 or a sequence having at least 95% homology thereto.

15. A composition according to claim 14 comprising 100 mM Tris/glycine, about 80-125 mM L-arginine/glutamic acid, 6-15% propylene glycol and 10% sorbitol at a pH of 8.0; 100 mM Tris/glycine, 125 mM L-arginine/glutamic acid, 6% propylene glycol and 5% trehalose dihydrate at a pH of 8.0; or 100 mM Tris/glycine, 150 mM L-arginine/glutamic acid, 7% propylene glycol at a pH of 8.0.

16. A reconstituted freeze or spray dried composition comprising a composition according to claim 13 further comprising a reconstitution agent.

17. A method for making a reconstituted formulation for topical administration comprising providing a composition according to claim 13 and adding a reconstitution agent.

18. A composition according to claim 13 wherein said single variable heavy chain domain antibody comprises 75-100 mM Tris/glycine, 93.75-125 mM L-arginine/glutamic acid, 4.5-29.5% propylene glycol and 7.5-10% sorbitol at a pH of 8.0.

* * * * *

UNITED STATES PATENT AND TRADEMARK OFFICE
CERTIFICATE OF CORRECTION

PATENT NO. : 10,947,308 B2
APPLICATION NO. : 16/316925
DATED : March 16, 2021
INVENTOR(S) : Karen Bannister et al.

It is certified that error appears in the above-identified patent and that said Letters Patent is hereby corrected as shown below:

In the Claims

In Column 115, Claim 3 should be displayed as follows:
3. A composition according to claim 1 wherein said composition comprises
100 mM Tris/glycine, 80-125 mM L-arginine/glutamic acid, 6-15% propylene glycol,
10% sorbitol at a pH of 8.0;
100 mM Tris/glycine, 125 mM L-arginine/glutamic acid, 6% propylene glycol and 5% trehalose
dehydrate at a pH of 8.0 or
100 mM Tris/glycine, 150 mM L-arginine/glutamic acid, and 7% propylene glycol at a pH of 8.0.

Signed and Sealed this
Twentieth Day of February, 2024

Katherine Kelly Vidal
*Director of the United States Patent and Trademark Office*